(12) United States Patent
Higginson-Scott et al.

(10) Patent No.: US 12,091,694 B2
(45) Date of Patent: Sep. 17, 2024

(54) FC FUSION MOLECULES AND USES THEREOF

(71) Applicant: Seismic Therapeutic, Inc., Cambridge, MA (US)

(72) Inventors: Nathan Higginson-Scott, Hingham, MA (US); Nathan Rollins, Boston, MA (US); Jordan Anderson, Cambridge, MA (US); Yanfeng Zhou, Boxborough, MA (US); Alex Pellerin, Boston, MA (US); Ivan Mascanfroni, Worcester, MA (US)

(73) Assignee: SEISMIC THERAPEUTIC, INC., Watertown, MA (US)

( * ) Notice: Subject to any disclaimer, the term of this patent is extended or adjusted under 35 U.S.C. 154(b) by 0 days.

(21) Appl. No.: 18/512,556

(22) Filed: Nov. 17, 2023

(65) Prior Publication Data

US 2024/0167011 A1 May 23, 2024

Related U.S. Application Data

(60) Provisional application No. 63/493,385, filed on Mar. 31, 2023, provisional application No. 63/483,127, filed on Feb. 3, 2023, provisional application No. 63/384,253, filed on Nov. 18, 2022.

(51) Int. Cl.
| | | |
|---|---|---|
| C12N 9/52 | (2006.01) | |
| A61K 38/48 | (2006.01) | |
| A61P 11/00 | (2006.01) | |
| C07K 14/47 | (2006.01) | |

(52) U.S. Cl.
CPC ............ *C12N 9/52* (2013.01); *A61K 38/4873* (2013.01); *A61P 11/00* (2018.01); *C07K 14/47* (2013.01); *C07K 2319/30* (2013.01)

(58) Field of Classification Search
None
See application file for complete search history.

(56) References Cited

U.S. PATENT DOCUMENTS

| | | |
|---|---|---|
| 7,666,582 B2 | 2/2010 | Pawel-Rammingen et al. |
| 8,133,483 B2 | 3/2012 | Bjorck et al. |
| 8,552,158 B2 | 10/2013 | Fischer et al. |
| 8,563,691 B2 | 10/2013 | LeBowitz et al. |
| 8,691,544 B2 | 4/2014 | Nilsson |
| 8,785,168 B2 | 7/2014 | LeBowitz et al. |

(Continued)

FOREIGN PATENT DOCUMENTS

| | | |
|---|---|---|
| EP | 1276895 B1 | 3/2010 |
| EP | 1625393 B1 | 10/2010 |

(Continued)

OTHER PUBLICATIONS

Xie, Xingang et al., Chimeric Fusion between Clostridium Ramosum IgA Protease and IgG Fc Provides Long-Lasting Clearance of IgA Deposits in Mouse Models of IgA Nephropathy. Journal of the American Society of Nephrology, 33:5 (2022).

(Continued)

*Primary Examiner* — Karl J Puttlitz
(74) *Attorney, Agent, or Firm* — Goodwin Procter LLP

(57) ABSTRACT

Embodiments provided herein, provide for polypeptides and molecules comprising a polypeptide having protease activity and a variant Fc molecule, pharmaceutical compositions comprising the same, and methods that can be used to treat disorders, such as IgG mediated disorders.

16 Claims, 4 Drawing Sheets
Specification includes a Sequence Listing.

(56) References Cited

U.S. PATENT DOCUMENTS

| | | |
|---|---|---|
| 9,408,897 B2 | 8/2016 | Levinson et al. |
| 9,469,683 B2 | 10/2016 | LeBowitz et al. |
| 9,549,974 B2 | 1/2017 | Leenhouts et al. |
| 9,861,686 B2 | 1/2018 | Porgador et al. |
| 9,964,548 B2 | 5/2018 | Magnelli et al. |
| 10,696,959 B2 | 6/2020 | Kjellman et al. |
| 10,758,597 B2 | 9/2020 | Kjellman et al. |
| 10,973,889 B2 | 4/2021 | Kjellman et al. |
| 11,214,784 B2 | 1/2022 | Kjellman et al. |
| 11,524,057 B2 | 12/2022 | Kjellman et al. |
| 11,667,905 B2 | 6/2023 | Kjellman et al. |
| 2006/0140907 A1 | 6/2006 | Blumberg et al. |
| 2010/0261216 A1 | 10/2010 | Eser et al. |
| 2011/0223147 A1 | 9/2011 | Lebowitz et al. |
| 2015/0139984 A1 | 5/2015 | Brezski et al. |
| 2017/0007680 A1 | 1/2017 | LeBowitz et al. |
| 2018/0125949 A1 | 5/2018 | LeBowitz et al. |
| 2018/0164325 A1 | 6/2018 | Koll et al. |
| 2019/0002542 A1 | 1/2019 | Wang et al. |
| 2019/0144528 A1 | 5/2019 | Paul et al. |
| 2019/0262434 A1 | 8/2019 | Brown |
| 2019/0309277 A1 | 10/2019 | James et al. |
| 2020/0378982 A1 | 12/2020 | Ohta et al. |
| 2021/0015910 A1 | 1/2021 | Seele et al. |
| 2021/0040463 A1 | 2/2021 | Chu et al. |
| 2021/0163923 A1 | 6/2021 | McCafferty et al. |
| 2021/0260173 A1 | 8/2021 | Nellman et al. |
| 2022/0133864 A1 | 5/2022 | Kishimoto |
| 2022/0135677 A1 | 5/2022 | Van Eenennaam et al. |
| 2023/0302100 A1 | 9/2023 | Kjellman et al. |

FOREIGN PATENT DOCUMENTS

| | | | |
|---|---|---|---|
| EP | 2279210 | A2 | 2/2011 |
| EP | 2225273 | B1 | 5/2012 |
| EP | 2059530 | B1 | 8/2012 |
| EP | 2394173 | B1 | 3/2015 |
| EP | 3075386 | A1 | 10/2016 |
| EP | 3149034 | A2 | 4/2017 |
| EP | 2788017 | B1 | 5/2017 |
| EP | 3187508 | A1 | 7/2017 |
| EP | 3272773 | A1 | 1/2018 |
| EP | 3517623 | A1 | 7/2019 |
| EP | 3148576 | B1 | 10/2020 |
| EP | 3256580 | B1 | 7/2022 |
| EP | 4108768 | A1 | 12/2022 |
| EP | 3256579 | B1 | 8/2023 |
| WO | 2009075646 | A1 | 6/2009 |
| WO | 2016128559 | A1 | 8/2016 |
| WO | 2020073553 | A1 | 4/2020 |
| WO | 2021021989 | A1 | 2/2021 |
| WO | 2022031710 | A2 | 2/2022 |
| WO | 2023116817 | A1 | 6/2023 |
| WO | 2023175498 | A1 | 9/2023 |
| WO | 2024008943 | A1 | 1/2024 |
| WO | 2024036324 | A1 | 2/2024 |

OTHER PUBLICATIONS

Wenig, et al., "Structure of the streptococcal endopeptidase IdeS, a cysteine proteinase with strict specificity for lgG", Proc Natl Acad Sci USA, Dec. 2004, vol. 101 (50): pp. 17371-17376. Epub Dec. 2004. doi: 10.1073/pnas.0407965101.

Vindebro, et al., "Rapid IgG heavy chain cleavage by the streptococcal IgG endopeptidase IdeS is mediated by IdeS monomers and is not due to enzyme dimerization", FEBS Lett., Jun. 2013, vol. 587 (12): pp. 1818-1822. Epub May 2013. doi: 10.1016/j.febslet.2013.04.039.

Persson, et al., "Proteolytic processing of the streptococcal IgG endopeptidase IdeS modulates the functional properties of the enzyme and results in reduced immunorecognition", Molecular Immunology, Dec. 2015, vol. 68 (2 Pt A): pp. 176-184. Epub Sep. 2015. doi: 10.1016/j.molimm.2015.07.014.

Ishihara, et al., "Dentipain, a Streptococcus pyogenes IdeS protease homology, is a novel virulence factor of Treponema denticola", Bio Chem, Sep. 2010, vol. 391 (9): pp. 1047-1055. doi: 10.1515/BC.2010.113.

Hulting, et al., "Two novel IgG endopeptidases of Streptococcus equi", FEMS Microbiol. Lett., Sep. 2009, vol. 298(1): pp. 44-50. doi: 10.1111/j.1574-6968.2009.01698.x.

Agniswamy, et al., "Crystal structure of group A Streptococcus Mac-1: insight into dimer-mediated specificity for recognition of human lgG", Structure, Feb. 2006, vol. 14 (2): pp. 225-235. doi: 10.1016/j.str.2005.10.012.

Saltzman A., Deep Mutational Scanning to Identify IgG1 Fc Mutations Affecting its Affinity to EndoS2 [bachelor's thesis]. Emory University; May 2, 2023. 43 p.

PCT/US2023/080313—International Search Report and Written Opinion, Apr. 23, 2023, 19 pages.

FC FUSION MOLECULES AND USES THEREOF

CROSS-REFERENCE TO RELATED APPLICATIONS

This application claims priority to U.S. Provisional Application No. 63/384,253, filed Nov. 18, 2022, U.S. Provisional Application No. 63/483,127, filed Feb. 3, 2023, and U.S. Provisional Application No. 63/493,385, filed Mar. 31, 2023, each of which is hereby incorporated by reference in its entirety.

REFERENCE TO SEQUENCE LISTING SUBMITTED ELECTRONICALLY

The instant application contains a Sequence Listing which has been submitted electronically in XML file format and is hereby incorporated by reference in its entirety. Said XML copy, created on Nov. 16, 2023 is named "SES-006.XML" and is 63,289 bytes in size.

FIELD

The embodiments provided herein relate to polypeptides comprising a polypeptide having protease activity and an Fc moiety, and compositions comprising the same.

BACKGROUND

Immunoglobulin G-degrading enzyme of *S. pyogenes* (IdeS) is an extracellular cysteine protease produced by the human pathogen *S. pyogenes*. IdeS has an extraordinarily high degree of substrate specificity, with its only identified substrate being immunoglobulin G (IgG). IdeS catalyzes a single proteolytic cleavage in the lower hinge region of the heavy chains of all subclasses of human IgG. IdeS also catalyzes an equivalent cleavage of the heavy chains of some subclasses of IgG in various animals. IdeS efficiently cleaves IgG to Fc and F(ab')2 fragments. IdeS is a virulence factor of *S. pyogenes*, which is responsible for common infections like tonsillitis and strep throat. To date, IdeS-Fc molecules resistant to autocleavage have not been available. Pathogenic IgG antibodies constitute an important clinical problem contributing to the pathogenesis of a number of autoimmune conditions and acute transplant rejection. To be able to effectively reduce, or eliminate such antibodies is therefore an important clinical challenge. The embodiments provided for herein fulfill this need as well as others.

SUMMARY

In some embodiments, variant Fc polypeptides comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 1, provided that the variant Fc polypeptide comprises a set of mutations selected from: L234A, L235A, G237A, Y296Q, and P329K; L234A, L235A, G237A, Y296Q, S298K, and P329K; L234A, L235A, G237A, D265K, E269S, Y296Q, and P329K; or L234A, L235A, G237A, D265K, E269S, Y296Q, S298K, and P329K; as compared to SEQ ID NO: 1, are provided.

In some embodiments, variant Fc polypeptides comprising: an amino acid sequence of SEQ ID NO: 19; an amino acid sequence of SEQ ID NO: 21; an amino acid sequence of SEQ ID NO: 22; an amino acid sequence of SEQ ID NO: 23; an amino acid sequence of SEQ ID NO: 24; or an amino acid sequence of SEQ ID NO: 25, are provided.

In some embodiments, polypeptides comprising a polypeptide having protease activity and an Fc polypeptide, wherein the polypeptide having protease activity is covalently or non-covalently connected (e.g. conjugated via a peptide bond or through electrostatic interactions) to the Fc polypeptide, are provided.

In some embodiments, polypeptides having a formula from N-terminus to C-terminus selected from: N1-P1-variant Fc; variant Fc-P1-N1; P1-variant Fc-N1; or N1-variant Fc-P1, wherein, P1 comprises a polypeptide having protease activity; N1 comprises a nanobody; and variant Fc is a variant Fc polypeptide, are provided.

In some embodiments, polypeptides having a formula from N-terminus to C-terminus selected from: N1-P1-variant Fc; variant Fc-P1-N1; P1-variant Fc-N1; or N1-variant Fc-P1, wherein, P1 comprises a polypeptide having protease activity; N1 comprises a nanobody; variant Fc is a variant Fc polypeptide; and optionally wherein the protease is a glycosylation-resistant protease, are provided.

In some embodiments, polypeptides having a formula from N-terminus to C-terminus selected from: N1-P1; or P1-N1, wherein, P1 comprises a polypeptide having protease activity; N1 comprises a nanobody; and optionally wherein the protease is a glycosylation-resistant protease, are provided.

In some embodiments, polypeptides having a formula from N-terminus to C-terminus selected from: N1-IdeS-variant Fc; variant Fc-IdeS-N1; IdeS-variant Fc-N1; or N1-variant Fc-IdeS, wherein, N1 comprises a nanobody; and variant Fc is a variant Fc polypeptide, are provided.

In some embodiments, methods of treating a disease or disorder in a subject, comprising administering any of the polypeptides provided herein to the subject to treat the disease or disorder, are provided.

In some embodiments, methods of treating a transplant subject comprising administering a therapeutically effective amount of any of the polypeptides provided herein to the subject, thereby treating the transplant (recipient) subject, are provided.

In some embodiments, methods of improving a gene-therapy in subject comprising administering a therapeutically effective amount of any of the polypeptides provided herein to the subject, thereby improving the gene-therapy in the subject, are provided.

In some embodiments, methods of treating a subject having, or at risk, or elevated risk, for having, an IgG mediated disease or disorder, comprising administering a therapeutically effective amount of any of the polypeptides provided herein, thereby treating the subject, are provided.

In some embodiments, methods of making the polypeptides provided herein, are provided.

DETAILED DESCRIPTION

Figure 1:
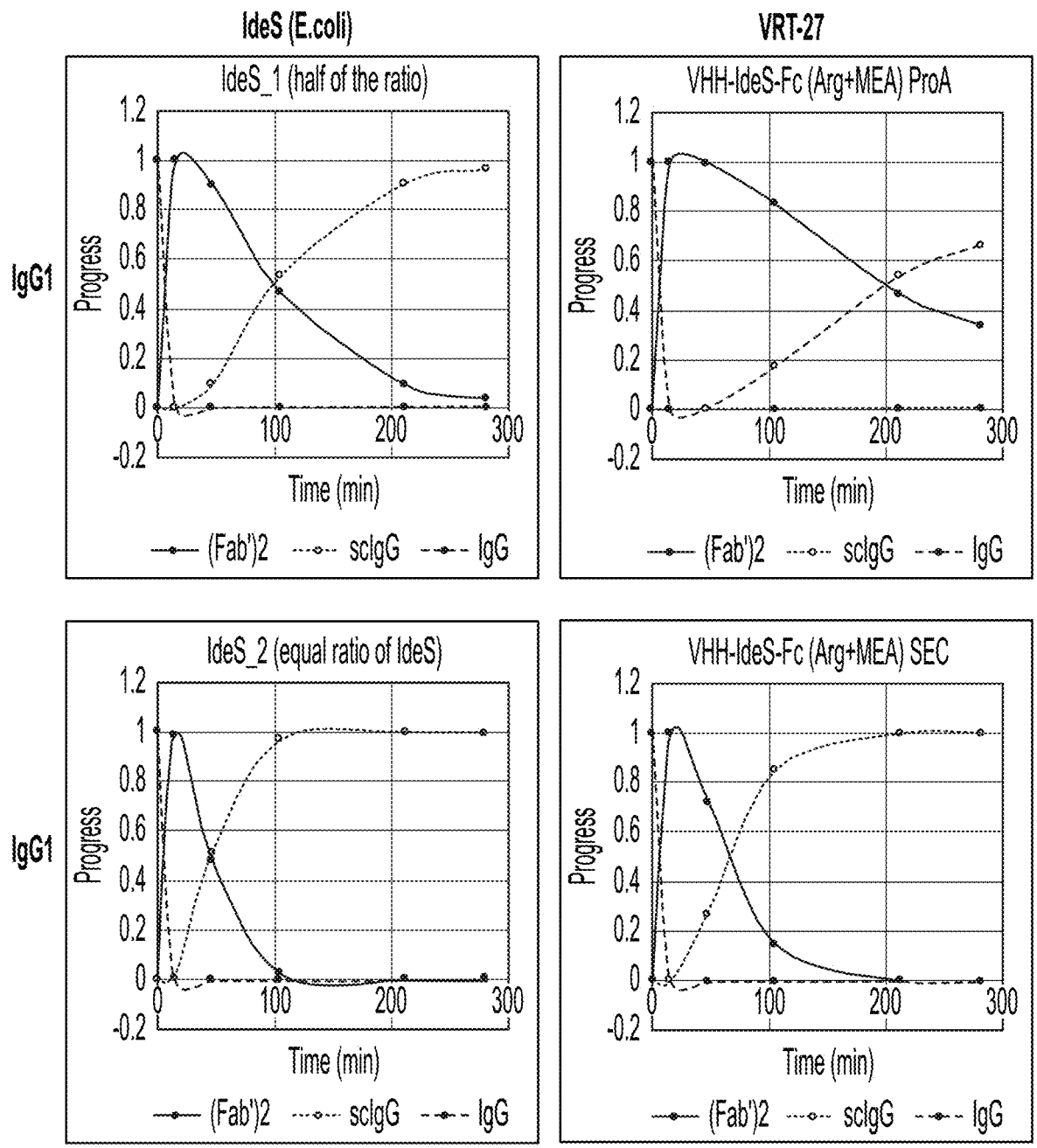
FIG. 1 illustrates performance of IdeS-Fc polypeptide against IdeS.

As used herein and in the appended claims, the singular forms "a", "an" and "the" include plural reference unless the context clearly dictates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by +5% and remain within the scope of the disclosed embodiments. Thus, about 100 means 95 to 105.

As used herein, the term "animal" includes, but is not limited to, humans and non-human vertebrates such as wild, domestic, and farm animals. As used herein, the term "mammal" means a rodent (i.e., a mouse, a rat, or a guinea pig), a monkey, a cat, a dog, a cow, a horse, a pig, or a human. In some embodiments, the mammal is a human.

As used herein, the term "contacting" means bringing together of two elements in an in vitro system or an in vivo system. For example, "contacting" a therapeutic compound with an individual or patient or cell includes the administration of the compound to an individual or patient, such as a human, as well as, for example, introducing a compound into a sample containing a cellular or purified preparation containing target.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps. Any composition or method that recites the term "comprising" should also be understood to also describe such compositions as consisting, consisting of, or consisting essentially of the recited components or elements.

As used herein, the term "fused" or "linked" when used in reference to a protein or molecule having different domains or heterologous sequences means that the protein domains are part of the same peptide chain that are connected to one another with either peptide bonds or other covalent bonding. The domains or section can be linked or fused directly to one another or another domain or peptide sequence can be between the two domains or sequences and such sequences would still be considered to be fused or linked to one another.

As used herein, the term "individual," "subject," or "patient," used interchangeably, means any animal, including mammals, such as mice, rats, other rodents, rabbits, dogs, cats, swine, cattle, sheep, horses, or primates, such as humans.

As used herein, the term "inhibit" refers to a result, symptom, or activity being reduced as compared to the activity or result in the absence of the compound that is inhibiting the result, symptom, or activity. In some embodiments, the result, symptom, or activity, is inhibited by about, or, at least, 10%, 20%, 30%, 40%, 50%, 60%, 70%, 80%, 90%, 95%, or 99%. An result, symptom, or activity can also be inhibited if it is completely elimination or extinguished.

As used herein, the phrase "in need thereof" means that the subject has been identified as having a need for the particular method or treatment. In some embodiments, the identification can be by any means of diagnosis. In any of the methods and treatments described herein, the subject can be in need thereof. In some embodiments, the subject is in an environment or will be traveling to an environment in which a particular disease, disorder, or condition is prevalent.

As used herein, the phrase "integer from X to Y" means any integer that includes the endpoints. For example, the phrase "integer from 1 to 5" means 1, 2, 3, 4, or 5.

As used herein, the phrase "ophthalmically acceptable" means having no persistent detrimental effect on the treated eye or the functioning thereof, or on the general health of the subject being treated. However, it will be recognized that transient effects such as minor irritation or a "stinging" sensation are common with topical ophthalmic administration of drugs and the existence of such transient effects is not inconsistent with the composition, formulation, or ingredient (e.g., excipient) in question being "ophthalmically acceptable" as herein defined. In some embodiments, the pharmaceutical compositions can be ophthalmically acceptable or suitable for ophthalmic administration.

In some embodiments, the term "therapeutic molecule" can be used interchangeably with "therapeutic compound." "molecule." or "therapeutic," and refers to any polypeptide, or protein described herein.

As used herein, the term "position." is meant to refer to a location in the sequence of a polypeptide. Positions may be numbered sequentially, or according to an established format, for example the EU numbering system based on Kabat's amino acid positions. For example, position 298 is a position in the human antibody IgG1.

"Specific binding" or "specifically binds to" or is "specific for" a particular antigen, target, or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen, target, or an epitope can be exhibited, for example, by an antibody having a $K_D$ for an antigen or epitope of at least about $10^{-4}$M, at least about $10^{-5}$M, at least about $10^{-6}$M, at least about $10^{-7}$M, at least about $10^{-8}$M, at least about $10^{-9}$M, alternatively at least about $10^{-10}$M, at least about $10^{-11}$M, at least about $10^{-12}$M, or greater, where $K_D$ refers to a dissociation rate of a particular antibody-target interaction. Typically, an antibody that specifically binds an antigen or target will have a $K_D$ that is, or at least, 2-, 4-, 5-, 10-, 20-, 50-, 100-, 500-, 1000-, 5,000-, 10,000-, or more times greater for a control molecule relative to the antigen or epitope.

In some embodiments, specific binding for a particular antigen, target, or an epitope can be exhibited, for example, by an antibody having a $K_A$ or $K_a$ for a target, antigen, or epitope of at least 2-, 4-, 5-, 20-, 50-, 100-, 500-, 1000-, 5,000-, 10,000- or more times greater for the target, antigen, or epitope relative to a control, where $K_A$ or $K_a$ refers to an association rate of a particular antibody-antigen interaction.

As provided herein, the compounds and compositions provided for herein can be used in methods of treatment as provided herein. As used herein, the terms "treat," "treated," or "treating" mean both therapeutic treatment and prophylactic measures wherein the object is to slow down (lessen) an undesired physiological condition, disorder or disease, or obtain beneficial or desired clinical results. For purposes of these embodiments, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response without excessive levels of side effects. Treatment also includes prolonging survival, as applicable for a specific disease, as compared to expected survival if not receiving treatment. Thus, "treatment of an autoimmune condition" or "treating autoimmunity" means an activity that alleviates or ameliorates any of the primary phenomena or secondary symptoms associated with the autoimmune condition other condition described herein when the terms "treat," "treated," or "treating" are used in conjunction with such condition.

As used herein, terms "variant," "molecule," "therapeutic," "therapeutic compound," "compound," "polypeptide," or "protein" can be used interchangeably and relate to the variants, molecules, therapeutics, therapeutic compounds, compounds, polypeptides, and proteins disclosed herein.

Variant Fc Molecules a wild-type protein, e.g., a heavy chain constant region, is the amino acid sequence of the protein as it occurs in nature. Due to allotypic differences, there can be more than one amino acid sequence for a wild-type protein. For example, there are several allotypes of naturally occurring human IGg1 heavy chain constant regions (e.g., Jeffries et al. (2009) mAbs 1:1).

An immunoglobulin may be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. In certain embodiments, the antibodies described herein are of the human IgG1 or IgG2 subtype. Immunoglobulins, e.g., human IgG1, exist in several allotypes, which differ from each other in at most a few amino acids.

In some embodiments, the IgG proteins (hinge region underlined) are as provided in Table 1.

TABLE 1

| Isotype | Sequence |
|---------|----------|
| IgG1 | ASTKGPSVFPLAPSSKSTSGGTAALGCLVKDYFPEPVTVSWNSGALTSGVHTFPAVLQSSGLYSLSSVVTVPSS SLGTQTYICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPIEKTISKA KGQPREPQVYTLPPSRDELTKNQVSLTCLVKGFYPSDIAVEWESNGQPENNYKTTPPVLDSGSFFLYSKLTVD KSRWQQGNVFSCSVMHEALHNHYTQKSLSLSPGK (SEQ ID NO: 1) |
| IgG2 | ASTKGPSVFPLAPCSRSTSESTAALGCLVKDYFPEPVTVSWNSGALTSGVHTFPAVLQSSGLYSLSSVVTVPSS NFGTQTYTCNVDHKPSNTKVDKTVERKCCVECPPCPAPPVAGPSVFLFPPKPKDTLMISRTPEVTCVVVDVSHE DPEVQFNWYVDGVEVHNAKTKPREEQFNSTFRVVSVLTVVHQDWLNGKEYKCKVSNKGLPAPIEKTISKTKGQP REPQVYTLPPSREEMTKNQVSLTCLVKGFYPSDISVEWESNGQPENNYKTTPPMLDSDGSFFLYSKLTVDKSRW QQGNVFSCSVMHEALHNHYTQKSLSLSPGK (SEQ ID NO: 2) |
| IgG3 | ASTKGPSVFPLAPCSRSTSGGTAALGCLVKDYFPEPVTVSWNSGALTSGVHTFPAVLQSSGLYSLSSVVTVPSS SLGTQTYTCNVNHKPSNTKVDKRVELKTPLGDTTHTCPRCPEPKSCDTPPPCPRCPEPKSCDTPPPCPRCPEPK SCDTPPPCPRCPAPELLGGPSVFLFPPKPKDTLMISRTPEVTCVVVDVSHEDPEVQFKWYVDGVEVHNAKTKPR EEQYNSTFRVVSVLTVLHQDWLNGKEYKCKVSNKALPAPIEKTISKTKGQPREPQVYTLPPSREEMTKNQVSLT CLVKGFYPSDIAVEWESSGQPENNYNTTPPMLDSDGSFFLYSKLTVDKSRWQQGNIFSCSVMHEALHNRFTQKS LSLSPGK (SEQ ID NO: 3) |
| IgG4 | ASTKGPSVFPLAPCSRSTSESTAALGCLVKDYFPEPVTVSWNSGALTSGVHTFPAVLQSSGLYSLSSVVTVPSS SLGTKTYTCNVDHKPSNTKVDKRVESKYGPPCPSCPAPEFLGGPSVFLFPPKPKDTLMISRTPEVTCVVVDVSQ EDPEVQFNWYVDGVEVHNAKTKPREEQFNSTYRVVSVLTVLHQDWLNGKEYKCKVSNKGLPSSIEKTISKAKGQ PREPQVYTLPPSQEEMTKNQVSLTCLVKGFYPSDIAVEWESNGQPENNYKTTPPVLDSDGSFFLYSRLTVDKSR WQEGNVFSCSVMHEALHNHYTQKSLSLSLGK (SEQ ID NO: 4) |

As used herein, "isotype" refers to the immunoglobulin class (e.g., IgG1, IgG2, IgG3, IgG4, IgM, IgA1, IgA2, IgD, and IgE antibody) that is encoded by the heavy chain constant domain genes. The full-length amino acid sequence of each wild type human IgG constant region (including all domains, i.e., CH1 domain, hinge, CH2 domain, and CH3 domain) is cataloged in the UniProt database available on-line, e.g., as P01857 (IgG1), P01859 (IgG2), P01860 (IgG3), and P01861 (IgG4), or different allotypes thereof (SEQ ID NOs: 1, 2, 3, and 4, respectively). As used herein, a domain of a heavy chain constant region, e.g., the hinge, is of an "IgG1 isotype," "IgG2 isotype," "IgG3 isotype," or "IgG4 isotype," if the domain comprises the amino acid sequence of the corresponding domain of the respective isotype, or a variant thereof (that has a higher homology to the corresponding domain of the respective isotype than it does to that of the other isotypes).

"Allotype" refers to naturally occurring variants within a specific isotype group, which variants differ in a few amino acids (see, e.g., Jefferies et al. (2009) mAbs 1:1). Molecules described herein may be of any allotype.

A "wild-type" protein or portion thereof is a version of the protein as it is found in nature. An amino acid sequence of An "Fc region" (fragment crystallizable region) or "Fc polypeptide" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region of an antibody of isotype IgG comprises the heavy chain constant region of the antibody excluding the first constant region immunoglobulin domain (CH1). In IgG, IgA and IgD antibody isotypes, the Fc region comprises CH2 and CH3 constant domains in each of the antibody's two heavy chains; IgM and IgE Fc regions comprise three heavy chain constant domains (CH domains 2-4) in each polypeptide chain. For IgG, the Fc region comprises immunoglobulin domains consisting of the hinge, CH2 and CH3. For purposes herein, the Fc region is defined as starting at amino acid 216 and ending at amino acid 447, wherein the numbering is according to the EU index as in Kabat. Kabat et al. (1991) Sequences of Proteins of Immunological Interest, National Institutes of Health, Bethesda, MD, and according to FIGS. 3c-3f of U.S. Pat. App. Pub. No. 2008/0248028. In some embodiments, the Fc region comprises the hinge region. The Fc may be a native (or naturally-occurring or wild-type) Fc, including any allotypic variant, or a variant Fc (e.g., a non-naturally occurring Fc), comprising, e.g., 1, 2, 3, 4, 5, 1-5, 1-10 or more amino acid mutations, e.g., substitutions, additions or deletions. For example, a variant Fc may comprise an amino acid sequence that is at least 75%, 80%, 85%, 90%, 95%, 96%, 97%, 98% or 99% identical to a wild-type Fc. Modified or mutated Fcs may have enhanced or reduced effector function and/or half-life. Fc may refer to this region in isolation or in the context of an Fc-comprising protein polypeptide such as a "binding protein comprising an Fc region," also referred to as an "Fc fusion protein" (e.g., an antibody or immunoadhesin). In some embodiments, modified or variant Fc molecules have enhanced binding to FcγRIIb.

A "hinge", "hinge domain" or "hinge region" or "antibody hinge region" refers to the domain of a heavy chain constant region that joins the CH1 domain to the CH2 domain and includes the upper, middle, and lower portions of the hinge (Roux et al. J. Immunol. 1998 161:4083). The hinge provides varying levels of flexibility between the binding and effector regions of an antibody and also provides sites for intermolecular disulfide bonding between the two heavy chain constant regions. The term "hinge" includes wild-type hinges (such as those set forth in Table 3), as well as variants thereof (e.g., non-naturally-occurring hinges or modified hinges). For example, the term "IgG1 hinge" includes wild-type IgG1 hinge, as shown below, and variants having 1, 2, 3, 4, 5, 1-3, 1-5, 3-5 and/or at most 5, 4, 3, 2, or 1 mutations, e.g., substitutions, deletions or additions. In some embodiments, the hinge regions are as provided in Table 2.

includes wild-type CH2 domains, as well as variants thereof (e.g., non-naturally-occurring CH2 domains or modified CH2 domains). For example, the term "CH2 domain" includes wild-type CH2 domains and variants thereof having 1, 2, 3, 4, 5, 1-3, 1-5, 3-5 and/or at most 5, 4, 3, 2, or 1 mutations, e.g., substitutions, deletions or additions.

The term "CH3 domain" refers to the heavy chain constant region that is C-terminus to the CH2 domain in a heavy chain constant domain. As used herein, a CH3 domain includes wild-type CH3 domains, as well as variants thereof (e.g., non-naturally-occurring CH3 domains or modified CH3 domains). For example, the term "CH3 domain" includes wild-type CH3 domains and variants thereof having 1, 2, 3, 4, 5, 1-3, 1-5, 3-5 and/or at most 5, 4, 3, 2, or 1 mutations, e.g., substitutions, deletions or additions.

Provided herein are variant Fc polypeptides comprising variant Fc polypeptides, e.g., Fc polypeptides that have a mutated sequence region, relative to wild-type Fc polypeptide. Exemplary variant Fc molecules comprising variant Fc polypeptides include an IgG1 hinge, a CH1 domain, a CH2 domain and a CH3 domain, wherein at least one of these constant domains has residues that are not wild-type residues, as compared to SEQ ID NO: 1, 2, 3, or 4. A variant Fc polypeptide may have effector function similar to that of wild-type IgG, or may be engineered to have enhanced effector function relative to that of the wild-type IgG. A variant Fc polypeptide may comprise a wild-type CH1, hinge, CH2 and/or CH3 domain, or a variant thereof, e.g., a CH1, hinge, CH2 and/or CH3 domain having one or more amino acid substitutions, deletions or additions relative to

TABLE 2

| Isotype | Hinge Sequence |
|---|---|
| IgG1 | EPKSCDKTHTCPPCPAPELLGGP (SEQ ID NO: 5) |
| IgG2 | ELKTPLGDTTHTCPRCPAPELLGGP (SEQ ID NO: 6) |
| IgG3 | ELKTPLGDTTHTCPRCPEPKSCDTPPPCPRCPEPKSCDTPPPCPRCPEPKSCDTPPPCPRCPAPEL LGGP (SEQ ID NO: 7) |
| IgG4 | ESKYGPPCPSCPAPEFLGGP (SEQ ID NO: 8) |

The term "CH1 domain" refers to the heavy chain constant region linking the variable domain to the hinge in a heavy chain constant domain. As used herein, a CH1 domain includes wild type CH1 domains, as well as variants thereof (e.g., non-naturally-occurring CH1 domains or modified CH1 domains). For example, the term "CH1 domain" includes wild-type CH1 domains and variants thereof having 1, 2, 3, 4, 5, 1-3, 1-5, 3-5 and/or at most 5, 4, 3, 2, or 1 mutations, e.g., substitutions, deletions or additions.

the corresponding wild-type domain, and/or having an amino acid sequence that is at least 70%, at least 75&, at least 80%, at least 85%, at least 90%, at least 91%, at least 92%, at least 93%, at least 94%, at least 95%, at least 96%, at least 97%, at least 98%, or at least 99% identical, or more, to the corresponding wild-type sequence.

In some embodiments, the IgG proteins are as provided in Table 6.

TABLE 6

| Isotype | CH2-CH3 Sequence |
|---|---|
| IgG1 | DKTHTCPPCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLYSKLTVDKSRWQQGNVFS CSVMHEALHNHYTQKSLSLSPGK (SEQ ID NO: 56) |

The term "CH2 domain" refers to the heavy chain constant region linking the hinge to the CH3 domain in a heavy chain constant domain. As used herein, a CH2 domain In some embodiments, a variant Fc polypeptide comprises one or more mutations that confers resistance to recognition by a protease. In some embodiments, a variant Fc polypeptide comprises one or more mutations that confers resistance to proteolytic cleavage. In some embodiments, a variant Fc polypeptide comprises one or more mutations that confers resistance to binding by a protease. In some embodiments, a variant Fc polypeptide comprises one or more mutations that confer resistance to recognition by a protease and proteolytic cleavage. In some embodiments, the variant Fc polypeptide is resistant to proteolytic cleavage. In some embodiments, the variant Fc polypeptide is resistant to binding by a protease. In some embodiments, the variant Fc polypeptide is resistant to proteolytic cleavage and/or binding by a protease.

In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 1, provided that the variant Fc polypeptide comprises an amino acid mutation at any one, or more, position between positions 234 and 329, as compared to SEQ ID NO: 1, wherein the mutation comprises an insertion, a deletion or a substitution.

In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 1, provided that the variant Fc polypeptide comprises a mutation corresponding to L234A mutation, as compared to SEQ ID NO: 1.

In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 1, provided that the variant Fc polypeptide comprises a mutation corresponding to L235A mutation, as compared to SEQ ID NO: 1.

In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 1, provided that the variant Fc polypeptide comprises a mutation corresponding to G237A mutation, as compared to SEQ ID NO: 1.

In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 1, provided that the variant Fc polypeptide comprises a mutation corresponding to Y296Q mutation, as compared to SEQ ID NO: 1.

In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 1, provided that the variant Fc polypeptide comprises a mutation corresponding to P329K mutation, as compared to SEQ ID NO: 1.

In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 1, provided that the variant Fc polypeptide comprises a set of mutations corresponding to L234A, L235A, and G237A mutations, as compared to SEQ ID NO: 1.

In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 1, provided that the variant Fc polypeptide comprises a set of mutations corresponding to Y296Q and P329K mutations, as compared to SEQ ID NO: 1.

In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 1, provided that the variant Fc polypeptide comprises a set of mutations corresponding to L234A, L235A, G237A, Y296Q, and P329K mutations, as compared to SEQ ID NO: 1.

In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 56, provided that the variant Fc polypeptide comprises a set of mutations corresponding to L234A, L235A, G237A, Y296Q, and P329K mutations, as compared to SEQ ID NO: 1.

In some embodiments, a variant Fc polypeptide comprises a mutation set of L234A, L235A, G237A, Y296Q, and P329K as compared to SEQ ID NO: 1, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the mutation set as compared to SEQ ID NO: 1.

TABLE 3

| ID | Fc Seq |
|---|---|
| VFC-1 | DKTHTCPPCPAPEAAGAPSVFLFPPKPKDTLMISRTPEVTCVVVDVSHEDPEVKFNWYVDGVEVHNA KTKPREEQQNSTYRVVSVLTVLHQDWLNGKEYKCKVSNKALKAPIEKTISKAKGQPREPQVYTLPPS RDELTKNQVSLTCLVKGFYPSDIAVEWESNGQPENNYKTTPPVLDSDGSFFLYSKLTVDKSRWQQGN VFSCSVMHEALHNHYTQKSLSLSPGK (SEQ ID NO: 19) |
| VFC-2 | DKTHTCPPCPAPEAAGAPSVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFFLYSKLTVDKSRWQQGN VFSCSVMHEALHNHYTQKSLSLSPGK (SEQ ID NO: 20) |

TABLE 3-continued

| ID | Fc Seq |
|---|---|
| VFC-3 | DKTHTCPPCPAPEAAGAPSVFLFPPKPKDTLMISRTPEVTCVVVKVSHSDPEVKENWYVDGVEVHNA<br>KTKPREEQQNSTYRVVSVLTVLHQDWLNGKEYKCKVSNKALKAPIEKTISKAKGQPREPQVYTLPPS<br>RDELTKNQVSLTCLVKGFYPSDIAVEWESNGQPENNYKTTPPVLDSDGSFFLYSKLTVDKSRWQQGN<br>VFSCSVMHEALHNHYTQKSLSLSPGK (SEQ ID NO: 21) |
| VFC-4 | DKTHTCPPCPAPEAAGAPSVFLFPPKPKDTLMISRTPEVTCVVVKVSHSDPEVKFNWYVDGVEVHNA<br>KTKPREEQQNKTYRVVSVLTVLHQDWLNGKEYKCKVSNKALKAPIEKTISKAKGQPREPQVYTLPPS<br>RDELTKNQVSLTCLVKGFYPSDIAVEWESNGQPENNYKTTPPVLDSDGSFFLYSKLTVDKSRWQQGN<br>VFSCSVMHEALHNHYTQKSLSLSPGK (SEQ ID NO: 22) |
| VFC-5 | DKTHTCPPCPAPEAAGAPSVFLFPPKPKDTLMISRTPEVTCVVVDVSHEDPEVKENWYVDGVEVHNA<br>KTKPREEQQNSTYRVVSVLTVLHQDWLNGKEYKCKVSNKALKAPIEKTISKAKGQPREPQVYTLPPS<br>RDELTKNQVSLTCLVKGFYPSDIAVEWESNGQPENNYKTTPPVLDSDGSFFLYSKLTVDKSRWQQGN<br>VFSCSVMHEALHNHYTQKSLSLSPG (SEQ ID NO: 23) |
| VFC-6 | DKTHTCPPCPAPEAAGAPSVFLFPPKPKDTLMISRTPEVTCVVVDVSHEDPEVKENWYVDGVEVHNA<br>KTKPREEQQNSTYRVVSVLTVLHQDWLNGKEYKCKVSNKALKAPIEKTISKAKGQPREPQVYTLPPS<br>RDELTKNQVSLWCLVKGFYPSDIAVEWESNGQPENNYKTTPPVLDSDGSFFLYSKLTVDKSRWQQGN<br>VFSCSVMHEALHNHYTQKSLSLSPG (SEQ ID NO: 24) |
| VFC-7 | DKTHTCPPCPAPEAAGAPSVFLFPPKPKDTLMISRTPEVTCVVVDVSHEDPEVKENWYVDGVEVHNA<br>KTKPREEQQNSTYRVVSVLTVLHQDWLNGKEYKCKVSNKALKAPIEKTISKAKGQPREPQVYTLPPS<br>RDELTKNQVSLSCAVKGFYPSDIAVEWESNGQPENNYKTTPPVLDSDGSFFLVSKLTVDKSRWQQGN<br>VFSCSVMHEALHNHYTQKSLSLSPG (SEQ ID NO: 25) |
| VFC-8 | DKTHTSPPCPAPEAAGAPSVFLFPPKPKDTLMISRTPEVTCVVVDVSHEDPEVKFNWYVDGVEVHNA<br>KTKPREEQQNSTYRVVSVLTVLHQDWLNGKEYKCKVSNKALKAPIEKTISKAKGQPREPQVYTLPPS<br>RDELTKNQVSLTCLVKGFYPSDIAVEWESNGQPENNYKTTPPVLDSDGSFFLYSKLTVDKSRWQQGN<br>VFSCSVMHEALHNHYTQKSLSLSPGK (SEQ ID NO: 42) |
| VFC-9 | DKTHISPPSPAPEAAGAPSVFLFPPKPKDTLMISRTPEVTCVVVDVSHEDPEVKENWYVDGVEVHNA<br>KTKPREEQQNSTYRVVSVLTVLHQDWLNGKEYKCKVSNKALKAPIEKTISKAKGQPREPQVYTLPPS<br>RDELTKNQVSLTCLVKGFYPSDIAVEWESNGQPENNYKTTPPVLDSDGSFFLYSKLTVDKSRWQQGN<br>VFSCSVMHEALHNHYTQKSLSLSPGK (SEQ ID NO: 43) |
| VFC-10 | DKTHTCPPCPAPELLGDSGVFLFPPKPKDTLMISRTPEVTCVVVDVSHDEPEVKENWYVDGVEVHNA<br>KTKPREEQYNSTYRVVSVLTVLHQDWLNGKEYKCKVSNKALPRPIEKTISKAKGQPREPQVYTLPPS<br>RDELTKNQVSLWCLVKGFYPSDIAVEWESNGQPENNYKTTPPVLDSDGSFFLYSKLTVDKSRWQQGN<br>VFSCSVMHEALHNHYTQKSLSLSPGK (SEQ ID NO: 44) |
| VFC-11 | DKTHTCPPCPAPEFEGGPSVFLFPPKPKDTLMISRTPEVTCVVVDVSDEDGEVKFNWYVDGVEVHNA<br>KTKPREEQYNSTYRVVSVLTVLHQDWLNGKEYKCKVSNKALAAPIEKTISKAKGQPREPQVYTLPPS<br>RDELTKNQVSLSCAVKGFYPSDIAVEWESNGQPENNYKTTPPVLDSDGSFFLVSKLTVDKSRWQQGN<br>VFSCSVMHEALHNHYTQKSLSLSPGK (SEQ ID NO: 45) |
| VFC-12 | DKTHTCPPCPAPEFEGGPSVFLFPPKPKDTLMISRTPEVTCVVVDVSQEDPEVQFNWYVDGVEVHNA<br>KTKPREEQFNSTYRVVSVLTVLHQDWLNGKEYKCKVSNKALPSSIEKTISKAKGQPREPQVYTLPPS<br>RDELTKNQVSLWCLVKGFYPSDIAVEWESNGQPENNYKTTPPVLDSDGSFFLYSKLTVDKSRWQQGN<br>VFSCSVMHEALHNHYTQKSLSLSPGK (SEQ ID NO: 46) |
| VFC-13 | DKTHTCPPCPAPEFEGGPSVFLFPPKPKDTLMISRTPEVTCVVVDVSDEDGEVQFNWYVDGVEVHNA<br>KTKPREEQFNSTYRVVSVLTVLHQDWLNGKEYKCKVSNKALASSIEKTISKAKGQPREPQVYTLPPS<br>RDELTKNQVSLSCAVKGFYPSDIAVEWESNGQPENNYKTTPPVLDSDGSFFLVSKLTVDKSRWQQGN<br>VFSCSVMHEALHNHYTQKSLSLSPGK (SEQ ID NO: 47) |
| VFC-14 | DKTHISPPCPAPEAAGAPSVFLFPPKPKDTLMISRTPEVTCVVVDVSHEDPEVKENWYVDGVEVHNA<br>KTKPREEQYNSTYRVVSVLTVLHQDWLNGKEYKCKVSNKALPAPIEKTISKAKGQPREPQVYTLPPS<br>RDELTKNQVSLTCLVKGFYPSDIAVEWESNGQPENNYKTTPPVLDSDGSFFLYSKLTVDKSRWQQGN<br>VFSCSVMHEALHNHYTQKSLSLSPGK (SEQ ID NO: 48) |
| VFC-15 | DKTHISPPCPAPELLGGPSVFLFPPKPKDTLMISRTPEVTCVVVDVSHEDPEVKENWYVDGVEVHNA<br>KTKPREEQYNSTYRVVSVLTVLHQDWLNGKEYKCKVSNKALPAPIEKTISKAKGQPREPQVYTLPPS<br>RDELTKNQVSLTCLVKGFYPSDIAVEWESNGQPENNYKTTPPVLDSDGSFFLYSKLTVDKSRWQQGN<br>VFSCSVMHEALHNHYTQKSLSLSPGK (SEQ ID NO: 49) |

In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any sequence provided in Table 3. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, 20, 21, 22, 23, 24, 25, 42, 43, 44, 45, 46, 47, 48, or 49. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 25. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 42. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 43. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 44. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 45. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 46. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 47. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 48. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 49.

In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any sequence provided in Table 3, provided that the variant Fc polypeptide comprises one or more mutations at position 234, 235, 237, 265, 269, 296, 298, 329, or any combination thereof. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, 20, 21, 22, 23, 24, or 25, provided that the variant Fc polypeptide comprises one or more mutations at position 234, 235, 237, 265, 269, 296, 298, 329, or any combination thereof. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, provided that the variant Fc polypeptide comprises one or more mutations at position 234, 235, 237, 265, 269, 296, 298, 329, or any combination thereof. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, provided that the variant Fc polypeptide comprises one or more mutations at position 234, 235, 237, 265, 269, 296, 298, 329, or any combination thereof. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, provided that the variant Fc polypeptide comprises one or more mutations at position 234, 235, 237, 265, 269, 296, 298, 329, or any combination thereof. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, provided that the variant Fc polypeptide comprises one or more mutations at position 234, 235, 237, 265, 269, 296, 298, 329, or any combination thereof. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, provided that the variant Fc polypeptide comprises one or more mutations at position 234, 235, 237, 265, 269, 296, 298, 329, or any combination thereof. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, provided that the variant Fc polypeptide comprises one or more mutations at position 234, 235, 237, 265, 269, 296, 298, 329, or any combination thereof. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, provided that the variant Fc polypeptide comprises one or more mutations at position 234, 235, 237, 265, 269, 296, 298, 329, or any combination thereof.

In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any sequence provided in Table 3, and further comprises one or more mutations of L234A, L235A, G237A, Y296Q, P329K, or any combination thereof. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, 20, 21, 22, 23, 24, or 25, provided that the variant Fc polypeptide comprises one or more mutations of L234A, L235A, G237A, Y296Q, P329K, or any combination thereof. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, provided that the variant Fc polypeptide comprises one or more mutations of L234A, L235A, G237A, Y296Q, P329K, or any combination thereof. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, provided that the variant Fc polypeptide comprises one or more mutations of L234A, L235A, G237A, Y296Q, P329K, or any combination thereof. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, provided that the variant Fc polypeptide comprises one or more mutations of L234A, L235A, G237A, Y296Q, P329K, or any combination thereof. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, provided that the variant Fc polypeptide comprises one or more mutations of L234A, L235A, G237A, Y296Q, P329K, or any combination thereof. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, provided that the variant Fc polypeptide comprises one or more mutations of L234A, L235A, G237A, Y296Q, P329K, or any combination thereof. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, provided that the variant Fc polypeptide comprises one or more mutations of L234A, L235A, G237A, Y296Q, P329K, or any combination thereof. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, provided that the variant Fc polypeptide comprises one or more mutations of L234A, L235A, G237A, Y296Q, P329K, or any combination thereof. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, 20, 21, 22, 23, 24, or 25, provided that the variant Fc polypeptide comprises a set of mutations corresponding to L234A, L235A, G237A, Y296Q, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, provided that the variant Fc polypeptide comprises a set of mutations corresponding to L234A, L235A, G237A, Y296Q, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, provided that the variant Fc polypeptide comprises a set of mutations corresponding to L234A, L235A, G237A, Y296Q, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, provided that the variant Fc polypeptide comprises a set of mutations corresponding to L234A, L235A, G237A, Y296Q, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, provided that the variant Fc polypeptide comprises a set of mutations corresponding to L234A, L235A, G237A, Y296Q, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, provided that the variant Fc polypeptide comprises a set of mutations corresponding to L234A, L235A, G237A, Y296Q, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, provided that the variant Fc polypeptide comprises a set of mutations corresponding to L234A, L235A, G237A, Y296Q, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, provided that the variant Fc polypeptide comprises a set of mutations corresponding to L234A, L235A, G237A, Y296Q, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, 20, 21, 22, 23, 24, or 25, provided that the variant Fc polypeptide comprises a set of mutations corresponding to L234A, L235A, G237A, D265K, E269S, Y296Q, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, provided that the variant Fc polypeptide comprises a set of mutations corresponding to L234A, L235A, G237A, D265K, E269S, Y296Q, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, provided that the variant Fc polypeptide comprises a set of mutations corresponding to L234A, L235A, G237A, D265K, E269S, Y296Q, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, provided that the variant Fc polypeptide comprises a set of mutations corresponding to L234A, L235A, G237A, D265K, E269S, Y296Q, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, provided that the variant Fc polypeptide comprises a set of mutations corresponding to L234A, L235A, G237A, D265K, E269S, Y296Q, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, provided that the variant Fc polypeptide comprises a set of mutations corresponding to L234A, L235A, G237A, D265K, E269S, Y296Q, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, provided that the variant Fc polypeptide comprises a set of mutations corresponding to L234A, L235A, G237A, D265K, E269S, Y296Q, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, provided that the variant Fc polypeptide comprises a set of mutations corresponding to L234A, L235A, G237A, D265K, E269S, Y296Q, and P329K mutations.

In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, 20, 21, 22, 23, 24, or 25, provided that the variant Fc polypeptide comprises a set of mutations corresponding to L234A, L235A, G237A, D265K, E269S, Y296Q, S298K, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, provided that the variant Fc polypeptide comprises a set of mutations corresponding to L234A, L235A, G237A, D265K, E269S, Y296Q, S298K, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, provided that the variant Fc polypeptide comprises a set of mutations corresponding to L234A, L235A, G237A, D265K, E269S, Y296Q, S298K, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, provided that the variant Fc polypeptide comprises a set of mutations corresponding to L234A, L235A, G237A, D265K, E269S, Y296Q, S298K, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, provided that the variant Fc polypeptide comprises a set of mutations corresponding to L234A, L235A, G237A, D265K, E269S, Y296Q, S298K, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, provided that the variant Fc polypeptide comprises a set of mutations corresponding to L234A, L235A, G237A, D265K, E269S, Y296Q, S298K, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, provided that the variant Fc polypeptide comprises a set of mutations corresponding to L234A, L235A, G237A, D265K, E269S, Y296Q, S298K, and P329K mutations. In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, provided that the variant Fc polypeptide comprises a set of mutations corresponding to L234A, L235A, G237A, D265K, E269S, Y296Q, S298K, and P329K mutations.

In some embodiments, a variant Fc polypeptide comprises a mutation set of L234A, L235A, G237A, Y296Q, and P329K as compared to SEQ ID NO: 19, 20, 21, 22, 23, 24, or 25, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, Y296Q, and P329K mutation set as compared to SEQ ID NO: 19, 20, 21, 22, 23, 24, or 25. In some embodiments, a variant Fc polypeptide comprises a mutation set of L234A, L235A, G237A, Y296Q, and P329K as compared to SEQ ID NO: 19, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, Y296Q, and P329K mutation set as compared to SEQ ID NO: 19. In some embodiments, a variant Fc polypeptide comprises a mutation set of L234A, L235A, G237A, Y296Q, and P329K as compared to SEQ ID NO: 20, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, Y296Q, and P329K mutation set as compared to SEQ ID NO: 20. In some embodiments, a variant Fc polypeptide comprises a mutation set of L234A, L235A, G237A, Y296Q, and P329K as compared to SEQ ID NO: 21, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, Y296Q, and P329K mutation set as compared to SEQ ID NO: 21. In some embodiments, a variant Fc polypeptide comprises a mutation set of L234A, L235A, G237A, Y296Q, and P329K as compared to SEQ ID NO: 22, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, Y296Q, and P329K mutation set as compared to SEQ ID NO: 22. In some embodiments, a variant Fc polypeptide comprises a mutation set of L234A, L235A, G237A, Y296Q, and P329K as compared to SEQ ID NO: 23, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, Y296Q, and P329K mutation set as compared to SEQ ID NO: 23. In some embodiments, a variant Fc polypeptide comprises a mutation set of L234A, L235A, G237A, Y296Q, and P329K as compared to SEQ ID NO: 24, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, Y296Q, and P329K mutation set as compared to SEQ ID NO: 24. In some embodiments, a variant Fc polypeptide comprises a mutation set of L234A, L235A, G237A, Y296Q, and P329K as compared to SEQ ID NO: 25, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, Y296Q, and P329K mutation set as compared to SEQ ID NO: 25. In some embodiments, a variant Fc polypeptide comprises a mutation set of L234A, L235A, G237A, D265K, E269S, Y296Q, and P329K as compared to SEQ ID NO: 19, 20, 21, 22, 23, 24, or 25, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, D265K, E269S, Y296Q, and P329K mutation set as compared to SEQ ID NO: 19, 20, 21, 22, 23, 24, or 25. In some embodiments, a variant Fc polypeptide comprises a mutation set of L234A, L235A, G237A, D265K, E269S, Y296Q, and P329K as compared to SEQ ID NO: 19, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, D265K, E269S, Y296Q, and P329K mutation set as compared to SEQ ID NO: 19. In some embodiments, a variant Fc polypeptide comprises a mutation set of L234A, L235A, G237A, D265K, E269S, Y296Q, and P329K as compared to SEQ ID NO: 20, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, D265K, E269S, Y296Q, and P329K mutation set as compared to SEQ ID NO: 20. In some embodiments, a variant Fc polypeptide comprises a mutation set of L234A, L235A, G237A, D265K, E269S, Y296Q, and P329K as compared to SEQ ID NO: 21, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, D265K, E269S, Y296Q, and P329K mutation set as compared to SEQ ID NO: 21. In some embodiments, a variant Fc polypeptide comprises a mutation set of L234A, L235A, G237A, D265K, E269S, Y296Q, and P329K as compared to SEQ ID NO: 22, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, D265K, E269S, Y296Q, and P329K mutation set as compared to SEQ ID NO: 22. In some embodiments, a variant Fc polypeptide comprises a mutation set of L234A, L235A, G237A, D265K, E269S, Y296Q, and P329K as compared to SEQ ID NO: 23, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, D265K, E269S, Y296Q, and P329K mutation set as compared to SEQ ID NO: 23. In some embodiments, a variant Fc polypeptide comprises a mutation set of L234A, L235A, G237A, D265K, E269S, Y296Q, and P329K as compared to SEQ ID NO: 24, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, D265K, E269S, Y296Q, and P329K mutation set as compared to SEQ ID NO: 24. In some embodiments, a variant Fc polypeptide comprises a mutation set of L234A, L235A, G237A, D265K, E269S, Y296Q, and P329K as compared to SEQ ID NO: 25, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, D265K, E269S, Y296Q, and P329K mutation set as compared to SEQ ID NO: 25.

In some embodiments, a variant Fc polypeptide comprises a mutation set of L234A, L235A, G237A, D265K, E269S, Y296Q, S298K, and P329K as compared to SEQ ID NO: 19, 20, 21, 22, 23, 24, or 25, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, D265K, E269S, Y296Q, S298K, and P329K mutation set as compared to SEQ ID NO: 19, 20, 21, 22, 23, 24, or 25. In some embodiments, a variant Fc polypeptide comprises a mutation set of L234A, L235A, G237A, D265K, E269S, Y296Q, S298K, and P329K as compared to SEQ ID NO: 19, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, D265K, E269S, Y296Q, S298K, and P329K mutation set as compared to SEQ ID NO: 19. In some embodiments, a variant Fc polypeptide comprises a mutation set of L234A, L235A, G237A, D265K, E269S, Y296Q, S298K, and P329K as compared to SEQ ID NO: 20, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, D265K, E269S, Y296Q, S298K, and P329K mutation set as compared to SEQ ID NO: 20. In some embodiments, a variant Fc polypeptide comprises a mutation set of L234A, L235A, G237A, D265K, E269S, Y296Q, S298K, and P329K as compared to SEQ ID NO: 21, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, D265K, E269S, Y296Q, S298K, and P329K mutation set as compared to SEQ ID NO: 21. In some embodiments, a variant Fc polypeptide comprises a mutation set of L234A, L235A, G237A, D265K, E269S, Y296Q, S298K, and P329K as compared to SEQ ID NO: 22, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, D265K, E269S, Y296Q, S298K, and P329K mutation set as compared to SEQ ID NO: 22. In some embodiments, a variant Fc polypeptide comprises a mutation set of L234A, L235A, G237A, D265K, E269S, Y296Q, S298K, and P329K as compared to SEQ ID NO: 23, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, D265K, E269S, Y296Q, S298K, and P329K mutation set as compared to SEQ ID NO: 23. In some embodiments, a variant Fc polypeptide comprises a mutation set of L234A, L235A, G237A, D265K, E269S, Y296Q, S298K, and P329K as compared to SEQ ID NO: 24, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, D265K, E269S, Y296Q, S298K, and P329K mutation set as compared to SEQ ID NO: 24. In some embodiments, a variant Fc polypeptide comprises a mutation set of L234A, L235A, G237A, D265K, E269S, Y296Q, S298K, and P329K as compared to SEQ ID NO: 25, wherein the variant Fc polypeptide further comprises at least, about, or exactly 1-10, 1-20, 1, 2, 3, 4, 5, 6, 7, 8, 9, 10, 11, 12, 13, 14, 15, 16, 17, 18, 19 or 20 mutations in addition to the L234A, L235A, G237A, D265K, E269S, Y296Q, S298K, and P329K mutation set as compared to SEQ ID NO: 25.

In some embodiments, a variant Fc polypeptide comprises an amino acid sequence as provided in Table 3. In some embodiments, a variant Fc polypeptide comprises an amino acid sequence of SEQ ID NO: 19, 20, 21, 22, 23, 24, 25, 42, 43, 44, 45, 46, 47, 48, or 49. In some embodiments, a variant Fc polypeptide comprises an amino acid sequence of SEQ ID NO: 19. In some embodiments, a variant Fc polypeptide comprises an amino acid sequence of SEQ ID NO: 20. In some embodiments, a variant Fc polypeptide comprises an amino acid sequence of SEQ ID NO: 21. In some embodiments, a variant Fc polypeptide comprises an amino acid sequence of SEQ ID NO: 22. In some embodiments, a variant Fc polypeptide comprises an amino acid sequence of SEQ ID NO: 23. In some embodiments, a variant Fc polypeptide comprises an amino acid sequence of SEQ ID NO: 24. In some embodiments, a variant Fc polypeptide comprises an amino acid sequence of SEQ ID NO: 25. In some embodiments, a variant Fc polypeptide comprises an amino acid sequence of SEQ ID NO: 42. In some embodiments, a variant Fc polypeptide comprises an amino acid sequence of SEQ ID NO: 43. In some embodiments, a variant Fc polypeptide comprises an amino acid sequence of SEQ ID NO: 44. In some embodiments, a variant Fc polypeptide comprises an amino acid sequence of SEQ ID NO: 45. In some embodiments, a variant Fc polypeptide comprises an amino acid sequence of SEQ ID NO: 46. In some embodiments, a variant Fc polypeptide comprises an amino acid sequence of SEQ ID NO: 47. In some embodiments, a variant Fc polypeptide comprises an amino acid sequence of SEQ ID NO: 48. In some embodiments, a variant Fc polypeptide comprises an amino acid sequence of SEQ ID NO: 49.

In some embodiments, a variant Fc polypeptide comprises an amino acid sequence having a C-terminal lysine (K). In some embodiments, a variant Fc polypeptide comprises an amino acid sequence not having a C-terminal lysine (K).

In some embodiments, the variant Fc polypeptide, such as those provided herein, is conjugated to another polypeptide. In some embodiments, the another polypeptide is an antibody. In some embodiments, the variant Fc polypeptide, such as those provided herein, is conjugated to an effector binding/modulating polypeptide or a tissue targeting polypeptide. In some embodiments, the variant Fc polypeptide, such as those provided herein, is conjugated to an antibody, or antigen-binding fragment thereof. In some embodiments, the variant Fc polypeptide, such as those, is conjugated to another polypeptide via a linker or a covalent bond. In some embodiments, the linker is a protein linker, such as those provided herein.

Polypeptides Having Protease Activity

The present disclosure provides for polypeptides, molecules, compounds, therapeutics, and compositions comprising a polypeptide having protease activity, which can be covalently or non-covalently connected to a Fc polypeptide domain, such as those provided for herein. In some embodiments, the polypeptide having protease activity is IdeS, IdeSsuis, IdeZ, IdeE, IdeE2, IdeZ2, or IdeC.

*Streptococcus pyogenes* is a significant bacterial pathogen that secretes two enzymes showing remarkable specificity for IgG; EndoS and IdeS. EndoS (Endoglycosidase in *Streptococcus pyogenes*) specifically hydrolyzes the functionally important N-linked glycan of IgG, and treatment with EndoS abrogates the pathogenic activity of IgG in mouse models of autoimmune disease. (Collin M, Olsen A. EndoS, a novel secreted protein from *Streptococcus pyogenes* with endoglycosidase activity on human IgG. Embo J. 2001; 20:3046-3055; Nandakumar K S, Collin M, Olsen A, Nimmerjahn F, Blom A M, et al. Endoglycosidase treatment abrogates IgG arthritogenicity: importance of IgG glycosylation in arthritis. Eur J Immunol. 2007; 37:2973-2982) IdeS (Immunoglobulin G-degrading enzyme of *Streptococcus pyogenes*) is a cysteine proteinase which cleaves IgG with a unique degree of specificity in the hinge region. (Wenig K, Chatwell L, von Pawel-Rammingen U, Björck L, Huber R, et al. Structure of the streptococcal endopeptidase IdeS, a cysteine proteinase with strict specificity for IgG. Proc Natl Acad Sci USA. 2004; 101:17371-17376) IdeS is extremely specific for IgG, which is hydrolyzed in the hinge region after glycine residue 236 in both heavy chains, which generates one F(ab')2 and two monomeric Fc fragments. IdeE is a homolog of the secreted IgG-specific protease IdeS/Mac of *Streptococcus pyogenes*. The activity of IdeE is comparable with the activity of IdeZ, the corresponding enzyme of the closely related *S. equi* ssp. *zooepidemicus*.

The full sequence of IdeS is publically available as NCBI Reference Sequence no. WP_010922160.1 and is provided herein as SEQ ID NO: 35:

(SEQ ID NO: 35)
MRKRCYSTSAAVLAAVTLFVLSVDRGVIADSFSANQEIRYSEVTPYHVT

SVWTKGVTPPANFTQGEDVFHAPYVANQGWYDITKTFNGKDDLLCGAAT

AGNMLHWWFDQNKDQIKRYLEEHPEKQKINFNGEQMFDVKEAIDTKNHQ

LDSKLFEYFKEKAFPYLSTKHLGVFPDHVIDMFINGYRLSLINHGPTPV

KEGSKDPRGGIFDAVFTRGDQSKLLTSRHDFKEKNLKEISDLIKKELTE

GKALGLSHTYANVRINHVINLWGADFDSNGNLKAIYVIDSDSNASIGMK

KYFVGVNSAGKVAISAKEIKEDNIGAQVLGLFTLSTGQDSWNQIN.

This sequence includes an N-terminus methionine followed by a 28 amino acid secretion signal sequence. The N-terminus methionine and the signal sequence (a total of 29 amino acids at the N terminus) are typically removed to form the mature IdeS protein, the amino acid sequence of which is publically available as UniProt Identifier Q9F1R7_STRPY and is provided herein as SEQ ID NO: 36.

IdeZ is an IgG cysteine protease produced by *Streptococcus equi* ssp. *zooepidemicus*, a bacterium predominantly found in horses. As IdeZ is not a human pathogen, human subjects do not typically have antibodies against this protein in their plasma. However, IdeZ has a level of IgG cysteine protease activity against human IgG which is considerably lower than that of IdeS. The mature sequence of IdeZ is publically available as UniProt Identifier A0A0D0YKS5_STRSZ and is provided herein as SEQ ID NO: 37.

In some embodiments, the polypeptide having protease activity is IdeS, IdeSsuis, IdeZ, IdeE, IdeE2, IdeZ2, or IdeC. In some embodiments, the IdeS, IdeZ, IdeE, IdeE2, IdeZ2, or IdeC protease has an amino acid sequence such as those provided herein. The mature sequence of IdeSsuis is publically available as UniProt Identifier C5W022 and is provided herein as SEQ ID NO: 55. The mature sequence of IdeE is publically available as UniProt Identifier COM8U6_STRE4 and is provided herein as SEQ ID NO: 38. The mature sequence of IdeE2 is publically available as UniProt Identifier C7B615_9STRE and is provided herein as SEQ ID NO: 39. The mature sequence of IdeZ2 is publically available as UniProt Identifier B4U2F7_STREM and is provided herein as SEQ ID NO: 40. The mature sequence of IdeC is publically available as UniProt Identifier A0A3P5YAY8_STRCB and is provided herein as SEQ ID NO: 41. In some embodiments, the protease is an IgG degrading protease. In some embodiments, the protease is an IgM degrading protease.

TABLE 4

| ID | Polypeptide having protease activity Seq |
|---|---|
| IdeS | ANQEIRYSEVTPYHVTSVWTKGVTPPAQFTQGEDVFHAPYVANQGWYDITKTFNGKDDLLCGAATAG NMLHWWFDQNKDQIKRYLEEHPEKQKINFNGEQMEDVKEAIDTKNHQLDSKLFEYFKEKAFPYLSTK HLGVFPDHVIDMFINGYRLSLINHGPTPVKEGSKDPRGGIFDAVETRGDQSKLLTSRHDFKEKNLKE ISDLIKKELTEGKALGLSHTYANVRINHVINLWGADFDSNGNLKAIYVTDSDSNASIGMKKYFVGVN SAGKVAISAKEIKEDNIGAQVLGLFTLSTGQDSWNQTN (SEQ ID NO: 26) |
| IdeS-Glycan | ANQEIRYSEVTPYHVISVWTKNVTPPAQFTQGEDVFHAPYVANQGWYDITKTFNGKDDLLCGAATAG NMLHWWFDQNKDQIKRYLEEHPEKQKINFNGSQMFDVKEAIDTKNHQLDSKLFEYFKEKAFPYLSTK HLGVFPDHVIDMFINGYRLSLNNSGPTPVKNGSKDPRGGIFDAVFTRGDQSKLLTSRHDFKNKSLKE ISDLIKKELTEGKALGLSHTYANVRINHVINLWGADFDSNGTLKAIYVTDSDSNASIGMKKYFVGVN NATKVAISAKEIKENNTGAQVLGLFTLSTGQDSWNQTN (SEQ ID NO: 28) |
| IdeS-NAQ | ANQEIRYSEVTPYHVISVWTKGVTPPAQFTQGEDVFHAPYVANQGWYDITKTFNGKDDLLCGAATAG NMLHWWFDQNKDQIKRYLEEHPEKQKINFNGEQMEDVKEAIDTKNHQLDSKLFEYFKEKAFPYLSTK |

TABLE 4-continued

| ID | Polypeptide having protease activity Seq |
|---|---|
| | HLGVFPDHVIDMFINGYRLSLINHGPTPVKEGSKDPRGGIFDAVFTRGDQSKLLTSRHDFKEKNLKE ISDLIKKELTEGKALGLSHTYANVRINHVINLWGADFDSNGNLKAIYVTDSDSNAQIGMKKYFVGVN SAGKVAISAKEIKEDNIGAQVLGLFTLSTGQDSWNQTN (SEQ ID NO: 29) |
| IdeS-NAQ-G/S Linker | ANQEIRYSEVTPYHVTSVWTKGVTPPAQFTQGEDVFHAPYVANQGWYDITKTENGKDDLLCGAATAG NMLHWWFDQNKDQIKRYLEEHPEKQKINFNGEQMEDVKEAIDTKNHQLDSKLFEYFKEKAFPYLSTK HLGVFPDHVIDMFINGYRLSLINHGPTPVKEGSKDPRGGIFDAVFTRGDQSKLLTSRHDFKEKNLKE ISDLIKKELTEGKALGLSHTYANVRINHVINLWGADFDSNGNLKAIYVTDSDSNAQIGMKKYFVGVN SAGKVAISAKEIKEDNIGAQVLGLFTLSTGQDSWNQINGGGGS (C-terminus) (SEQ ID NO: 31) |
| IdeS | ANQEIRYSEVTPYHVTSVWTKGVTPPANFTQGEDVFHAPYVANQGWYDITKTFNGKDDLLCGAATAG NMLHWWFDQNKDQIKRYLEEHPEKQKINFNGEQMEDVKEAIDTKNHQLDSKLFEYFKEKAFPYLSTK HLGVFPDHVIDMFINGYRLSLINHGPTPVKEGSKDPRGGIFDAVFTRGDQSKLLTSRHDFKEKNLKE ISDLIKKELTEGKALGLSHTYANVRINHVINLWGADFDSNGNLKAIYVTDSDSNASIGMKKYFVGVN SAGKVAISAKEIKEDNIGAQVLGLFTLSTGQDSWNQTN (SEQ ID NO: 36) |
| IdeS-Glycan N42 | ANQEIRYSNVTPYHVTSVWTKGVTPPANFTQGEDVFHAPYVANQGWYDITKTFNGKDDLLCGAATAG NMLHWWFDQNKDQIKRYLEEHPEKQKINFNGEQMEDVKEAIDTKNHQLDSKLFEYFKEKAFPYLSTK HLGVFPDHVIDMFINGYRLSLINHGPTPVKEGSKDPRGGIFDAVETRGDQSKLLTSRHDFKEKNLKE ISDLIKKELTEGKALGLSHTYANVRINHVINLWGADFDSNGNLKAIYVTDSDSNASIGMKKYFVGVN SAGKVAISAKEIKEDNIGAQVLGLFTLSTGQDSWNQTN (SEQ ID NO: 50) |
| IdeS-Glycan N47N274 | ANQEIRYSEVTPYHNTSVWTKGVTPPANFTQGEDVFHAPYVANQGWYDITKTFNGKDDLLCGAATAG NMLHWWFDQNKDQIKRYLEEHPEKQKINFNGEQMEDVKEAIDTKNHQLDSKLFEYFKEKAFPYLSTK HLGVFPDHVIDMFINGYRLSLINHGPTPVKEGSKDPRGGIFDAVETRGDQSKLLTSRHDFKEKNLKE ISDLIKKELTEGKALGLSHTYANVRINHVINLWGADFDSNGSLKAIYVTDSDSNASIGMKKYFVGVN SAGKVAISAKEIKEDNIGAQVLGLFTLSTGQDSWNQTN (SEQ ID NO: 51) |
| IdeS suis | DTVVTGVNEIIEESQVKDEVSIESEKNESLDGSNIEIVEEIADNIPSPVIAEGEVAVEMKVDRGTEN VVSRNDTEVTTSEQNQIEVTETKEILNQTSYQTESGEQRQIIWAHGITPPAMEQSGGFVKEKYGDYL NYTAPFEAGKGYYDTNKSLNASFIDLNLCFAAVSSNMVHWWLEQNSSYVERYLKEKKGTVNVEENYA ITDLRRYINSFQNQQNSRVFDMFKTYYGYRINGFVSDALVDLFINGYKPKAQGGVNLEDSQLVPDSR GGFFYDVFKEKKLINRIFSGSYERFGEDVRTVLESKGLLGLTYRTLGYATHIVTVWGAEYDNQGKIK AVYITDSDDQQEQIGLKRMGITRDASGNPRLNNHMKNNSAGALLDYVHTIRLGQDLWEEYENPLAKA KETASQTLADTKKALDLSIQGQSELPESMRLIYLEKLNNLYNQGILSIQKAESSEMLSGALENGINS LKSLDFPISEVGNALAPDLPVGDRSTVSDVDSLSSQETSSTNLEADTENAGIIADGTNQLHFPVEAQ TTSSVEAEGDNVFEQEADILPIIIENKDEFGSELSRNMQTSETDSLVVAVEEDVKNDEVAQVEELLE SEKVENQSSELLSDTLIVESANDKEEDRVEAVVSEQPDSIPHQNVEISLVEPTNVETETVVTPINDA ATPHGSPTYIDNSVTESVATPLEKDSIQAGETEIAEPTSSESTNVETETVVTPVNDVATPHGSPTYI DNSVTESVATPLEKDSIQAGETEIAEPTSSESTSVEAELVDNSEIHAATSSVTPCGSSAYADGSTTESVATPLEKDS IQTGNTEIAEPTSSKSTNVEAASVDNSEIHADASLTAVSSVNLDNPVIEPVAISLIGSKRDTNAEVE VSSLSKREVRKTNTDGLISVQSKVIKKELLESSLAEAGSPLLEATIAQSSNSNSTEIGMSYQNTVLL ESNNTERQVSKAEIVMEHKETELVETVSSASEPVVLVENISQTSNNTIESGKNMGVQSQAGAKQILG VEQSSKVSTPTSRQIMGVGLLTLVLGSALGLLKKRRK (SEQ ID NO: 55) |
| IdeE | DDYQRNATEAYAKEVPHQITSVWTKGVTPLTPEQFRYNNEDVIHAPYLAHQGWYDITKAFDGKDNLL CGAATAGNMLHWWFDQNKTEIEAYLSKHPEKQKIIFNNQELFDLKAAIDTKDSQTNSQLFNYFRDKA FPNLSARQLGVMPDLVLDMFINGYYLNVFKTQSTDVNRPYQDKDKRGGIFDAVETRGDQTTLLTARH DLKNKGLNDISTIIKQELTEGRALALSHTYANVSISHVINLWGADENAEGNLEAIYVTDSDANASIG MKKYFVGINAHRHVAISAKKIEGENIGAQVLGLFTLSSGKDIWQKLS (SEQ ID NO: 37) |
| IdeZ | DDYQRNATEAYAKEVPHQITSVWTKGVTPLTPEQFRYNNEDVIHAPYLAHQGWYDITKAFDGKDNLL CGAATAGNMLHWWFDQNKTEIEAYLSKHPEKQKIIFNNQELFDLKAAIDTKDSQTNSQLFNYFRDKA FPNLSARQLGVMPDLVLDMFINGYYLNVFKTQSTDVNRPYQDKDKRGGIFDAVETRGDQTTLLTARH DLKNKGLNDISTIIKQELTEGRALALSHTYANVSISHVINLWGADFNAEGNLEAIYVTDSDANASIG MKKYFVGINAHGHVAISAKKIEGENIGAQVLGLFTLSSGKDIWQKLS (SEQ ID NO: 38) |
| IdeZ-V2 | RNATEAYAKEVPHQITSVWTKGVTPLTPEQFRYNNEDVIHAPYLAHQGWYDITKAFDGKDNLLCGAA TAGNMLHWWFDQNKTEIEAYLSKHPEKQKIIFNNQELFDLKAAIDTKDSQTNSQLFNYFRDKAFPNL SARQLGVMPDLVLDMFINGYYLNVFKTQSTDVNRPYQDKDKRGGIFDAVETRGDQTTLLTARHDLKN KGLNDISTIIKQELTEGRALALSHTYANVSISHVINLWGADFNAEGNLEAIYVIDSDANASIGMKKY FVGINAHGHVAISAKKIEGENIGAQVLGLFTLSSGKDIWQKLS (SEQ ID NO: 52) |
| IdeE 2 | EVVEVWPNGQNPNGKIEILSQTEHSEHLQKLRDIEDFQAQKQADHVRYTKWLDGVTVDEHEFRKIKE YDTEYYVTPLLSGKGYYDINKDFNQDSDKCAAAVAANMFHYWFDRNRDSINRFLSQSPGENGVIKLE NEKTIEVSKFLETYRSDGDYLDKSPFFDLISNSFKGPVWANKLLDAYINGYGYIHKFAKNTPHSKNN NSKFNFFKKVFDGNLLTDIHQIFDYNTFSDKLSEALYTGKAIGLAYGPGDLRRSLGHIISVWGADLD DQNRVVAIYVTDSDDKKLTIGNERVGLKRYKVSSDDQGRARLTTRDKDNTGGEIRSIETLDMGTQEW ADYFNKTEK (SEQ ID NO: 39) |
| IdeZ 2 | EVVEVWPYGQNPNGKTEILSQTEDSESLQRLRDIEDFQAEKKMQNVVYTKWLDGVDVKDHDERKIVD GNIAYYATPLLNGRGFYDINKDFNRDSDKCAAAVAANMFHYWLDINRDNVDRFLRQNPEKHGIIELP DGQLKLSDFLNTYESDHGYRDKSKLFDFISNNFNGPVWTDKLLDNYINGYAYNYKYGRTIEDPTKNT SKINFFKEVFNEKILINNHSIRNQNEFSVLLSEALYTGKAIGLSYGPAGLRHSLGHIISVWGADLDA DGNVVAIYVTDSDDKKLTIGDERVGLKRYKISTDDENRLRLTAYEETHNTGQIRGLWILDTGKYAW ADYFDKTEQTGTDQAEQ (SEQ ID NO: 40) |

TABLE 4-continued

| ID | Polypeptide having protease activity Seq |
|---|---|
| IdeC | RNQITTYSEATPSHITSIWTKGVTPPTNFIEGTDGSHAPYIANQGWYDITKTFNGKDDLLCAAATAG<br>NMLHWWFDQNKNQIEGYLTEHPEKQAIIFNGEKMEDVKEAISTKDRQLDSKLFEYFKEKAFPTLSAR<br>RRGVFPDHVIDMFINGYRLSLDNYDKTPVKEGNKDLRGGIFDQVFTRGDQSKLLINRYNLRIKTINE<br>ISQLIKQELIAGKALAISHTYNNIGISHVINLWGADENSEGNLEAIYVTDSDSNASIGMKKYYVGVN<br>SAGEVAVSSKKIDSEHLGAAALGLYTLSAGQGIWHQTN (SEQ ID NO: 41) |

In some embodiments, a polypeptide having protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any sequence provided in Table 4. In some embodiments, the polypeptide having protease activity is IdeS. In some embodiments, the polypeptide having protease activity is IdeSsuis. In some embodiments, the polypeptide having protease activity is IdeE. In some embodiments, the polypeptide having protease activity is IdeZ. In some embodiments, the polypeptide having protease activity is IdeE2. In some embodiments, the polypeptide having protease activity is IdeZ2. In some embodiments, the polypeptide having protease activity is IdeC. In some embodiments, a polypeptide having protease activity comprises an amino acid sequence having at least 50%, 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, 28, 29, 31, 36, 37, 38, 39, 40, 41, 50, 51, 52, or 55. In some embodiments, a polypeptide having protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26. In some embodiments, a polypeptide having protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28. In some embodiments, a polypeptide having protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29. In some embodiments, a polypeptide having protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31. In some embodiments, a polypeptide having protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36. In some embodiments, a polypeptide having protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37. In some embodiments, a polypeptide having protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38. In some embodiments, a polypeptide having protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39. In some embodiments, a polypeptide having protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40. In some embodiments, a polypeptide having protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41. In some embodiments, a polypeptide having protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50. In some embodiments, a polypeptide having protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51. In some embodiments, a polypeptide having protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52. In some embodiments, a polypeptide having protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55.

In some embodiments, a polypeptide having protease activity comprises an amino acid sequence as provided in Table 4. In some embodiments, the polypeptide having protease activity is IdeS. In some embodiments, the polypeptide having protease activity is IdeSsuis. In some embodiments, the polypeptide having protease activity is IdeE. In some embodiments, the polypeptide having protease activity is IdeZ. In some embodiments, the polypeptide having protease activity is IdeE2. In some embodiments, the polypeptide having protease activity is IdeZ2. In some embodiments, the polypeptide having protease activity is IdeC. In some embodiments, a polypeptide having protease activity comprises an amino acid sequence of SEQ ID NO: 26, 28, 29, 31, 36, 37, 38, 39, 40, 41, 50, 51, 52, or 55. In some embodiments, a polypeptide having protease activity comprises an amino acid sequence of SEQ ID NO: 26. In some embodiments, a polypeptide having protease activity comprises an amino acid sequence of SEQ ID NO: 28. In some embodiments, a polypeptide having protease activity comprises an amino acid sequence of SEQ ID NO: 29. In some embodiments, a polypeptide having protease activity comprises an amino acid sequence of SEQ ID NO: 31. In some embodiments, a polypeptide having protease activity comprises an amino acid sequence of SEQ ID NO: 36. In some embodiments, a polypeptide having protease activity comprises an amino acid sequence of SEQ ID NO: 37. In some embodiments, a polypeptide having protease activity comprises an amino acid sequence of SEQ ID NO: 38. In some embodiments, a polypeptide having protease activity comprises an amino acid sequence of SEQ ID NO: 39. In some embodiments, a polypeptide having protease activity comprises an amino acid sequence of SEQ ID NO: 40. In some embodiments, a polypeptide having protease activity comprises an amino acid sequence of SEQ ID NO: 41. In some embodiments, a polypeptide having protease activity comprises an amino acid sequence of SEQ ID NO: 50. In some embodiments, a polypeptide having protease activity comprises an amino acid sequence of SEQ ID NO: 51. In some embodiments, a polypeptide having protease activity comprises an amino acid sequence of SEQ ID NO: 52. In some embodiments, a polypeptide having protease activity comprises an amino acid sequence of SEQ ID NO: 55.

In some embodiments, a polypeptide having protease activity comprises one or more mutations at one or more N-glycosylation sites. In some embodiments, a polypeptide having protease activity comprises one or more mutations at one or more N-glycosylation sites that disrupt N-glycosylation. In some embodiments, a polypeptide having protease activity comprises one or more mutations at one or more N-glycosylation sites that prevent or inhibit N-glycosylation. In some embodiments, a polypeptide having protease activity comprises one or more mutations at one or more N-glycosylation sites that render the polypeptide having protease activity resistant to N-glycosylation. In some embodiments, the protease is IdeS. In some embodiments, the protease is IdeSsuis. In some embodiments, the protease is IdeE. In some embodiments, the protease is IdeZ. In some embodiments, the protease is IdeE2. In some embodiments, the protease is IdeZ2. In some embodiments, the protease is IdeC. In some embodiments, the IdeS protease comprises a mutation at one or more N-glycosylation sites. In some embodiments, the IdeS protease comprises a mutation at one or more of positions 42, 47, 61, 62, 63, 274, 288, 289, 290, 336, 337, 338, or any combination thereof.

In some embodiments, the IdeS protease comprises a mutation at one or more of positions 61, 62, 63, or any combination thereof. In some embodiments, the IdeS protease comprises a mutation at one or more of positions 288, 289, 290, or any combination thereof. In some embodiments, the IdeS protease comprises a mutation at one or more of positions 336, 337, 338, or any combination thereof. In some embodiments, the IdeS protease comprises a mutation at one or more of positions 61, 62, 63, 288, 289, 290, or any combination thereof. In some embodiments, the IdeS protease comprises a mutation at one or more of positions 61, 62, 63, 336, 337, 338, or any combination thereof. In some embodiments, the IdeS protease comprises a mutation at one or more of positions 336, 337, 338, or any combination thereof. In some embodiments, the IdeS protease comprises a mutation at one or more of positions 61, 288, 290, 336, or any combination thereof.

In some embodiments, the IdeS protease comprises a mutation at position 61. In some embodiments, the IdeS protease comprises a mutation at position 288. In some embodiments, the IdeS protease comprises a mutation at position 336. In some embodiments, the IdeS protease comprises a mutation at position 290. In some embodiments, the IdeS protease comprises a mutation at position N42. In some embodiments, the IdeS protease comprises a mutation at position N47. In some embodiments, the IdeS protease comprises a mutation at position N274. In some embodiments, the IdeS protease comprises a mutation at position N47 and N274. In some embodiments, the IdeS protease comprises a mutation at position N61. In some embodiments, the IdeS protease comprises a mutation at position N288. In some embodiments, the IdeS protease comprises a mutation at position S290. In some embodiments, the IdeS protease comprises a mutation at position N336. In some embodiments, the IdeS protease comprises a mutation at position N61 and S290. In some embodiments, the IdeS protease comprises a mutation at position N61 and N288. In some embodiments, the IdeS protease comprises a mutation at position N61 and N336. In some embodiments, the IdeS protease comprises a mutation at position N288 and N336. In some embodiments, the IdeS protease comprises a mutation at position S290 and N336.

In some embodiments, the protease comprises an amino acid sequence that comprises a signal sequence. In some embodiments, the protease comprises an amino acid sequence that does not comprise a signal sequence. In some embodiments, the signal sequence can have the amino acid sequence of METDTLLLWVLLLWVPGSTG (SEQ ID NO: 53), or MNIQERFSLRKSAVGLVSVSLLCAIYTSTVAA (SEQ ID NO: 54).

In some embodiments, the polypeptide having IgG protease activity is as effective, or more effective at cleaving IgG than the wild-type protease, and/or is less immunogenic, or as immunogenic, as the wild-type protease. In some embodiments, the polypeptide having IgG protease activity is as effective at cleaving IgG than the wild-type protease. In some embodiments, the polypeptide having IgG protease activity is more effective at cleaving IgG than the wild-type protease. In some embodiments, the polypeptide having IgG protease activity is less immunogenic than the wild-type protease. In some embodiments, the polypeptide having IgG protease activity is as immunogenic as the wild-type protease.

Fc Fusion Molecules

Provided herein are therapeutic compounds, e.g., therapeutic protein molecules, e.g., fusion proteins, including an effector binding/modulating moiety and a polypeptide having protease activity. Also provided are methods of using and making the therapeutic compounds. In some embodiments, the effector binding/modulating moiety is a variant Fc polypeptide, such as, but not limited to, those provided herein.

The disclosure provides for, for example, a polypeptide comprising a polypeptide having protease activity and a Fc polypeptide domain, wherein the polypeptide having protease activity is covalently or non-covalently connected to the Fc polypeptide domain. In some embodiments, the Fc polypeptide domain is a variant Fc polypeptide, such as those provided herein. Accordingly, in some embodiments, a polypeptide comprising a polypeptide having protease activity and a Fc polypeptide domain is provided, wherein the polypeptide having protease activity is covalently or non-covalently connected to the Fc polypeptide, is provided. The polypeptide having protease activity can be fused or linked (i.e., conjugated) to the Fc polypeptide. In some embodiments, the polypeptide having protease activity is non-covalently associated with the Fc polypeptide domain. In some embodiments, the protease is an IgG protease. In some embodiments, the protease is an IdeS, IdeSsuis, IdeE, IdeZ, IdeZ2, IdeE2, or IdeC protease, or a variant thereof. A variant of such protease is one that has at least one mutation, insertion, or deletion as compared to the wild-type sequence. Examples of such proteases, or variants thereof, include those provided for in U.S. Pat. Nos. 11,524,057, 10,696,959, 11,667,905, 11,214,784, 10,758,597, U.S. Patent Application Publication No. 20200345844, U.S. Patent Application Publication No. 20210260173, U.S. Patent Application Publication No. 20230357741, U.S. Patent Application Publication No. 20230302100, U.S. Patent Application Publication No. 20220133864, U.S. Pat. No. 8,133,483, PCT Publication No. WO2023175498, EP Patent No. EP3256580, EP Patent No. EP3256579, each of which are hereby incorporated by reference in entirety.

In some embodiments, the Fc polypeptide domain is an IgG Fc polypeptide, such as a Fc polypeptide that is, or derived from an IgG1, IgG2, IgG3, or IgG4 Fc polypeptide. In some embodiments, the Fc polypeptide domain is a variant Fc polypeptide domain, such as the variants provided for herein. In some embodiments, the Fc polypeptide domain is protease resistant. The Fc polypeptide can be resistant to protease to which it is connected to, thus resistant to protease cleavage and/or binding by the protease. In some embodiments, the variant Fc polypeptide, such as those provided herein, comprises a mutation that renders the IgG Fc polypeptide resistant to cleavage by a protease, or a variant thereof. In some embodiments, the variant Fc polypeptide, such as those provided herein, comprises a mutation that renders the IgG Fc polypeptide resistant to binding by a protease, or a variant thereof. In some embodiments, the variant Fc polypeptide, such as those provided herein, comprises a set of mutations that render the IgG Fc polypeptide resistant to cleavage by a protease, or a variant thereof. In some embodiments, the variant Fc polypeptide, such as those provided herein, comprises a set of mutations that render the IgG Fc polypeptide resistant to binding by a protease, or a variant thereof. In some embodiments, the variant Fc polypeptide, such as those provided herein, comprises a mutation that renders the IgG Fc polypeptide resistant to cleavage by a protease, or a variant thereof, and/or binding by a protease, or a variant thereof. In some embodiments, the variant Fc polypeptide, such as those provided herein, comprises a set of mutations that render the IgG Fc polypeptide resistant to cleavage by a protease, or a variant thereof, and/or binding by a protease, or a variant thereof. In some embodiments, the variant Fc polypeptide, such as those provided herein, is resistant to cleavage by a protease, or a variant thereof. In some embodiments, the variant Fc polypeptide, such as those provided herein, is resistant to binding by a protease, or a variant thereof. In some embodiments, the variant Fc polypeptide, such as those provided herein, is resistant to cleavage by a protease, or a variant thereof, and/or binding by a protease, or a variant thereof. It can also be resistant to other proteases that the Fc polypeptide domain is not connected to. Fc polypeptides can self-associate with one another to form a dimer. The dimer may be a homodimer where the Fc polypeptide is the same in each polypeptide molecule or may be a heterodimer where the Fc polypeptide is different in each polypeptide molecule that forms the dimer.

In some embodiments, the variant Fc polypeptide is covalently or non-covalently conjugated to a polypeptide having IgG protease activity, wherein the polypeptide having IgG protease activity can be conjugated to N-terminus or C-terminus of the variant Fc polypeptide. In some embodiments, the variant Fc polypeptide is covalently or non-covalently conjugated to a polypeptide having IgG protease activity, wherein the polypeptide having IgG protease activity can be conjugated to the N-terminus of the variant Fc polypeptide. In some embodiments, the variant Fc polypeptide is covalently or non-covalently conjugated to a polypeptide having IgG protease activity, wherein the polypeptide having IgG protease activity can be conjugated to the C-terminus of the variant Fc polypeptide.

The Fc polypeptide and the polypeptide having protease activity can be physically tethered, covalently or non-covalently, directly or through a linker entity, to one another, e.g., as a domain of the same linear primary amino acid sequence in a single polypeptide. The polypeptides can associate with one another through the Fc polypeptide, such that a dimer is created having a first and second polypeptide. In some embodiments, the first polypeptide comprises a polypeptide having protease activity linked to a Fc polypeptide domain. In some embodiments, the second polypeptide comprises a Fc polypeptide domain, such as those provided for herein. In some embodiments, the second polypeptide does not comprise a protease domain. In some embodiments, the second polypeptide comprises a protease domain.

This multi-domain molecule can be referred to as a therapeutic protein molecule. In some embodiments, the protease and the IgG Fc molecule are provided in a therapeutic protein molecule, e.g., a fusion protein.

In some embodiments, polypeptide comprising the polypeptide having protease activity, the Fc polypeptide domain, which can be a variant Fc polypeptide, or both further comprises a single domain antibody molecule, e.g., a nanobody, a camelid antibody VHH molecule or human soluble VH domain. Without wishing to be bound to any particular theory, the nanobody covalently or non-covalently conjugated to the polypeptide comprising a polypeptide having a protease activity and/or an Fc polypeptide may extend the half-life of the polypeptide. In some embodiments, the single domain antibody molecule, e.g., a nanobody, a camelid antibody VHH molecule or human soluble VH domain is physically tethered, covalently or non-covalently, directly or through a linker entity, to the polypeptide having protease activity, the variant Fc polypeptide, or both. In some embodiments, the variant Fc polypeptide may also contain a single-chain fragment variable (scFv) or a Fab domain. In some embodiments, the therapeutic protein molecule, or a nucleic acid, e.g., an mRNA or DNA, encoding the therapeutic protein molecule, can be administered to a subject. In some embodiments, the polypeptide having protease activity and the variant Fc polypeptide are linked to a third entity, e.g., a carrier, e.g., a polymeric carrier, a dendrimer, or a particle, e.g., a nanoparticle. As used herein, the terms "nanobody." and "VHH" can be used interchangeably.

Non-limiting examples of nanobodies include those provided in McMahon et al., Nat Struct Mol Biol. 2018 March; 25(3): 289-296. doi: 10.1038/s41594-018-0028-6; which is hereby incorporated by reference in its entirety. In some embodiments, the nanobody, or the VHH comprises an amino acid sequence as set in Table 5.

TABLE 5

| ID | VHH Seq |
|---|---|
| VHH-1 | QVQLQESGGGLVQAGGSLRLSCAASGYISDAYYMGWYRQAPGKEREFVATITHGTNTYYADSVKGRFTISRDNAKNTVYLQMNSLKPEDTAVYYCAVLETRSYSFRYWGQGTQVTVSSLEGGGGS (SEQ ID NO: 30) |
| VHH-2 | QVQLQESGGGLVQAGGSLRLSCAASGYISDAYYMGWYRQAPGKEREFVATITHGINTYYADSVKGRFTISRDNAKNTVYLQMNSLKPEDTAVYYCAVLETRSYSFRYWGQGTQVTVSSLEGG (SEQ ID NO: 32) |
| VHH-3 | QVQLQESGGGLVQAGGSLRLSCAASGYISDAYYMGWYRQAPGKEREFVATITHGINTYYADSVKGRFTISRDNAKNTVYLQMNSLKPEDTAVYYCAVLETRSYSFRYWGQGTQVTVSSLE (SEQ ID NO: 33) |

In some embodiments, a nanobody comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to any sequence provided in Table 5. In some embodiments, a nanobody comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 30, 32, or 33. In some embodiments, a nanobody comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 30. In some embodiments, a nanobody comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 32. In some embodiments, a nanobody comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 33.

In some embodiments, a nanobody comprises an amino acid sequence having an amino acid sequence of SEQ ID NO: 30, 32, or 33. In some embodiments, a nanobody comprises an amino acid sequence having an amino acid sequence of SEQ ID NO: 30. In some embodiments, a nanobody comprises an amino acid sequence having an amino acid sequence of SEQ ID NO: 32. In some embodiments, a nanobody comprises an amino acid sequence having an amino acid sequence of SEQ ID NO: 33.

In some embodiments, a therapeutic compound or compound comprises a polypeptide comprising a polypeptide having protease activity covalently or non-covalently conjugated to a variant Fc polypeptide. In some embodiments, a therapeutic molecule comprises a fusion protein comprising a polypeptide having protease activity fused, e.g., directly or through a linking moiety comprising one or more amino acid residues, to a variant Fc polypeptide. In some embodiments, a therapeutic compound or compound comprises a polypeptide comprising a polypeptide having protease activity linked by a non-covalent bond or a covalent bond, e.g., a covalent bond other than a peptide bond, e.g., a sulfhydryl bond, to a variant Fc polypeptide.

In some embodiments, the protease is an IgG cleaving protease. In some embodiments, the IgG cleaving protease is selected from IdeS, IdeSsuis, IdeE, IdeZ, IdeE2, IdeZ2, and IdeC. In some embodiments, the IgG cleaving protease is IdeS. In some embodiments, the IgG cleaving protease is IdeSsuis. In some embodiments, the IgG cleaving protease is IdeE. In some embodiments, the IgG cleaving protease is IdeZ. In some embodiments, the IgG cleaving protease is IdeE2. In some embodiments, the IgG cleaving protease is IdeZ2. In some embodiments, the IgG cleaving protease is IdeC. The IgG protease can be a variant protease of any of the foregoing. Examples of IgG proteases and variant proteases include, but are not limited to, those that are described in WO2003051914, WO2006131347, WO2016128558, WO2016128559, WO2016012285, WO2008071418, WO2012119983, WO2010057626, WO2015184325, WO2021026264, WO2021021989, WO2018034346, WO2010089126, WO200908027, WO2008136735, WO2015181356, WO2018093868, WO2013037824, WO2017134274, WO2016046220, WO2015040125, WO2009033670, WO2004096157, WO2010123885, WO2010118337, WO2019075360, WO2007019376, and U.S. Pat. No. 10,836,815, each of which are hereby incorporated by reference in their entirety. Non-limiting examples of proteases include, but are not limited to proteases comprise an amino acid sequence having at least 50%, 60%, 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to, or is identical to, a sequence provided in Table 4.

In some embodiments, a polypeptide comprises a polypeptide having protease activity covalently or non-covalently conjugated to the N-terminus of a variant Fc polypeptide. In some embodiments, a polypeptide comprises a polypeptide having protease activity covalently or non-covalently conjugated to the C-terminus of a variant Fc polypeptide. In some embodiments, there can be a linker moiety, such as a peptide moiety or a non-peptide linkage, between the polypeptide having protease activity and the N-terminus or the C-terminus of the Fc polypeptide.

In some embodiments, a polypeptide comprises a polypeptide having protease activity covalently or non-covalently conjugated to a nanobody and a variant Fc polypeptide, wherein the C-terminus of the polypeptide having protease activity is covalently or non-covalently conjugated to the N-terminus of a nanobody, and the N-terminus of the polypeptide having protease activity is covalently or non-covalently conjugated to the C-terminus of a variant Fc polypeptide. In some embodiments, a polypeptide comprises a polypeptide having protease activity covalently or non-covalently conjugated to a nanobody and a variant Fc polypeptide, wherein the N-terminus of a polypeptide having protease activity is covalently or non-covalently conjugated to the C-terminus of a nanobody, and the C-terminus of the polypeptide having protease activity is covalently or non-covalently conjugated to the N-terminus of a variant Fc polypeptide. In some embodiments, the polypeptide having protease activity is as provided herein. In some embodiments, the variant IgG Fc is as provided herein. In some embodiments, the nanobody is as provided herein.

In some embodiments, a polypeptide comprising a polypeptide having protease activity covalently or non-covalently conjugated to a variant Fc polypeptide further comprises a tag, such as a purification tag or detection tag. The tag can be used to facilitate the purification, isolation, or detection of the polypeptide. A non-limiting example of such a tag is a histidine tag, which is a plurality of hisitidines (e.g., 6 or more histidines). In some embodiments, a polypeptide comprising a polypeptide having protease activity covalently or non-covalently conjugated to a variant Fc polypeptide further comprises a histidine tag, wherein the C-terminus of the polypeptide having protease activity is covalently or non-covalently conjugated to the N-terminus of a variant Fc polypeptide, and wherein the C-terminus of the variant Fc polypeptide is covalently or non-covalently conjugated to the N-terminus of the tag. In some embodiments, a polypeptide comprising a polypeptide having protease activity covalently or non-covalently conjugated to a nanobody and a variant Fc polypeptide further comprises a tag. In some embodiments, a polypeptide comprising a polypeptide having protease activity covalently or non-covalently conjugated to a nanobody and a variant Fc polypeptide further comprises a tag, wherein the N-terminus of the polypeptide having protease activity is covalently or non-covalently conjugated to the C-terminus of the nanobody, wherein the C-terminus of the polypeptide having protease activity is covalently or non-covalently conjugated to the N-terminus of a variant Fc polypeptide, and wherein the C-terminus of the variant Fc polypeptide is covalently or non-covalently conjugated to the N-terminus of the tag. In some embodiments, a polypeptide comprising a polypeptide having protease activity covalently or non-covalently conjugated to a nanobody and a variant Fc polypeptide further comprises a histidine tag, wherein the N-terminus of the polypeptide having protease activity is covalently or non-covalently conjugated to the C-terminus of a variant Fc polypeptide, wherein the C-terminus of the polypeptide having protease activity is covalently or non-covalently conjugated to the N-terminus of the nanobody, and wherein the C-terminus of the nanobody is covalently or non-covalently conjugated to the N-terminus of the tag.

In some embodiments, the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity, or is identical, to a sequence provided in Table 3. In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity, or is identical to SEQ ID NO: 19, 20, 21, 22, 23, 24, 25, 42, 43, 44, 45, 46, 47, 48, or 49. In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity, or is identical, to to SEQ ID NO: 19. In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity, or is identical, to to SEQ ID NO: 20. In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to, or is identical to, SEQ ID NO: 21. In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to, or is identical to, SEQ ID NO: 22. In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to, or is identical to, SEQ ID NO: 23. In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to, or is identical to, SEQ ID NO: 24. In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to, or is identical to, SEQ ID NO: 25. In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to, or is identical to, SEQ ID NO:

42. In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to, or is identical to, SEQ ID NO: 43. In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to, or is identical to, SEQ ID NO: 44. In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to, or is identical to, SEQ ID NO: 45. In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to, or is identical to, SEQ ID NO: 46. In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to, or is identical to, SEQ ID NO: 47. In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to, or is identical to, SEQ ID NO: 48. In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to, or is identical to, SEQ ID NO: 49.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to a sequence provided in Table 3, and further comprises one or more mutations at position 234, 235, 237, 296, 329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to a sequence provided in Table 3, and further comprises one or more mutations at position L234, L235, G237, Y296, P329, or any combination thereof.

As used herein, the positions referenced in the Fc polypeptides as positions for a mutation refer to EU numbering system. The Fc polypeptides can aligned with a wild-type sequence to determine the positions that are mutated according to the numbering system.

As used herein in reference to a polypeptide that has a % identity to a reference sequence and further comprises a mutation at one or more positions, means a polypeptide that has the recited % identity to the reference sequence and also has one or more of the mutations at the recited positions.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, 20, 21, 22, 23, 24, or 25, and further comprises one or more mutations at position 234, 235, 237, 296, 329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position 234, 235, 237, 296, 329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position 234, 235, 237, 296, 329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position 234, 235, 237, 296, 329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position 234, 235, 237, 296, 329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position 234, 235, 237, 296, 329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position 234, 235, 237, 296, 329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position 234, 235, 237, 296, 329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, 20, 21, 22, 23, 24, or 25, and further comprises one or more mutations at position L234, L235, G237, Y296, P329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position L234, L235, G237, Y296, P329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position L234, L235, G237, Y296, P329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position L234, L235, G237, Y296, P329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position L234, L235, G237, Y296, P329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position L234, L235, G237, Y296, P329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position L234, L235, G237, Y296, P329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position L234, L235, G237, Y296, P329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any sequence provided in Table 3, and further comprises one or more mutations of L234A, L235A, G237A, Y296Q, P329K, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, 20, 21, 22, 23, 24, or 25, and further comprises one or more mutations of L234A, L235A, G237A, Y296Q, P329K, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations of L234A, L235A, G237A, Y296Q, P329K, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations of L234A, L235A, G237A, Y296Q, P329K, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations of L234A, L235A, G237A, Y296Q, P329K, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations of L234A, L235A, G237A, Y296Q, P329K, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations of L234A, L235A, G237A, Y296Q, P329K, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations of L234A, L235A, G237A, Y296Q, P329K, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations of L234A, L235A, G237A, Y296Q, P329K, or any combination thereof.

In some embodiments, a polypeptide comprises a polypeptide having protease activity covalently or non-covalently conjugated to a variant Fc polypeptide, wherein the variant Fc polypeptide comprises an amino acid sequence as provided in Table 3.

In some embodiments, a polypeptide comprises a polypeptide having protease activity covalently or non-covalently conjugated to a variant Fc polypeptide, wherein the variant Fc polypeptide comprises an amino acid sequence of SEQ ID NO: 19, 20, 21, 22, 23, 24, 25, 42, 43, 44, 45, 47, 48, or 49. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 19. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 20. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 21. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 22. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 23. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 24. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 25. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 42. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 43. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 44. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 45. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 46. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 47. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 48. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 49.

In some embodiments, a polypeptide comprises a polypeptide having protease activity covalently or non-covalently conjugated to a variant Fc polypeptide, wherein the variant Fc polypeptide comprises an amino acid sequence having a C-terminal lysine (K). In some embodiments, a polypeptide comprises a polypeptide having protease activity covalently or non-covalently conjugated to a variant Fc polypeptide, wherein the variant Fc polypeptide comprises an amino acid sequence that does not have (comprise) a C-terminal lysine (K).

In some embodiments, the protease present in the polypeptides provided for herein comprise an amino acid sequence having at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to, or is identical to, a sequence provided in Table 4, wherein the protease is covalently or non-covalently conjugated to a variant Fc polypeptide, and wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any sequence provided in Table 3.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, 28, 29, 31, 36, 37, 38, 39, 40, 41, 50, 51, 52, or 55, wherein the polypeptide having protease activity is covalently or non-covalently conjugated to a variant Fc polypeptide, and wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, 20, 21, 22, 23, 24, 25, 42, 43, 44, 45, 47, 48, or 49.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, and wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20. In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 25.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 42.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 43.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 44.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 45.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 46.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 47.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 48.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 49.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, and wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 25.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 42.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 43.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 44.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 45.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 46.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 47.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 48.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 49.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, and wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 25.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 42.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 43.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 44.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 45.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 46.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 47.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 48.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 49.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, and wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 25.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 42.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 43.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 44.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 45.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 46.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 47.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 48.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 49.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, and wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 25.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 42.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 43.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 44.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 45.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 46.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 47.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 48.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 49.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, and wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 25.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 42.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 43.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 44.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 45.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 46.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 47.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 48.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 49.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, and wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 25.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 42.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 43.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 44.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 45.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 46.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 47.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 48.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 49.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, and wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 25.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 42.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 43.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 44.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 45.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 46.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 47.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 48.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 49.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, and wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 25.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 42.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 43.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 44.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 45.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 46.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 47.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 48.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 49.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, and wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 25.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 42.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 43.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 44.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 45.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 46.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 47.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 48.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 49.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, and wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 25.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 42.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 43.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 44.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 45.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 46.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 47.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 48.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 49.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, and wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 25.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 42.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 43.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 44.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 45.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 46.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 47.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 48.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 49.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, and wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 25.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 42.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 43.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 44.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 45.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 46.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 47.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 48.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 49.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, and wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 25.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 42.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 43.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 44.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 45.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 46.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 47.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 48.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, and the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, or at least 98%, at least 99%, or 100% sequence identity to SEQ ID NO: 49.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any sequence provided in Table 3, and further comprises one or more mutations at position 234, 235, 237, 296, 329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, 20, 21, 22, 23, 24, or 25, and further comprises one or more mutations at position 234, 235, 237, 296, 329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position 234, 235, 237, 296, 329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position 234, 235, 237, 296, 329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position 234, 235, 237, 296, 329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position 234, 235, 237, 296, 329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position 234, 235, 237, 296, 329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position 234, 235, 237, 296, 329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position 234, 235, 237, 296, 329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any sequence provided in Table 3, and further comprises one or more mutations at position L234, L235, G237, Y296, P329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, 20, 21, 22, 23, 24, or 25, and further comprises one or more mutations at position L234, L235, G237, Y296, P329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position L234, L235, G237, Y296, P329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position L234, L235, G237, Y296, P329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position L234, L235, G237. Y296, P329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position L234, L235, G237, Y296, P329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position L234, L235, G237, Y296, P329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position L234, L235, G237, Y296, P329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any sequence provided in Table 4, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any sequence provided in Table 3, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, 28, 29, 31, 36, 37, 38, 39, 40, 41, 50, 51, 52, or 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, 20, 21, 22, 23, 24, or 25, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO:

21, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO:

25, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO:

22, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position 234, 235, 237, 296, 329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any sequence provided in Table 4, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any sequence provided in Table 3, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, 28, 29, 31, 36, 37, 38, 39, 40, 41, 50, 51, or 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, 20, 21, 22, 23, 24, or 25, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position L234, L235, G237. Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position L234, L235, G237. Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position L234, L235, G237. Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position L234, L235, G237. Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations at position L234, L235, G237, Y296, P329, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations at position L234, L235, G237, Y296, P329, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any sequence provided in Table 3, and further comprises one or more mutations of L234A, L235A, G237A, Y296Q, P329K, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, 20, 21, 22, 23, 24, or 25, and further comprises one or more mutations of L234A, L235A, G237A, Y296Q, P329K, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations of L234A, L235A, G237A, Y296Q, P329K, or any combination thereof.

In some embodiments, a variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations of L234A, L235A, G237A, Y296Q, P329K, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations of L234A, L235A, G237A, Y296Q, P329K, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations of L234A, L235A, G237A, Y296Q, P329K, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations of L234A, L235A, G237A, Y296Q, P329K, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations of L234A, L235A, G237A, Y296Q, P329K, or any combination thereof.

In some embodiments, a polypeptide comprises a polypeptide having protease activity covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any sequence provided in Table 4, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any sequence provided in Table 3, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, 28, 29, 31, 36, 37, 38, 39, 40, 41, 50, 51, 52, or 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, 20, 21, 22, 23, 24, or 25, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations of L234A, L235A, G237A, Y296Q, P329K, or any combination thereof. In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO:

19, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO:

25, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24, and further comprises one or more mutations of L234A, L235A, G237A, Y296Q, P329K, or any combination thereof.

In some embodiments, a polypeptide comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55, wherein the polypeptide having protease activity is covalently or non-covalently conjugated to a variant Fc polypeptide, wherein the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25, and further comprises one or more mutations of L234A, L235A, G237A, Y296Q, P329K, or any combination thereof.

In some embodiments, a polypeptide comprises a polypeptide having protease activity covalently or non-covalently conjugated to a variant Fc polypeptide, wherein the variant Fc polypeptide comprises an amino acid sequence as provided in Table 3. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 19, 20, 21, 22, 23, 24, 25, 42, 43, 44, 45, 46, 47, 48, or 49. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 19. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 20. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 21. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 22. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 23. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 24. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 25. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 42. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 43. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 44. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 45. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 46. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 47. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 48. In some embodiments, a polypeptide comprises a polypeptide having protease activity covalently or non-covalently conjugated to a variant Fc polypeptide, wherein the variant Fc polypeptide comprises an amino acid sequence of SEQ ID NO: 49.

In some embodiments, a polypeptide comprises a polypeptide having protease activity comprising any sequence provided in Table 4, wherein the polypeptide having protease activity is covalently or non-covalently conjugated to a variant Fc polypeptide, wherein the variant Fc polypeptide comprises an amino acid sequence as provided in Table 3. In some embodiments, a polypeptide comprises a polypeptide having protease activity comprising an amino acid sequence of SEQ ID NO: 26, 28, 29, 31, 36, 37, 38, 39, 40, 41, 50, 51, 52, or 55, wherein the polypeptide having protease activity is covalently or non-covalently conjugated to a variant Fc polypeptide, wherein the variant Fc polypeptide comprises an amino acid sequence of SEQ ID NO: 19, 20, 21, 22, 23, 24, 25, 42, 43, 44, 45, 46, 47, 48, or 49.

In some embodiments, a polypeptide comprises a polypeptide having protease activity comprising an amino acid sequence of SEQ ID NO: 26, wherein the polypeptide having protease activity is covalently or non-covalently conjugated to a variant Fc polypeptide, wherein the variant Fc polypeptide comprises an amino acid sequence of SEQ ID NO: 19.

In some embodiments, a polypeptide comprises a polypeptide having protease activity comprising an amino acid sequence of SEQ ID NO: 26, wherein the polypeptide having protease variant Fc polypeptide comprises an amino acid sequence of SEQ ID NO: 20.

In some embodiments, a polypeptide comprises a polypeptide having protease activity comprising an amino acid sequence of SEQ ID NO: 26, wherein the polypeptide having protease activity is covalently or non-covalently conjugated to a variant Fc polypeptide, wherein the variant Fc polypeptide comprises an amino acid sequence of SEQ ID NO: 21.

In some embodiments, a polypeptide comprises a polypeptide having protease activity comprising an amino acid sequence of SEQ ID NO: 26, wherein the polypeptide having protease activity is covalently or non-covalently conjugated to a variant Fc polypeptide, wherein the variant Fc polypeptide comprises an amino acid sequence of SEQ ID NO: 22.

In some embodiments, a polypeptide comprises a polypeptide having protease activity comprising an amino acid sequence of SEQ ID NO: 26, wherein the polypeptide having protease activity is covalently or non-covalently conjugated to a variant Fc polypeptide, wherein the variant Fc polypeptide comprises an amino acid sequence of SEQ ID NO: 23.

In some embodiments, a polypeptide comprises a polypeptide having protease activity comprising an amino acid sequence of SEQ ID NO: 26, wherein the polypeptide having protease activity is covalently or non-covalently conjugated to a variant Fc polypeptide, wherein the variant Fc polypeptide comprises an amino acid sequence of SEQ ID NO: 24.

In some embodiments, a polypeptide comprises a polypeptide having protease activity comprising an amino acid sequence of SEQ ID NO: 26, wherein the polypeptide having protease activity is covalently or non-covalently conjugated to a variant Fc polypeptide, wherein the variant Fc polypeptide comprises an amino acid sequence of SEQ ID NO: 25.

In some embodiments, a polypeptide comprises a polypeptide having protease activity comprising an amino acid sequence of SEQ ID NO: 26, wherein the polypeptide having protease activity is covalently or non-covalently conjugated to a variant Fc polypeptide, wherein the variant Fc polypeptide comprises an amino acid sequence of SEQ ID NO: 42.

In some embodiments, a polypeptide comprises a polypeptide having protease activity comprising an amino acid sequence of SEQ ID NO: 26, wherein the polypeptide having protease activity is covalently or non-covalently conjugated to a variant Fc polypeptide, wherein the variant Fc polypeptide comprises an amino acid sequence of SEQ ID NO: 43.

In some embodiments, a polypeptide comprises a polypeptide having protease activity comprising an amino acid sequence of SEQ ID NO: 26, wherein the polypeptide having protease activity is covalently or non-covalently conjugated to a variant Fc polypeptide, wherein the variant Fc polypeptide comprises an amino acid sequence of SEQ ID NO: 44.

In some embodiments, a polypeptide comprises a polypeptide having protease activity comprising an amino acid sequence of SEQ ID NO: 26, wherein the polypeptide having protease activity is covalently or non-covalently conjugated to a variant Fc polypeptide, wherein the variant Fc polypeptide comprises an amino acid sequence of SEQ ID NO: 45.

In some embodiments, a polypeptide comprises a polypeptide having protease activity comprising an amino acid sequence of SEQ ID NO: 26, wherein the polypeptide having protease activity is covalently or non-covalently conjugated to a variant Fc polypeptide, wherein the variant Fc polypeptide comprises an amino acid sequence of SEQ ID NO: 46.

In some embodiments, a polypeptide comprises a polypeptide having protease activity comprising an amino acid sequence of SEQ ID NO: 26, wherein the polypeptide having protease activity is covalently or non-covalently conjugated to a variant Fc polypeptide, wherein the variant Fc polypeptide comprises an amino acid sequence of SEQ ID NO: 47.

In some embodiments, a polypeptide comprises a polypeptide having protease activity comprising an amino acid sequence of SEQ ID NO: 26, wherein the polypeptide having protease activity is covalently or non-covalently conjugated to a variant Fc polypeptide, wherein the variant Fc polypeptide comprises an amino acid sequence of SEQ ID NO: 48.

In some embodiments, a polypeptide comprises a polypeptide having protease activity comprising an amino acid sequence of SEQ ID NO: 26, wherein the polypeptide having protease activity is covalently or non-covalently conjugated to a variant Fc polypeptide, wherein the variant Fc polypeptide comprises an amino acid sequence of SEQ ID NO: 49.

In some embodiments, a polypeptide comprises a polypeptide having protease activity comprising an amino acid sequence of SEQ ID NO: 28, wherein the polypeptide having protease activity is covalently or non-covalently conjugated to a variant Fc polypeptide, wherein the variant Fc polypeptide comprises an amino acid sequence of SEQ ID NO: 19.

In some embodiments, a polypeptide comprises a polypeptide having protease activity comprising an amino acid sequence of SEQ ID NO: 28, wherein the polypeptide having protease variant Fc polypeptide comprises an amino acid sequence of SEQ ID NO: 20.

In some embodiments, a polypeptide comprises a polypeptide having protease activity comprising an amino acid sequence of SEQ ID NO: 28, wherein the polypeptide having protease activity is covalently or non-covalently conjugated to a variant Fc polypeptide, wherein the variant Fc polypeptide comprises an amino acid sequence of SEQ ID NO: 21.

In some embodiments, a polypeptide comprises a polypeptide having protease activity comprising an amino acid sequence of SEQ ID NO: 28, wherein the polypeptide having protease activity is covalently or non-covalently conjugated to a variant Fc polypeptide, wherein the variant Fc polypeptide comprises an amino acid sequence of SEQ ID NO: 22.

In some embodiments, a polypeptide comprises a polypeptide having protease activity comprising an amino acid sequence of SEQ ID NO: 28, wherein the polypeptide having protease activity is covalently or non-covalently conjugated to a variant Fc polypeptide, wherein the variant Fc polypeptide comprises an amino acid sequence of SEQ ID NO: 23.

In some embodiments, a polypeptide comprises a polypeptide having protease activity comprising an amino acid sequence of SEQ ID NO: 28, wherein the polypeptide having protease activity is covalently or non-covalently conjugated to a variant Fc polypeptide, wherein the variant Fc polypeptide comprises an amino acid sequence of SEQ ID NO: 24.

In some embodiments, a polypeptide comprises a polypeptide having protease activity comprising an amino acid sequence of SEQ ID NO: 28, wherein the polypeptide having protease activity is covalently or non-covalently conjugated to a variant Fc polypeptide, wherein the variant Fc polypeptide comprises an amino acid sequence of SEQ ID NO: 25.

In some embodiments, a polypeptide comprises a polypeptide having protease activity comprising an amino acid sequence of SEQ ID NO: 28, wherein the polypeptide having protease activity is covalently or non-covalently conjugated to a variant Fc polypeptide, wherein the variant Fc polypeptide comprises an amino acid sequence of SEQ ID NO: 42.

In some embodiments, a polypeptide comprises a polypeptide having protease activity comprising an amino acid sequence of SEQ ID NO: 28, wherein the polypeptide having protease activity is covalently or non-covalently conjugated to a variant Fc polypeptide, wherein the variant Fc polypeptide comprises an amino acid sequence of SEQ ID NO: 43.

In some embodiments, a polypeptide comprises a polypeptide having protease activity comprising an amino acid sequence of SEQ ID NO: 28, wherein the polypeptide having protease activity is covalently or non-covalently conjugated to a variant Fc polypeptide, wherein the variant Fc polypeptide comprises an amino acid sequence of SEQ ID NO: 44.

In some embodiments, a polypeptide comprises a polypeptide having protease activity comprising an amino acid sequence of SEQ ID NO: 28, wherein the polypeptide having protease activity is covalently or non-covalently conjugated to a variant Fc polypeptide, wherein the variant Fc polypeptide comprises an amino acid sequence of SEQ ID NO: 45.

In some embodiments, a polypeptide comprises a polypeptide having protease activity comprising an amino acid sequence of SEQ ID NO: 28, wherein the polypeptide having protease activity is covalently or non-covalently conjugated to a variant Fc polypeptide, wherein the variant Fc polypeptide comprises an amino acid sequence of SEQ ID NO: 46.

In some embodiments, a polypeptide comprises a polypeptide having protease activity comprising an amino acid sequence of SEQ ID NO: 28, wherein the polypeptide having protease activity is covalently or non-covalently conjugated to a variant Fc polypeptide, wherein the variant Fc polypeptide comprises an amino acid sequence of SEQ ID NO: 47.

In some embodiments, a polypeptide comprises a polypeptide having protease activity comprising an amino acid sequence of SEQ ID NO: 28, wherein the polypeptide having protease activity is covalently or non-covalently conjugated to a variant Fc polypeptide, wherein the variant Fc polypeptide comprises an amino acid sequence of SEQ ID NO: 48.

In some embodiments, a polypeptide comprises a polypeptide having protease activity comprising an amino acid sequence of SEQ ID NO: 28, wherein the polypeptide having protease activity is covalently or non-covalently conjugated to a variant Fc polypeptide, wherein the variant Fc polypeptide comprises an amino acid sequence of SEQ ID NO: 49. In some embodiments, a polypeptide comprises a polypeptide having protease activity comprising an amino acid sequence of SEQ ID NO: 29, wherein the polypeptide having protease activity is covalently or non-covalently conjugated to a variant Fc polypeptide, wherein the variant Fc polypeptide comprises an amino acid sequence of SEQ ID NO: 19.

In some embodiments, a polypeptide comprises a polypeptide having protease activity comprising an amino acid sequence of SEQ ID NO: 29, wherein the polypeptide having protease variant Fc polypeptide comprises an amino acid sequence of SEQ ID NO: 20.

In some embodiments, a polypeptide comprises a polypeptide having protease activity comprising an amino acid sequence of SEQ ID NO: 29, wherein the polypeptide having protease activity is covalently or non-covalently conjugated to a variant Fc polypeptide, wherein the variant Fc polypeptide comprises an amino acid sequence of SEQ ID NO: 21.

In some embodiments, a polypeptide comprises a polypeptide having protease activity comprising an amino acid sequence of SEQ ID NO: 29, wherein the polypeptide having protease activity is covalently or non-covalently conjugated to a variant Fc polypeptide, wherein the variant Fc polypeptide comprises an amino acid sequence of SEQ ID NO: 22.

In some embodiments, a polypeptide comprises a polypeptide having protease activity comprising an amino acid sequence of SEQ ID NO: 29, wherein the polypeptide having protease activity is covalently or non-covalently conjugated to a variant Fc polypeptide, wherein the variant Fc polypeptide comprises an amino acid sequence of SEQ ID NO: 23.

In some embodiments, a polypeptide comprises a polypeptide having protease activity comprising an amino acid sequence of SEQ ID NO: 29, wherein the polypeptide having protease activity is covalently or non-covalently conjugated to a variant Fc polypeptide, wherein the variant Fc polypeptide comprises an amino acid sequence of SEQ ID NO: 24.

In some embodiments, a polypeptide comprises a polypeptide having protease activity comprising an amino acid sequence of SEQ ID NO: 29, wherein the polypeptide having protease activity is covalently or non-covalently conjugated to a variant Fc polypeptide, wherein the variant Fc polypeptide comprises an amino acid sequence of SEQ ID NO: 25.

In some embodiments, a polypeptide comprises a polypeptide having protease activity comprising an amino acid sequence of SEQ ID NO: 29, wherein the polypeptide having protease activity is covalently or non-covalently conjugated to a variant Fc polypeptide, wherein the variant Fc polypeptide comprises an amino acid sequence of SEQ ID NO: 42.

In some embodiments, a polypeptide comprises a polypeptide having protease activity comprising an amino acid sequence of SEQ ID NO: 29, wherein the polypeptide having protease activity is covalently or non-covalently conjugated to a variant Fc polypeptide, wherein the variant Fc polypeptide comprises an amino acid sequence of SEQ ID NO: 43.

In some embodiments, a polypeptide comprises a polypeptide having protease activity comprising an amino acid sequence of SEQ ID NO: 29, wherein the polypeptide having protease activity is covalently or non-covalently conjugated to a variant Fc polypeptide, wherein the variant Fc polypeptide comprises an amino acid sequence of SEQ ID NO: 44.

In some embodiments, a polypeptide comprises a polypeptide having protease activity comprising an amino acid sequence of SEQ ID NO: 29, wherein the polypeptide having protease activity is covalently or non-covalently conjugated to a variant Fc polypeptide, wherein the variant Fc polypeptide comprises an amino acid sequence of SEQ ID NO: 45.

In some embodiments, a polypeptide comprises a polypeptide having protease activity comprising an amino acid sequence of SEQ ID NO: 29, wherein the polypeptide having protease activity is covalently or non-covalently conjugated to a variant Fc polypeptide, wherein the variant Fc polypeptide comprises an amino acid sequence of SEQ ID NO: 46.

In some embodiments, a polypeptide comprises a polypeptide having protease activity comprising an amino acid sequence of SEQ ID NO: 29, wherein the polypeptide having protease activity is covalently or non-covalently conjugated to a variant Fc polypeptide, wherein the variant Fc polypeptide comprises an amino acid sequence of SEQ ID NO: 47.

In some embodiments, a polypeptide comprises a polypeptide having protease activity comprising an amino acid sequence of SEQ ID NO: 29, wherein the polypeptide having protease activity is covalently or non-covalently conjugated to a variant Fc polypeptide, wherein the variant Fc polypeptide comprises an amino acid sequence of SEQ ID NO: 48.

In some embodiments, a polypeptide comprises a polypeptide having protease activity comprising an amino acid sequence of SEQ ID NO: 29, wherein the polypeptide having protease activity is covalently or non-covalently conjugated to a variant Fc polypeptide, wherein the variant Fc polypeptide comprises an amino acid sequence of SEQ ID NO: 49.

In some embodiments, a polypeptide comprises a polypeptide having protease activity comprising an amino acid sequence of SEQ ID NO: 31, wherein the polypeptide having protease activity is covalently or non-covalently conjugated to a variant Fc polypeptide, wherein the variant Fc polypeptide comprises an amino acid sequence of SEQ ID NO: 19.

In some embodiments, a polypeptide comprises a polypeptide having protease activity comprising an amino acid sequence of SEQ ID NO: 31, wherein the polypeptide having protease variant Fc polypeptide comprises an amino acid sequence of SEQ ID NO: 20.

In some embodiments, a polypeptide comprises a polypeptide having protease activity comprising an amino acid sequence of SEQ ID NO: 31, wherein the polypeptide having protease activity is covalently or non-covalently conjugated to a variant Fc polypeptide, wherein the variant Fc polypeptide comprises an amino acid sequence of SEQ ID NO: 21.

In some embodiments, a polypeptide comprises a polypeptide having protease activity comprising an amino acid sequence of SEQ ID NO: 31, wherein the polypeptide having protease activity is covalently or non-covalently conjugated to a variant Fc polypeptide, wherein the variant Fc polypeptide comprises an amino acid sequence of SEQ ID NO: 22.

In some embodiments, a polypeptide comprises a polypeptide having protease activity comprising an amino acid sequence of SEQ ID NO: 31, wherein the polypeptide having protease activity is covalently or non-covalently conjugated to a variant Fc polypeptide, wherein the variant Fc polypeptide comprises an amino acid sequence of SEQ ID NO: 23.

In some embodiments, a polypeptide comprises a polypeptide having protease activity comprising an amino acid sequence of SEQ ID NO: 31, wherein the polypeptide having protease activity is covalently or non-covalently conjugated to a variant Fc polypeptide, wherein the variant Fc polypeptide comprises an amino acid sequence of SEQ ID NO: 24.

In some embodiments, a polypeptide comprises a polypeptide having protease activity comprising an amino acid sequence of SEQ ID NO: 31, wherein the polypeptide having protease activity is covalently or non-covalently conjugated to a variant Fc polypeptide, wherein the variant Fc polypeptide comprises an amino acid sequence of SEQ ID NO: 25.

In some embodiments, a polypeptide comprises a polypeptide having protease activity comprising an amino acid sequence of SEQ ID NO: 31, wherein the polypeptide having protease activity is covalently or non-covalently conjugated to a variant Fc polypeptide, wherein the variant Fc polypeptide comprises an amino acid sequence of SEQ ID NO: 42.

In some embodiments, a polypeptide comprises a polypeptide having protease activity comprising an amino acid sequence of SEQ ID NO: 31, wherein the polypeptide having protease activity is covalently or non-covalently conjugated to a variant Fc polypeptide, wherein the variant Fc polypeptide comprises an amino acid sequence of SEQ ID NO: 43.

In some embodiments, a polypeptide comprises a polypeptide having protease activity comprising an amino acid sequence of SEQ ID NO: 31, wherein the polypeptide having protease activity is covalently or non-covalently conjugated to a variant Fc polypeptide, wherein the variant Fc polypeptide comprises an amino acid sequence of SEQ ID NO: 44.

In some embodiments, a polypeptide comprises a polypeptide having protease activity comprising an amino acid sequence of SEQ ID NO: 31, wherein the polypeptide having protease activity is covalently or non-covalently conjugated to a variant Fc polypeptide, wherein the variant Fc polypeptide comprises an amino acid sequence of SEQ ID NO: 45.

In some embodiments, a polypeptide comprises a polypeptide having protease activity comprising an amino acid sequence of SEQ ID NO: 31, wherein the polypeptide having protease activity is covalently or non-covalently conjugated to a variant Fc polypeptide, wherein the variant Fc polypeptide comprises an amino acid sequence of SEQ ID NO: 46.

In some embodiments, a polypeptide comprises a polypeptide having protease activity comprising an amino acid sequence of SEQ ID NO: 31, wherein the polypeptide having protease activity is covalently or non-covalently conjugated to a variant Fc polypeptide, wherein the variant Fc polypeptide comprises an amino acid sequence of SEQ ID NO: 47.

In some embodiments, a polypeptide comprises a polypeptide having protease activity comprising an amino acid sequence of SEQ ID NO: 31, wherein the polypeptide having protease activity is covalently or non-covalently conjugated to a variant Fc polypeptide, wherein the variant Fc polypeptide comprises an amino acid sequence of SEQ ID NO: 48.

In some embodiments, a polypeptide comprises a polypeptide having protease activity comprising an amino acid sequence of SEQ ID NO: 31, wherein the polypeptide having protease activity is covalently or non-covalently conjugated to a variant Fc polypeptide, wherein the variant Fc polypeptide comprises an amino acid sequence of SEQ ID NO: 49. In some embodiments, a polypeptide comprises a polypeptide having protease activity comprising an amino acid sequence of SEQ ID NO: 36, wherein the polypeptide having protease activity is covalently or non-covalently conjugated to a variant Fc polypeptide, wherein the variant Fc polypeptide comprises an amino acid sequence of SEQ ID NO: 19.

In some embodiments, a polypeptide comprises a polypeptide having protease activity comprising an amino acid sequence of SEQ ID NO: 36, wherein the polypeptide having protease variant Fc polypeptide comprises an amino acid sequence of SEQ ID NO: 20.

In some embodiments, a polypeptide comprises a polypeptide having protease activity comprising an amino acid sequence of SEQ ID NO: 36, wherein the polypeptide having protease activity is covalently or non-covalently conjugated to a variant Fc polypeptide, wherein the variant Fc polypeptide comprises an amino acid sequence of SEQ ID NO: 21.

In some embodiments, a polypeptide comprises a polypeptide having protease activity comprising an amino acid sequence of SEQ ID NO: 36, wherein the polypeptide having protease activity is covalently or non-covalently conjugated to a variant Fc polypeptide, wherein the variant Fc polypeptide comprises an amino acid sequence of SEQ ID NO: 22.

In some embodiments, a polypeptide comprises a polypeptide having protease activity comprising an amino acid sequence of SEQ ID NO: 36, wherein the polypeptide having protease activity is covalently or non-covalently conjugated to a variant Fc polypeptide, wherein the variant Fc polypeptide comprises an amino acid sequence of SEQ ID NO: 23.

In some embodiments, a polypeptide comprises a polypeptide having protease activity comprising an amino acid sequence of SEQ ID NO: 36, wherein the polypeptide having protease activity is covalently or non-covalently conjugated to a variant Fc polypeptide, wherein the variant Fc polypeptide comprises an amino acid sequence of SEQ ID NO: 24.

In some embodiments, a polypeptide comprises a polypeptide having protease activity comprising an amino acid sequence of SEQ ID NO: 36, wherein the polypeptide having protease activity is covalently or non-covalently conjugated to a variant Fc polypeptide, wherein the variant Fc polypeptide comprises an amino acid sequence of SEQ ID NO: 25.

In some embodiments, a polypeptide comprises a polypeptide having protease activity comprising an amino acid sequence of SEQ ID NO: 36, wherein the polypeptide having protease activity is covalently or non-covalently conjugated to a variant Fc polypeptide, wherein the variant Fc polypeptide comprises an amino acid sequence of SEQ ID NO: 42.

In some embodiments, a polypeptide comprises a polypeptide having protease activity comprising an amino acid sequence of SEQ ID NO: 36, wherein the polypeptide having protease activity is covalently or non-covalently conjugated to a variant Fc polypeptide, wherein the variant Fc polypeptide comprises an amino acid sequence of SEQ ID NO: 43.

In some embodiments, a polypeptide comprises a polypeptide having protease activity comprising an amino acid sequence of SEQ ID NO: 36, wherein the polypeptide having protease activity is covalently or non-covalently conjugated to a variant Fc polypeptide, wherein the variant Fc polypeptide comprises an amino acid sequence of SEQ ID NO: 44.

In some embodiments, a polypeptide comprises a polypeptide having protease activity comprising an amino acid sequence of SEQ ID NO: 36, wherein the polypeptide having protease activity is covalently or non-covalently conjugated to a variant Fc polypeptide, wherein the variant Fc polypeptide comprises an amino acid sequence of SEQ ID NO: 45.

In some embodiments, a polypeptide comprises a polypeptide having protease activity comprising an amino acid sequence of SEQ ID NO: 36, wherein the polypeptide having protease activity is covalently or non-covalently conjugated to a variant Fc polypeptide, wherein the variant Fc polypeptide comprises an amino acid sequence of SEQ ID NO: 46.

In some embodiments, a polypeptide comprises a polypeptide having protease activity comprising an amino acid sequence of SEQ ID NO: 36, wherein the polypeptide having protease activity is covalently or non-covalently conjugated to a variant Fc polypeptide, wherein the variant Fc polypeptide comprises an amino acid sequence of SEQ ID NO: 47.

In some embodiments, a polypeptide comprises a polypeptide having protease activity comprising an amino acid sequence of SEQ ID NO: 36, wherein the polypeptide having protease activity is covalently or non-covalently conjugated to a variant Fc polypeptide, wherein the variant Fc polypeptide comprises an amino acid sequence of SEQ ID NO: 48.

In some embodiments, a polypeptide comprises a polypeptide having protease activity comprising an amino acid sequence of SEQ ID NO: 36, wherein the polypeptide having protease activity is covalently or non-covalently conjugated to a variant Fc polypeptide, wherein the variant Fc polypeptide comprises an amino acid sequence of SEQ ID NO: 49.

In some embodiments, a polypeptide comprises a polypeptide having protease activity comprising an amino acid sequence of SEQ ID NO: 37, wherein the polypeptide having protease activity is covalently or non-covalently conjugated to a variant Fc polypeptide, wherein the variant Fc polypeptide comprises an amino acid sequence of SEQ ID NO: 19.

In some embodiments, a polypeptide comprises a polypeptide having protease activity comprising an amino acid sequence of SEQ ID NO: 37, wherein the polypeptide having protease variant Fc polypeptide comprises an amino acid sequence of SEQ ID NO: 20.

In some embodiments, a polypeptide comprises a polypeptide having protease activity comprising an amino acid sequence of SEQ ID NO: 37, wherein the polypeptide having protease activity is covalently or non-covalently conjugated to a variant Fc polypeptide, wherein the variant Fc polypeptide comprises an amino acid sequence of SEQ ID NO: 21.

In some embodiments, a polypeptide comprises a polypeptide having protease activity comprising an amino acid sequence of SEQ ID NO: 37, wherein the polypeptide having protease activity is covalently or non-covalently conjugated to a variant Fc polypeptide, wherein the variant Fc polypeptide comprises an amino acid sequence of SEQ ID NO: 22.

In some embodiments, a polypeptide comprises a polypeptide having protease activity comprising an amino acid sequence of SEQ ID NO: 37, wherein the polypeptide having protease activity is covalently or non-covalently conjugated to a variant Fc polypeptide, wherein the variant Fc polypeptide comprises an amino acid sequence of SEQ ID NO: 23.

In some embodiments, a polypeptide comprises a polypeptide having protease activity comprising an amino acid sequence of SEQ ID NO: 37, wherein the polypeptide having protease activity is covalently or non-covalently conjugated to a variant Fc polypeptide, wherein the variant Fc polypeptide comprises an amino acid sequence of SEQ ID NO: 24.

In some embodiments, a polypeptide comprises a polypeptide having protease activity comprising an amino acid sequence of SEQ ID NO: 37, wherein the polypeptide having protease activity is covalently or non-covalently conjugated to a variant Fc polypeptide, wherein the variant Fc polypeptide comprises an amino acid sequence of SEQ ID NO: 25.

In some embodiments, a polypeptide comprises a polypeptide having protease activity comprising an amino acid sequence of SEQ ID NO: 37, wherein the polypeptide having protease activity is covalently or non-covalently conjugated to a variant Fc polypeptide, wherein the variant Fc polypeptide comprises an amino acid sequence of SEQ ID NO: 42.

In some embodiments, a polypeptide comprises a polypeptide having protease activity comprising an amino acid sequence of SEQ ID NO: 37, wherein the polypeptide having protease activity is covalently or non-covalently conjugated to a variant Fc polypeptide, wherein the variant Fc polypeptide comprises an amino acid sequence of SEQ ID NO: 43.

In some embodiments, a polypeptide comprises a polypeptide having protease activity comprising an amino acid sequence of SEQ ID NO: 37, wherein the polypeptide having protease activity is covalently or non-covalently conjugated to a variant Fc polypeptide, wherein the variant Fc polypeptide comprises an amino acid sequence of SEQ ID NO: 44.

In some embodiments, a polypeptide comprises a polypeptide having protease activity comprising an amino acid sequence of SEQ ID NO: 37, wherein the polypeptide having protease activity is covalently or non-covalently conjugated to a variant Fc polypeptide, wherein the variant Fc polypeptide comprises an amino acid sequence of SEQ ID NO: 45.

In some embodiments, a polypeptide comprises a polypeptide having protease activity comprising an amino acid sequence of SEQ ID NO: 37, wherein the polypeptide having protease activity is covalently or non-covalently conjugated to a variant Fc polypeptide, wherein the variant Fc polypeptide comprises an amino acid sequence of SEQ ID NO: 46.

In some embodiments, a polypeptide comprises a polypeptide having protease activity comprising an amino acid sequence of SEQ ID NO: 37, wherein the polypeptide having protease activity is covalently or non-covalently conjugated to a variant Fc polypeptide, wherein the variant Fc polypeptide comprises an amino acid sequence of SEQ ID NO: 47.

In some embodiments, a polypeptide comprises a polypeptide having protease activity comprising an amino acid sequence of SEQ ID NO: 37, wherein the polypeptide having protease activity is covalently or non-covalently conjugated to a variant Fc polypeptide, wherein the variant Fc polypeptide comprises an amino acid sequence of SEQ ID NO: 48.

In some embodiments, a polypeptide comprises a polypeptide having protease activity comprising an amino acid sequence of SEQ ID NO: 37, wherein the polypeptide having protease activity is covalently or non-covalently conjugated to a variant Fc polypeptide, wherein the variant Fc polypeptide comprises an amino acid sequence of SEQ ID NO: 49.

In some embodiments, a polypeptide comprises a polypeptide having protease activity comprising an amino acid sequence of SEQ ID NO: 38, wherein the polypeptide having protease activity is covalently or non-covalently conjugated to a variant Fc polypeptide, wherein the variant Fc polypeptide comprises an amino acid sequence of SEQ ID NO: 19.

In some embodiments, a polypeptide comprises a polypeptide having protease activity comprising an amino acid sequence of SEQ ID NO: 38, wherein the polypeptide having protease variant Fc polypeptide comprises an amino acid sequence of SEQ ID NO: 20.

In some embodiments, a polypeptide comprises a polypeptide having protease activity comprising an amino acid sequence of SEQ ID NO: 38, wherein the polypeptide having protease activity is covalently or non-covalently conjugated to a variant Fc polypeptide, wherein the variant Fc polypeptide comprises an amino acid sequence of SEQ ID NO: 21.

In some embodiments, a polypeptide comprises a polypeptide having protease activity comprising an amino acid sequence of SEQ ID NO: 38, wherein the polypeptide having protease activity is covalently or non-covalently conjugated to a variant Fc polypeptide, wherein the variant Fc polypeptide comprises an amino acid sequence of SEQ ID NO: 22.

In some embodiments, a polypeptide comprises a polypeptide having protease activity comprising an amino acid sequence of SEQ ID NO: 38, wherein the polypeptide having protease activity is covalently or non-covalently conjugated to a variant Fc polypeptide, wherein the variant Fc polypeptide comprises an amino acid sequence of SEQ ID NO: 23.

In some embodiments, a polypeptide comprises a polypeptide having protease activity comprising an amino acid sequence of SEQ ID NO: 38, wherein the polypeptide having protease activity is covalently or non-covalently conjugated to a variant Fc polypeptide, wherein the variant Fc polypeptide comprises an amino acid sequence of SEQ ID NO: 24.

In some embodiments, a polypeptide comprises a polypeptide having protease activity comprising an amino acid sequence of SEQ ID NO: 38, wherein the polypeptide having protease activity is covalently or non-covalently conjugated to a variant Fc polypeptide, wherein the variant Fc polypeptide comprises an amino acid sequence of SEQ ID NO: 25.

In some embodiments, a polypeptide comprises a polypeptide having protease activity comprising an amino acid sequence of SEQ ID NO: 38, wherein the polypeptide having protease activity is covalently or non-covalently conjugated to a variant Fc polypeptide, wherein the variant Fc polypeptide comprises an amino acid sequence of SEQ ID NO: 42.

In some embodiments, a polypeptide comprises a polypeptide having protease activity comprising an amino acid sequence of SEQ ID NO: 38, wherein the polypeptide having protease activity is covalently or non-covalently conjugated to a variant Fc polypeptide, wherein the variant Fc polypeptide comprises an amino acid sequence of SEQ ID NO: 43.

In some embodiments, a polypeptide comprises a polypeptide having protease activity comprising an amino acid sequence of SEQ ID NO: 38, wherein the polypeptide having protease activity is covalently or non-covalently conjugated to a variant Fc polypeptide, wherein the variant Fc polypeptide comprises an amino acid sequence of SEQ ID NO: 44.

In some embodiments, a polypeptide comprises a polypeptide having protease activity comprising an amino acid sequence of SEQ ID NO: 38, wherein the polypeptide having protease activity is covalently or non-covalently conjugated to a variant Fc polypeptide, wherein the variant Fc polypeptide comprises an amino acid sequence of SEQ ID NO: 45.

In some embodiments, a polypeptide comprises a polypeptide having protease activity comprising an amino acid sequence of SEQ ID NO: 38, wherein the polypeptide having protease activity is covalently or non-covalently conjugated to a variant Fc polypeptide, wherein the variant Fc polypeptide comprises an amino acid sequence of SEQ ID NO: 46.

In some embodiments, a polypeptide comprises a polypeptide having protease activity comprising an amino acid sequence of SEQ ID NO: 38, wherein the polypeptide having protease activity is covalently or non-covalently conjugated to a variant Fc polypeptide, wherein the variant Fc polypeptide comprises an amino acid sequence of SEQ ID NO: 47.

In some embodiments, a polypeptide comprises a polypeptide having protease activity comprising an amino acid sequence of SEQ ID NO: 38, wherein the polypeptide having protease activity is covalently or non-covalently conjugated to a variant Fc polypeptide, wherein the variant Fc polypeptide comprises an amino acid sequence of SEQ ID NO: 48.

In some embodiments, a polypeptide comprises a polypeptide having protease activity comprising an amino acid sequence of SEQ ID NO: 38, wherein the polypeptide having protease activity is covalently or non-covalently conjugated to a variant Fc polypeptide, wherein the variant Fc polypeptide comprises an amino acid sequence of SEQ ID NO: 49.

In some embodiments, a polypeptide comprises a polypeptide having protease activity comprising an amino acid sequence of SEQ ID NO: 39, wherein the polypeptide having protease activity is covalently or non-covalently conjugated to a variant Fc polypeptide, wherein the variant Fc polypeptide comprises an amino acid sequence of SEQ ID NO: 19.

In some embodiments, a polypeptide comprises a polypeptide having protease activity comprising an amino acid sequence of SEQ ID NO: 39, wherein the polypeptide having protease variant Fc polypeptide comprises an amino acid sequence of SEQ ID NO: 20.

In some embodiments, a polypeptide comprises a polypeptide having protease activity comprising an amino acid sequence of SEQ ID NO: 39, wherein the polypeptide having protease activity is covalently or non-covalently conjugated to a variant Fc polypeptide, wherein the variant Fc polypeptide comprises an amino acid sequence of SEQ ID NO: 21.

In some embodiments, a polypeptide comprises a polypeptide having protease activity comprising an amino acid sequence of SEQ ID NO: 39, wherein the polypeptide having protease activity is covalently or non-covalently conjugated to a variant Fc polypeptide, wherein the variant Fc polypeptide comprises an amino acid sequence of SEQ ID NO: 22.

In some embodiments, a polypeptide comprises a polypeptide having protease activity comprising an amino acid sequence of SEQ ID NO: 39, wherein the polypeptide having protease activity is covalently or non-covalently conjugated to a variant Fc polypeptide, wherein the variant Fc polypeptide comprises an amino acid sequence of SEQ ID NO: 23.

In some embodiments, a polypeptide comprises a polypeptide having protease activity comprising an amino acid sequence of SEQ ID NO: 39, wherein the polypeptide having protease activity is covalently or non-covalently conjugated to a variant Fc polypeptide, wherein the variant Fc polypeptide comprises an amino acid sequence of SEQ ID NO: 24.

In some embodiments, a polypeptide comprises a polypeptide having protease activity comprising an amino acid sequence of SEQ ID NO: 39, wherein the polypeptide having protease activity is covalently or non-covalently conjugated to a variant Fc polypeptide, wherein the variant Fc polypeptide comprises an amino acid sequence of SEQ ID NO: 25.

In some embodiments, a polypeptide comprises a polypeptide having protease activity comprising an amino acid sequence of SEQ ID NO: 39, wherein the polypeptide having protease activity is covalently or non-covalently conjugated to a variant Fc polypeptide, wherein the variant Fc polypeptide comprises an amino acid sequence of SEQ ID NO: 42.

In some embodiments, a polypeptide comprises a polypeptide having protease activity comprising an amino acid sequence of SEQ ID NO: 39, wherein the polypeptide having protease activity is covalently or non-covalently conjugated to a variant Fc polypeptide, wherein the variant Fc polypeptide comprises an amino acid sequence of SEQ ID NO: 43.

In some embodiments, a polypeptide comprises a polypeptide having protease activity comprising an amino acid sequence of SEQ ID NO: 39, wherein the polypeptide having protease activity is covalently or non-covalently conjugated to a variant Fc polypeptide, wherein the variant Fc polypeptide comprises an amino acid sequence of SEQ ID NO: 44.

In some embodiments, a polypeptide comprises a polypeptide having protease activity comprising an amino acid sequence of SEQ ID NO: 39, wherein the polypeptide having protease activity is covalently or non-covalently conjugated to a variant Fc polypeptide, wherein the variant Fc polypeptide comprises an amino acid sequence of SEQ ID NO: 45.

In some embodiments, a polypeptide comprises a polypeptide having protease activity comprising an amino acid sequence of SEQ ID NO: 39, wherein the polypeptide having protease activity is covalently or non-covalently conjugated to a variant Fc polypeptide, wherein the variant Fc polypeptide comprises an amino acid sequence of SEQ ID NO: 46.

In some embodiments, a polypeptide comprises a polypeptide having protease activity comprising an amino acid sequence of SEQ ID NO: 39, wherein the polypeptide having protease activity is covalently or non-covalently conjugated to a variant Fc polypeptide, wherein the variant Fc polypeptide comprises an amino acid sequence of SEQ ID NO: 47.

In some embodiments, a polypeptide comprises a polypeptide having protease activity comprising an amino acid sequence of SEQ ID NO: 39, wherein the polypeptide having protease activity is covalently or non-covalently conjugated to a variant Fc polypeptide, wherein the variant Fc polypeptide comprises an amino acid sequence of SEQ ID NO: 48.

In some embodiments, a polypeptide comprises a polypeptide having protease activity comprising an amino acid sequence of SEQ ID NO: 39, wherein the polypeptide having protease activity is covalently or non-covalently conjugated to a variant Fc polypeptide, wherein the variant Fc polypeptide comprises an amino acid sequence of SEQ ID NO: 49.

In some embodiments, a polypeptide comprises a polypeptide having protease activity comprising an amino acid sequence of SEQ ID NO: 40, wherein the polypeptide having protease activity is covalently or non-covalently conjugated to a variant Fc polypeptide, wherein the variant Fc polypeptide comprises an amino acid sequence of SEQ ID NO: 19.

In some embodiments, a polypeptide comprises a polypeptide having protease activity comprising an amino acid sequence of SEQ ID NO: 40, wherein the polypeptide having protease variant Fc polypeptide comprises an amino acid sequence of SEQ ID NO: 20.

In some embodiments, a polypeptide comprises a polypeptide having protease activity comprising an amino acid sequence of SEQ ID NO: 40, wherein the polypeptide having protease activity is covalently or non-covalently conjugated to a variant Fc polypeptide, wherein the variant Fc polypeptide comprises an amino acid sequence of SEQ ID NO: 21.

In some embodiments, a polypeptide comprises a polypeptide having protease activity comprising an amino acid sequence of SEQ ID NO: 40, wherein the polypeptide having protease activity is covalently or non-covalently conjugated to a variant Fc polypeptide, wherein the variant Fc polypeptide comprises an amino acid sequence of SEQ ID NO: 22.

In some embodiments, a polypeptide comprises a polypeptide having protease activity comprising an amino acid sequence of SEQ ID NO: 40, wherein the polypeptide having protease activity is covalently or non-covalently conjugated to a variant Fc polypeptide, wherein the variant Fc polypeptide comprises an amino acid sequence of SEQ ID NO: 23.

In some embodiments, a polypeptide comprises a polypeptide having protease activity comprising an amino acid sequence of SEQ ID NO: 40, wherein the polypeptide having protease activity is covalently or non-covalently conjugated to a variant Fc polypeptide, wherein the variant Fc polypeptide comprises an amino acid sequence of SEQ ID NO: 24.

In some embodiments, a polypeptide comprises a polypeptide having protease activity comprising an amino acid sequence of SEQ ID NO: 40, wherein the polypeptide having protease activity is covalently or non-covalently conjugated to a variant Fc polypeptide, wherein the variant Fc polypeptide comprises an amino acid sequence of SEQ ID NO: 25.

In some embodiments, a polypeptide comprises a polypeptide having protease activity comprising an amino acid sequence of SEQ ID NO: 40, wherein the polypeptide having protease activity is covalently or non-covalently conjugated to a variant Fc polypeptide, wherein the variant Fc polypeptide comprises an amino acid sequence of SEQ ID NO: 42.

In some embodiments, a polypeptide comprises a polypeptide having protease activity comprising an amino acid sequence of SEQ ID NO: 40, wherein the polypeptide having protease activity is covalently or non-covalently conjugated to a variant Fc polypeptide, wherein the variant Fc polypeptide comprises an amino acid sequence of SEQ ID NO: 43.

In some embodiments, a polypeptide comprises a polypeptide having protease activity comprising an amino acid sequence of SEQ ID NO: 40, wherein the polypeptide having protease activity is covalently or non-covalently conjugated to a variant Fc polypeptide, wherein the variant Fc polypeptide comprises an amino acid sequence of SEQ ID NO: 44.

In some embodiments, a polypeptide comprises a polypeptide having protease activity comprising an amino acid sequence of SEQ ID NO: 40, wherein the polypeptide having protease activity is covalently or non-covalently conjugated to a variant Fc polypeptide, wherein the variant Fc polypeptide comprises an amino acid sequence of SEQ ID NO: 45.

In some embodiments, a polypeptide comprises a polypeptide having protease activity comprising an amino acid sequence of SEQ ID NO: 40, wherein the polypeptide having protease activity is covalently or non-covalently conjugated to a variant Fc polypeptide, wherein the variant Fc polypeptide comprises an amino acid sequence of SEQ ID NO: 46.

In some embodiments, a polypeptide comprises a polypeptide having protease activity comprising an amino acid sequence of SEQ ID NO: 40, wherein the polypeptide having protease activity is covalently or non-covalently conjugated to a variant Fc polypeptide, wherein the variant Fc polypeptide comprises an amino acid sequence of SEQ ID NO: 47.

In some embodiments, a polypeptide comprises a polypeptide having protease activity comprising an amino acid sequence of SEQ ID NO: 40, wherein the polypeptide having protease activity is covalently or non-covalently conjugated to a variant Fc polypeptide, wherein the variant Fc polypeptide comprises an amino acid sequence of SEQ ID NO: 48.

In some embodiments, a polypeptide comprises a polypeptide having protease activity comprising an amino acid sequence of SEQ ID NO: 40, wherein the polypeptide having protease activity is covalently or non-covalently conjugated to a variant Fc polypeptide, wherein the variant Fc polypeptide comprises an amino acid sequence of SEQ ID NO: 49. In some embodiments, a polypeptide comprises a polypeptide having protease activity comprising an amino acid sequence of SEQ ID NO: 41, wherein the polypeptide having protease activity is covalently or non-covalently conjugated to a variant Fc polypeptide, wherein the variant Fc polypeptide comprises an amino acid sequence of SEQ ID NO: 19.

In some embodiments, a polypeptide comprises a polypeptide having protease activity comprising an amino acid sequence of SEQ ID NO: 41, wherein the polypeptide having protease variant Fc polypeptide comprises an amino acid sequence of SEQ ID NO: 20.

In some embodiments, a polypeptide comprises a polypeptide having protease activity comprising an amino acid sequence of SEQ ID NO: 41, wherein the polypeptide having protease activity is covalently or non-covalently conjugated to a variant Fc polypeptide, wherein the variant Fc polypeptide comprises an amino acid sequence of SEQ ID NO: 21.

In some embodiments, a polypeptide comprises a polypeptide having protease activity comprising an amino acid sequence of SEQ ID NO: 41, wherein the polypeptide having protease activity is covalently or non-covalently conjugated to a variant Fc polypeptide, wherein the variant Fc polypeptide comprises an amino acid sequence of SEQ ID NO: 22.

In some embodiments, a polypeptide comprises a polypeptide having protease activity comprising an amino acid sequence of SEQ ID NO: 41, wherein the polypeptide having protease activity is covalently or non-covalently conjugated to a variant Fc polypeptide, wherein the variant Fc polypeptide comprises an amino acid sequence of SEQ ID NO: 23.

In some embodiments, a polypeptide comprises a polypeptide having protease activity comprising an amino acid sequence of SEQ ID NO: 41, wherein the polypeptide having protease activity is covalently or non-covalently conjugated to a variant Fc polypeptide, wherein the variant Fc polypeptide comprises an amino acid sequence of SEQ ID NO: 24.

In some embodiments, a polypeptide comprises a polypeptide having protease activity comprising an amino acid sequence of SEQ ID NO: 41, wherein the polypeptide having protease activity is covalently or non-covalently conjugated to a variant Fc polypeptide, wherein the variant Fc polypeptide comprises an amino acid sequence of SEQ ID NO: 25.

In some embodiments, a polypeptide comprises a polypeptide having protease activity comprising an amino acid sequence of SEQ ID NO: 41, wherein the polypeptide having protease activity is covalently or non-covalently conjugated to a variant Fc polypeptide, wherein the variant Fc polypeptide comprises an amino acid sequence of SEQ ID NO: 42.

In some embodiments, a polypeptide comprises a polypeptide having protease activity comprising an amino acid sequence of SEQ ID NO: 41, wherein the polypeptide having protease activity is covalently or non-covalently conjugated to a variant Fc polypeptide, wherein the variant Fc polypeptide comprises an amino acid sequence of SEQ ID NO: 43.

In some embodiments, a polypeptide comprises a polypeptide having protease activity comprising an amino acid sequence of SEQ ID NO: 41, wherein the polypeptide having protease activity is covalently or non-covalently conjugated to a variant Fc polypeptide, wherein the variant Fc polypeptide comprises an amino acid sequence of SEQ ID NO: 44.

In some embodiments, a polypeptide comprises a polypeptide having protease activity comprising an amino acid sequence of SEQ ID NO: 41, wherein the polypeptide having protease activity is covalently or non-covalently conjugated to a variant Fc polypeptide, wherein the variant Fc polypeptide comprises an amino acid sequence of SEQ ID NO: 45.

In some embodiments, a polypeptide comprises a polypeptide having protease activity comprising an amino acid sequence of SEQ ID NO: 41, wherein the polypeptide having protease activity is covalently or non-covalently conjugated to a variant Fc polypeptide, wherein the variant Fc polypeptide comprises an amino acid sequence of SEQ ID NO: 46.

In some embodiments, a polypeptide comprises a polypeptide having protease activity comprising an amino acid sequence of SEQ ID NO: 41, wherein the polypeptide having protease activity is covalently or non-covalently conjugated to a variant Fc polypeptide, wherein the variant Fc polypeptide comprises an amino acid sequence of SEQ ID NO: 47.

In some embodiments, a polypeptide comprises a polypeptide having protease activity comprising an amino acid sequence of SEQ ID NO: 41, wherein the polypeptide having protease activity is covalently or non-covalently conjugated to a variant Fc polypeptide, wherein the variant Fc polypeptide comprises an amino acid sequence of SEQ ID NO: 48.

In some embodiments, a polypeptide comprises a polypeptide having protease activity comprising an amino acid sequence of SEQ ID NO: 41, wherein the polypeptide having protease activity is covalently or non-covalently conjugated to a variant Fc polypeptide, wherein the variant Fc polypeptide comprises an amino acid sequence of SEQ ID NO: 49.

In some embodiments, a polypeptide comprises a polypeptide having protease activity comprising an amino acid sequence of SEQ ID NO: 50, wherein the polypeptide having protease activity is covalently or non-covalently conjugated to a variant Fc polypeptide, wherein the variant Fc polypeptide comprises an amino acid sequence of SEQ ID NO: 19.

In some embodiments, a polypeptide comprises a polypeptide having protease activity comprising an amino acid sequence of SEQ ID NO: 50, wherein the polypeptide having protease variant Fc polypeptide comprises an amino acid sequence of SEQ ID NO: 20.

In some embodiments, a polypeptide comprises a polypeptide having protease activity comprising an amino acid sequence of SEQ ID NO: 50, wherein the polypeptide having protease activity is covalently or non-covalently conjugated to a variant Fc polypeptide, wherein the variant Fc polypeptide comprises an amino acid sequence of SEQ ID NO: 21.

In some embodiments, a polypeptide comprises a polypeptide having protease activity comprising an amino acid sequence of SEQ ID NO: 50, wherein the polypeptide having protease activity is covalently or non-covalently conjugated to a variant Fc polypeptide, wherein the variant Fc polypeptide comprises an amino acid sequence of SEQ ID NO: 22.

In some embodiments, a polypeptide comprises a polypeptide having protease activity comprising an amino acid sequence of SEQ ID NO: 50, wherein the polypeptide having protease activity is covalently or non-covalently conjugated to a variant Fc polypeptide, wherein the variant Fc polypeptide comprises an amino acid sequence of SEQ ID NO: 23.

In some embodiments, a polypeptide comprises a polypeptide having protease activity comprising an amino acid sequence of SEQ ID NO: 50, wherein the polypeptide having protease activity is covalently or non-covalently conjugated to a variant Fc polypeptide, wherein the variant Fc polypeptide comprises an amino acid sequence of SEQ ID NO: 24.

In some embodiments, a polypeptide comprises a polypeptide having protease activity comprising an amino acid sequence of SEQ ID NO: 50, wherein the polypeptide having protease activity is covalently or non-covalently conjugated to a variant Fc polypeptide, wherein the variant Fc polypeptide comprises an amino acid sequence of SEQ ID NO: 25.

In some embodiments, a polypeptide comprises a polypeptide having protease activity comprising an amino acid sequence of SEQ ID NO: 50, wherein the polypeptide having protease activity is covalently or non-covalently conjugated to a variant Fc polypeptide, wherein the variant Fc polypeptide comprises an amino acid sequence of SEQ ID NO: 42.

In some embodiments, a polypeptide comprises a polypeptide having protease activity comprising an amino acid sequence of SEQ ID NO: 50, wherein the polypeptide having protease activity is covalently or non-covalently conjugated to a variant Fc polypeptide, wherein the variant Fc polypeptide comprises an amino acid sequence of SEQ ID NO: 43.

In some embodiments, a polypeptide comprises a polypeptide having protease activity comprising an amino acid sequence of SEQ ID NO: 50, wherein the polypeptide having protease activity is covalently or non-covalently conjugated to a variant Fc polypeptide, wherein the variant Fc polypeptide comprises an amino acid sequence of SEQ ID NO: 44.

In some embodiments, a polypeptide comprises a polypeptide having protease activity comprising an amino acid sequence of SEQ ID NO: 50, wherein the polypeptide having protease activity is covalently or non-covalently conjugated to a variant Fc polypeptide, wherein the variant Fc polypeptide comprises an amino acid sequence of SEQ ID NO: 45.

In some embodiments, a polypeptide comprises a polypeptide having protease activity comprising an amino acid sequence of SEQ ID NO: 50, wherein the polypeptide having protease activity is covalently or non-covalently conjugated to a variant Fc polypeptide, wherein the variant Fc polypeptide comprises an amino acid sequence of SEQ ID NO: 46.

In some embodiments, a polypeptide comprises a polypeptide having protease activity comprising an amino acid sequence of SEQ ID NO: 50, wherein the polypeptide having protease activity is covalently or non-covalently conjugated to a variant Fc polypeptide, wherein the variant Fc polypeptide comprises an amino acid sequence of SEQ ID NO: 47.

In some embodiments, a polypeptide comprises a polypeptide having protease activity comprising an amino acid sequence of SEQ ID NO: 50, wherein the polypeptide having protease activity is covalently or non-covalently conjugated to a variant Fc polypeptide, wherein the variant Fc polypeptide comprises an amino acid sequence of SEQ ID NO: 48.

In some embodiments, a polypeptide comprises a polypeptide having protease activity comprising an amino acid sequence of SEQ ID NO: 50, wherein the polypeptide having protease activity is covalently or non-covalently conjugated to a variant Fc polypeptide, wherein the variant Fc polypeptide comprises an amino acid sequence of SEQ ID NO: 49.

In some embodiments, a polypeptide comprises a polypeptide having protease activity comprising an amino acid sequence of SEQ ID NO: 51, wherein the polypeptide having protease activity is covalently or non-covalently conjugated to a variant Fc polypeptide, wherein the variant Fc polypeptide comprises an amino acid sequence of SEQ ID NO: 19.

In some embodiments, a polypeptide comprises a polypeptide having protease activity comprising an amino acid sequence of SEQ ID NO: 51, wherein the polypeptide having protease variant Fc polypeptide comprises an amino acid sequence of SEQ ID NO: 20.

In some embodiments, a polypeptide comprises a polypeptide having protease activity comprising an amino acid sequence of SEQ ID NO: 51, wherein the polypeptide having protease activity is covalently or non-covalently conjugated to a variant Fc polypeptide, wherein the variant Fc polypeptide comprises an amino acid sequence of SEQ ID NO: 21.

In some embodiments, a polypeptide comprises a polypeptide having protease activity comprising an amino acid sequence of SEQ ID NO: 51, wherein the polypeptide having protease activity is covalently or non-covalently conjugated to a variant Fc polypeptide, wherein the variant Fc polypeptide comprises an amino acid sequence of SEQ ID NO: 22.

In some embodiments, a polypeptide comprises a polypeptide having protease activity comprising an amino acid sequence of SEQ ID NO: 51, wherein the polypeptide having protease activity is covalently or non-covalently conjugated to a variant Fc polypeptide, wherein the variant Fc polypeptide comprises an amino acid sequence of SEQ ID NO: 23.

In some embodiments, a polypeptide comprises a polypeptide having protease activity comprising an amino acid sequence of SEQ ID NO: 51, wherein the polypeptide having protease activity is covalently or non-covalently conjugated to a variant Fc polypeptide, wherein the variant Fc polypeptide comprises an amino acid sequence of SEQ ID NO: 24.

In some embodiments, a polypeptide comprises a polypeptide having protease activity comprising an amino acid sequence of SEQ ID NO: 51, wherein the polypeptide having protease activity is covalently or non-covalently conjugated to a variant Fc polypeptide, wherein the variant Fc polypeptide comprises an amino acid sequence of SEQ ID NO: 25.

In some embodiments, a polypeptide comprises a polypeptide having protease activity comprising an amino acid sequence of SEQ ID NO: 51, wherein the polypeptide having protease activity is covalently or non-covalently conjugated to a variant Fc polypeptide, wherein the variant Fc polypeptide comprises an amino acid sequence of SEQ ID NO: 42.

In some embodiments, a polypeptide comprises a polypeptide having protease activity comprising an amino acid sequence of SEQ ID NO: 51, wherein the polypeptide having protease activity is covalently or non-covalently conjugated to a variant Fc polypeptide, wherein the variant Fc polypeptide comprises an amino acid sequence of SEQ ID NO: 43.

In some embodiments, a polypeptide comprises a polypeptide having protease activity comprising an amino acid sequence of SEQ ID NO: 51, wherein the polypeptide having protease activity is covalently or non-covalently conjugated to a variant Fc polypeptide, wherein the variant Fc polypeptide comprises an amino acid sequence of SEQ ID NO: 44.

In some embodiments, a polypeptide comprises a polypeptide having protease activity comprising an amino acid sequence of SEQ ID NO: 51, wherein the polypeptide having protease activity is covalently or non-covalently conjugated to a variant Fc polypeptide, wherein the variant Fc polypeptide comprises an amino acid sequence of SEQ ID NO: 45.

In some embodiments, a polypeptide comprises a polypeptide having protease activity comprising an amino acid sequence of SEQ ID NO: 51, wherein the polypeptide having protease activity is covalently or non-covalently conjugated to a variant Fc polypeptide, wherein the variant Fc polypeptide comprises an amino acid sequence of SEQ ID NO: 46.

In some embodiments, a polypeptide comprises a polypeptide having protease activity comprising an amino acid sequence of SEQ ID NO: 51, wherein the polypeptide having protease activity is covalently or non-covalently conjugated to a variant Fc polypeptide, wherein the variant Fc polypeptide comprises an amino acid sequence of SEQ ID NO: 47.

In some embodiments, a polypeptide comprises a polypeptide having protease activity comprising an amino acid sequence of SEQ ID NO: 51, wherein the polypeptide having protease activity is covalently or non-covalently conjugated to a variant Fc polypeptide, wherein the variant Fc polypeptide comprises an amino acid sequence of SEQ ID NO: 48.

In some embodiments, a polypeptide comprises a polypeptide having protease activity comprising an amino acid sequence of SEQ ID NO: 51, wherein the polypeptide having protease activity is covalently or non-covalently conjugated to a variant Fc polypeptide, wherein the variant Fc polypeptide comprises an amino acid sequence of SEQ ID NO: 49.

In some embodiments, a polypeptide comprises a polypeptide having protease activity comprising an amino acid sequence of SEQ ID NO: 52, wherein the polypeptide having protease activity is covalently or non-covalently conjugated to a variant Fc polypeptide, wherein the variant Fc polypeptide comprises an amino acid sequence of SEQ ID NO: 19.

In some embodiments, a polypeptide comprises a polypeptide having protease activity comprising an amino acid sequence of SEQ ID NO: 52, wherein the polypeptide having protease variant Fc polypeptide comprises an amino acid sequence of SEQ ID NO: 20.

In some embodiments, a polypeptide comprises a polypeptide having protease activity comprising an amino acid sequence of SEQ ID NO: 52, wherein the polypeptide having protease activity is covalently or non-covalently conjugated to a variant Fc polypeptide, wherein the variant Fc polypeptide comprises an amino acid sequence of SEQ ID NO: 21.

In some embodiments, a polypeptide comprises a polypeptide having protease activity comprising an amino acid sequence of SEQ ID NO: 52, wherein the polypeptide having protease activity is covalently or non-covalently conjugated to a variant Fc polypeptide, wherein the variant Fc polypeptide comprises an amino acid sequence of SEQ ID NO: 22.

In some embodiments, a polypeptide comprises a polypeptide having protease activity comprising an amino acid sequence of SEQ ID NO: 52, wherein the polypeptide having protease activity is covalently or non-covalently conjugated to a variant Fc polypeptide, wherein the variant Fc polypeptide comprises an amino acid sequence of SEQ ID NO: 23.

In some embodiments, a polypeptide comprises a polypeptide having protease activity comprising an amino acid sequence of SEQ ID NO: 52, wherein the polypeptide having protease activity is covalently or non-covalently conjugated to a variant Fc polypeptide, wherein the variant Fc polypeptide comprises an amino acid sequence of SEQ ID NO: 24.

In some embodiments, a polypeptide comprises a polypeptide having protease activity comprising an amino acid sequence of SEQ ID NO: 52, wherein the polypeptide having protease activity is covalently or non-covalently conjugated to a variant Fc polypeptide, wherein the variant Fc polypeptide comprises an amino acid sequence of SEQ ID NO: 25.

In some embodiments, a polypeptide comprises a polypeptide having protease activity comprising an amino acid sequence of SEQ ID NO: 52, wherein the polypeptide having protease activity is covalently or non-covalently conjugated to a variant Fc polypeptide, wherein the variant Fc polypeptide comprises an amino acid sequence of SEQ ID NO: 42.

In some embodiments, a polypeptide comprises a polypeptide having protease activity comprising an amino acid sequence of SEQ ID NO: 52, wherein the polypeptide having protease activity is covalently or non-covalently conjugated to a variant Fc polypeptide, wherein the variant Fc polypeptide comprises an amino acid sequence of SEQ ID NO: 43.

In some embodiments, a polypeptide comprises a polypeptide having protease activity comprising an amino acid sequence of SEQ ID NO: 52, wherein the polypeptide having protease activity is covalently or non-covalently conjugated to a variant Fc polypeptide, wherein the variant Fc polypeptide comprises an amino acid sequence of SEQ ID NO: 44.

In some embodiments, a polypeptide comprises a polypeptide having protease activity comprising an amino acid sequence of SEQ ID NO: 52, wherein the polypeptide having protease activity is covalently or non-covalently conjugated to a variant Fc polypeptide, wherein the variant Fc polypeptide comprises an amino acid sequence of SEQ ID NO: 45.

In some embodiments, a polypeptide comprises a polypeptide having protease activity comprising an amino acid sequence of SEQ ID NO: 52, wherein the polypeptide having protease activity is covalently or non-covalently conjugated to a variant Fc polypeptide, wherein the variant Fc polypeptide comprises an amino acid sequence of SEQ ID NO: 46.

In some embodiments, a polypeptide comprises a polypeptide having protease activity comprising an amino acid sequence of SEQ ID NO: 52, wherein the polypeptide having protease activity is covalently or non-covalently conjugated to a variant Fc polypeptide, wherein the variant Fc polypeptide comprises an amino acid sequence of SEQ ID NO: 47.

In some embodiments, a polypeptide comprises a polypeptide having protease activity comprising an amino acid sequence of SEQ ID NO: 52, wherein the polypeptide having protease activity is covalently or non-covalently conjugated to a variant Fc polypeptide, wherein the variant Fc polypeptide comprises an amino acid sequence of SEQ ID NO: 48.

In some embodiments, a polypeptide comprises a polypeptide having protease activity comprising an amino acid sequence of SEQ ID NO: 52, wherein the polypeptide having protease activity is covalently or non-covalently conjugated to a variant Fc polypeptide, wherein the variant Fc polypeptide comprises an amino acid sequence of SEQ ID NO: 49.

In some embodiments, a polypeptide comprises a polypeptide having protease activity comprising an amino acid sequence of SEQ ID NO: 55, wherein the polypeptide having protease activity is covalently or non-covalently conjugated to a variant Fc polypeptide, wherein the variant Fc polypeptide comprises an amino acid sequence of SEQ ID NO: 19.

In some embodiments, a polypeptide comprises a polypeptide having protease activity comprising an amino acid sequence of SEQ ID NO: 55, wherein the polypeptide having protease variant Fc polypeptide comprises an amino acid sequence of SEQ ID NO: 20.

In some embodiments, a polypeptide comprises a polypeptide having protease activity comprising an amino acid sequence of SEQ ID NO: 55, wherein the polypeptide having protease activity is covalently or non-covalently conjugated to a variant Fc polypeptide, wherein the variant Fc polypeptide comprises an amino acid sequence of SEQ ID NO: 21.

In some embodiments, a polypeptide comprises a polypeptide having protease activity comprising an amino acid sequence of SEQ ID NO: 55, wherein the polypeptide having protease activity is covalently or non-covalently conjugated to a variant Fc polypeptide, wherein the variant Fc polypeptide comprises an amino acid sequence of SEQ ID NO: 22.

In some embodiments, a polypeptide comprises a polypeptide having protease activity comprising an amino acid sequence of SEQ ID NO: 55, wherein the polypeptide having protease activity is covalently or non-covalently conjugated to a variant Fc polypeptide, wherein the variant Fc polypeptide comprises an amino acid sequence of SEQ ID NO: 23.

In some embodiments, a polypeptide comprises a polypeptide having protease activity comprising an amino acid sequence of SEQ ID NO: 55, wherein the polypeptide having protease activity is covalently or non-covalently conjugated to a variant Fc polypeptide, wherein the variant Fc polypeptide comprises an amino acid sequence of SEQ ID NO: 24.

In some embodiments, a polypeptide comprises a polypeptide having protease activity comprising an amino acid sequence of SEQ ID NO: 55, wherein the polypeptide having protease activity is covalently or non-covalently conjugated to a variant Fc polypeptide, wherein the variant Fc polypeptide comprises an amino acid sequence of SEQ ID NO: 25.

In some embodiments, a polypeptide comprises a polypeptide having protease activity comprising an amino acid sequence of SEQ ID NO: 55, wherein the polypeptide having protease activity is covalently or non-covalently conjugated to a variant Fc polypeptide, wherein the variant Fc polypeptide comprises an amino acid sequence of SEQ ID NO: 42.

In some embodiments, a polypeptide comprises a polypeptide having protease activity comprising an amino acid sequence of SEQ ID NO: 55, wherein the polypeptide having protease activity is covalently or non-covalently conjugated to a variant Fc polypeptide, wherein the variant Fc polypeptide comprises an amino acid sequence of SEQ ID NO: 43.

In some embodiments, a polypeptide comprises a polypeptide having protease activity comprising an amino acid sequence of SEQ ID NO: 55, wherein the polypeptide having protease activity is covalently or non-covalently conjugated to a variant Fc polypeptide, wherein the variant Fc polypeptide comprises an amino acid sequence of SEQ ID NO: 44.

In some embodiments, a polypeptide comprises a polypeptide having protease activity comprising an amino acid sequence of SEQ ID NO: 55, wherein the polypeptide having protease activity is covalently or non-covalently conjugated to a variant Fc polypeptide, wherein the variant Fc polypeptide comprises an amino acid sequence of SEQ ID NO: 45.

In some embodiments, a polypeptide comprises a polypeptide having protease activity comprising an amino acid sequence of SEQ ID NO: 55, wherein the polypeptide having protease activity is covalently or non-covalently conjugated to a variant Fc polypeptide, wherein the variant Fc polypeptide comprises an amino acid sequence of SEQ ID NO: 46.

In some embodiments, a polypeptide comprises a polypeptide having protease activity comprising an amino acid sequence of SEQ ID NO: 55, wherein the polypeptide having protease activity is covalently or non-covalently conjugated to a variant Fc polypeptide, wherein the variant Fc polypeptide comprises an amino acid sequence of SEQ ID NO: 47.

In some embodiments, a polypeptide comprises a polypeptide having protease activity comprising an amino acid sequence of SEQ ID NO: 55, wherein the polypeptide having protease activity is covalently or non-covalently conjugated to a variant Fc polypeptide, wherein the variant Fc polypeptide comprises an amino acid sequence of SEQ ID NO: 48.

In some embodiments, a polypeptide comprises a polypeptide having protease activity comprising an amino acid sequence of SEQ ID NO: 55, wherein the polypeptide having protease activity is covalently or non-covalently conjugated to a variant Fc polypeptide, wherein the variant Fc polypeptide comprises an amino acid sequence of SEQ ID NO: 49.

In some embodiments, a polypeptide comprises a polypeptide having protease activity covalently or non-covalently conjugated to a variant Fc polypeptide, wherein the variant Fc polypeptide comprises an amino acid sequence having a C-terminal lysine (K).

In some embodiments, a polypeptide comprises a polypeptide having protease activity covalently or non-covalently conjugated to a variant Fc polypeptide, wherein the variant Fc polypeptide comprises an amino acid sequence not having a C-terminal lysine (K).

In some embodiments, a histidine tag comprises an amino acid sequence of SEQ ID NO: 27, or 34. In some embodiments, the histidine tag comprises an amino acid sequence of SEQ ID NO: 27.

In some embodiments, a polypeptide has the formula from N-terminus to C-terminus:

P1-variant Fc, wherein,
P1 comprises a polypeptide having protease activity; and
variant Fc is any variant IgG Fc provided herein.

In some embodiments, a polypeptide has the formula from N-terminus to C-terminus:

variant Fc-P1, wherein,
P1 comprises a polypeptide having protease activity; and
variant Fc is any variant IgG Fc provided herein.

In some embodiments, a polypeptide has the formula from N-terminus to C-terminus:

P1-variant Fc, wherein,
P1 comprises a polypeptide having protease activity;
variant Fc is any variant IgG Fc provided herein; and
optionally wherein the protease is a glycosylation-resistant protease.

In some embodiments, a polypeptide has the formula from N-terminus to C-terminus:

variant Fc-P1, wherein,
P1 comprises a polypeptide having protease activity;
variant Fc is any variant IgG Fc provided herein; and
optionally wherein the protease is a glycosylation-resistant protease.

In some embodiments, a polypeptide has the formula from N-terminus to C-terminus:

N1-P1-variant Fc, wherein,
P1 comprises a polypeptide having protease activity;
N1 comprises a nanobody; and
variant Fc is any variant IgG Fc provided herein.

In some embodiments, a polypeptide has the formula from N-terminus to C-terminus:

variant Fc-P1-N1, wherein,
P1 comprises a polypeptide having protease activity;
N1 comprises a nanobody; and
variant Fc is any variant IgG Fc provided herein.

In some embodiments, a polypeptide has the formula from N-terminus to C-terminus:

N1-variant Fc-P1, wherein,
P1 comprises a polypeptide having protease activity;
N1 comprises a nanobody; and
variant Fc is any variant IgG Fc provided herein.

In some embodiments, a polypeptide has the formula from N-terminus to C-terminus:

P1-variant Fc-N1, wherein,
P1 comprises a polypeptide having protease activity;
N1 comprises a nanobody; and
variant Fc is any variant IgG Fc provided herein.

In some embodiments, a polypeptide has the formula from N-terminus to C-terminus:

P1-N1, wherein,
P1 comprises a polypeptide having protease activity; and
N1 comprises a nanobody.

In some embodiments, a polypeptide has the formula from N-terminus to C-terminus:

N1-P1, wherein,
P1 comprises a polypeptide having protease activity; and
N1 comprises a nanobody.

In some embodiments, a polypeptide has the formula from N-terminus to C-terminus:

N1-P1-variant Fc, wherein,
P1 comprises a polypeptide having protease activity;
N1 comprises a nanobody; and
variant Fc is any variant IgG Fc provided herein; and
optionally wherein the protease is a glycosylation-resistant protease.

In some embodiments, a polypeptide has the formula from N-terminus to C-terminus:

variant Fc-P1-N1, wherein,
P1 comprises a polypeptide having protease activity;
N1 comprises a nanobody; and
variant Fc is any variant IgG Fc provided herein; and
optionally wherein the protease is a glycosylation-resistant protease.

In some embodiments, a polypeptide has the formula from N-terminus to C-terminus:

N1-variant Fc-P1, wherein,
P1 comprises a polypeptide having protease activity;
N1 comprises a nanobody; and
variant Fc is any variant IgG Fc provided herein; and
optionally wherein the protease is a glycosylation-resistant protease.

In some embodiments, a polypeptide has the formula from N-terminus to C-terminus:

P1-variant Fc-N1, wherein,
P1 comprises a polypeptide having protease activity;
N1 comprises a nanobody; and
variant Fc is any variant IgG Fc provided herein; and
optionally wherein the protease is a glycosylation-resistant protease.

In some embodiments, a polypeptide has the formula from N-terminus to C-terminus:

P1-N1, wherein,
P1 comprises a polypeptide having protease activity; and
N1 comprises a nanobody; and
optionally wherein the protease is a glycosylation-resistant protease.

In some embodiments, a polypeptide has the formula from N-terminus to C-terminus:

N1-P1.

wherein,
P1 comprises a polypeptide having protease activity; and
N1 comprises a nanobody; and
optionally wherein the protease is a glycosylation-resistant protease.

In some embodiments, P1, and variant Fc are covalently or non-covalently conjugated to each other, as according to the above formulas. In some embodiments, P1, N1, and variant Fc are covalently or non-covalently conjugated to each other, as according to the above formulas.

In some embodiments, P1 comprises a polypeptide having protease activity. In some embodiments, N1 comprises a nanobody. In some embodiments, P1 comprises a polypeptide having protease activity, and N1 comprises a nanobody.

In some embodiments, P1 comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any sequence provided in Table 4. In some embodiments, P1 comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, 28, 29, 31, 36, 37, 38, 39, 40, 41, 50, 51, 52, or 55. In some embodiments, P1 comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26. In some embodiments, P1 comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28. In some embodiments, P1 comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29. In some embodiments, P1 comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31. In some embodiments. P1 comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36. In some embodiments, P1 comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37. In some embodiments, P1 comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38. In some embodiments, P1 comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39. In some embodiments, P1 comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40. In some embodiments, P1 comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41. In some embodiments, P1 comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50. In some embodiments, P1 comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51. In some embodiments. P1 comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52. In some embodiments, P1 comprises a polypeptide having protease activity comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55.

In some embodiments, P1 comprises a polypeptide having protease activity comprising any sequence provided in Table 4. In some embodiments, P1 comprises a polypeptide having protease activity comprising an amino acid sequence of SEQ ID NO: 26, 28, 29, 31, 36, 37, 38, 39, 40, 41, 50, 51, 52, or 55. In some embodiments, P1 comprises a polypeptide having protease activity comprising an amino acid sequence of SEQ ID NO: 26. In some embodiments, P1 comprises a polypeptide having protease activity comprising an amino acid sequence of SEQ ID NO: 28. In some embodiments, P1 comprises a polypeptide having protease activity comprising an amino acid sequence of SEQ ID NO: 29. In some embodiments, P1 comprises a polypeptide having protease activity comprising an amino acid sequence of SEQ ID NO: 31. In some embodiments, P1 comprises a polypeptide having protease activity comprising an amino acid sequence of SEQ ID NO: 36. In some embodiments, P1 comprises a polypeptide having protease activity comprising an amino acid sequence of SEQ ID NO: 37. In some embodiments, P1 comprises a polypeptide having protease activity comprising an amino acid sequence of SEQ ID NO: 38. In some embodiments, P1 comprises a polypeptide having protease activity comprising an amino acid sequence of SEQ ID NO: 39. In some embodiments, P1 comprises a polypeptide having protease activity comprising an amino acid sequence of SEQ ID NO: 40. In some embodiments, P1 comprises a polypeptide having protease activity comprising an amino acid sequence of SEQ ID NO: 41. In some embodiments, P1 comprises a polypeptide having protease activity comprising an amino acid sequence of SEQ ID NO: 50. In some embodiments, P1 comprises a polypeptide having protease activity comprising an amino acid sequence of SEQ ID NO: 51. In some embodiments, P1 comprises a polypeptide having protease activity comprising an amino acid sequence of SEQ ID NO: 52. In some embodiments, P1 comprises a polypeptide having protease activity comprising an amino acid sequence of SEQ ID NO: 55.

In some embodiments, P1 comprises an IdeS, IdeSsuis, IdeE, IdeZ, IdeZ2, IdeE2, or IdeC protease. In some embodiments, P1 comprises an IdeS protease comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, 28, 29, 31, 36, 50, or 51. In some embodiments, P1 comprises an IdeS protease comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26. In some embodiments, P1 comprises an IdeS protease comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28. In some embodiments, P1 comprises an IdeS protease comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29. In some embodiments, P1 comprises an IdeS protease comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31. In some embodiments, P1 comprises an IdeS protease comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36. In some embodiments, P1 comprises an IdeS protease comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50. In some embodiments, P1 comprises an IdeS protease comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51.

In some embodiments, P1 comprises an IdeS protease comprising an amino acid sequence of SEQ ID NO: 26, 28, 29, 31, 36, 50, or 51. In some embodiments, P1 comprises an IdeS protease comprising an amino acid sequence of SEQ ID NO: 26. In some embodiments, P1 comprises an IdeS protease comprising an amino acid sequence of SEQ ID NO: 28. In some embodiments, P1 comprises an IdeS protease comprising an amino acid sequence of SEQ ID NO: 29. In some embodiments. P1 comprises an IdeS protease comprising an amino acid sequence of SEQ ID NO: 31. In some embodiments, P1 comprises an IdeS protease comprising an amino acid sequence of SEQ ID NO: 36. In some embodiments, P1 comprises an IdeS protease comprising an amino acid sequence of SEQ ID NO: 50. In some embodiments, P1 comprises an IdeS protease comprising an amino acid sequence of SEQ ID NO: 51.

In some embodiments, P1 comprises an IdeSsuis protease comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 55. In some embodiments, P1 comprises an IdeSsuis protease comprising an amino acid sequence of SEQ ID NO: 55.

In some embodiments, P1 comprises an IdeE protease comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 37. In some embodiments, P1 comprises an IdeE protease comprising an amino acid sequence of SEQ ID NO: 37.

In some embodiments, P1 comprises an IdeZ protease comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38, or 52. In some embodiments, P1 comprises an IdeZ protease comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 38. In some embodiments, P1 comprises an IdeZ protease comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 52. In some embodiments, P1 comprises an IdeZ protease comprising an amino acid sequence of SEQ ID NO: 38, or 52. In some embodiments, P1 comprises an IdeZ protease comprising an amino acid sequence of SEQ ID NO: 38. In some embodiments, P1 comprises an IdeZ protease comprising an amino acid sequence of SEQ ID NO: 52.

In some embodiments, P1 comprises an IdeE2 protease comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 39. In some embodiments, P1 comprises an IdeE2 protease comprising an amino acid sequence of SEQ ID NO: 39.

In some embodiments, P1 comprises an IdeZ2 protease comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 40. In some embodiments, P1 comprises an IdeZ2 protease comprising an amino acid sequence of SEQ ID NO: 40.

In some embodiments, P1 comprises an IdeC protease comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 41. In some embodiments, P1 comprises an IdeC protease comprising an amino acid sequence of SEQ ID NO: 41.

In some embodiments, a polypeptide has the formula from N-terminus to C-terminus:

IdeS-variant Fc-N1, wherein,
N1 comprises a nanobody; and
variant Fc is any variant IgG Fc provided herein. In some embodiments, a polypeptide has the formula from N-terminus to C-terminus:

N1-variant Fc-IdeS, wherein,
N1 comprises a nanobody; and
variant Fc is any variant IgG Fc provided herein.

In some embodiments, a polypeptide has the formula from N-terminus to C-terminus:

variant Fc-IdeS-N1, wherein,
N1 comprises a nanobody; and
variant Fc is any variant IgG Fc provided herein.

In some embodiments, a polypeptide has the formula from N-terminus to C-terminus:

N1-IdeS-variant Fc, wherein,
N1 comprises a nanobody; and
variant Fc is any variant IgG Fc provided herein.

In some embodiments, a polypeptide has the formula from N-terminus to C-terminus:

N1-IdeS, wherein,
N1 comprises a nanobody.

In some embodiments, a polypeptide has the formula from N-terminus to C-terminus:

IdeS-N1, wherein,
N1 comprises a nanobody.

In some embodiments, IdeS comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26, 28, 29, 31, 36, 50, or 51. In some embodiments, IdeS comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 26. In some embodiments, IdeS comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 28. In some embodiments, IdeS comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 29. In some embodiments, IdeS comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 31. In some embodiments, IdeS comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 36. In some embodiments, IdeS comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 50. In some embodiments, IdeS comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 51.

In some embodiments, IdeS comprises an amino acid sequence of SEQ ID NO: 26, 28, 29, 31, 36, 50, or 51. In some embodiments, IdeS comprises an amino acid sequence of SEQ ID NO: 26. In some embodiments, IdeS comprises an amino acid sequence of SEQ ID NO: 28. In some embodiments, IdeS comprises an amino acid sequence of SEQ ID NO: 29. In some embodiments, IdeS comprises an amino acid sequence of SEQ ID NO: 31. In some embodiments, IdeS comprises an amino acid sequence of SEQ ID NO: 36. In some embodiments, IdeS comprises an amino acid sequence of SEQ ID NO: 50. In some embodiments, IdeS comprises an amino acid sequence of SEQ ID NO: 51.

In some embodiments, the variant Fc comprises a variant Fc polypeptide. In some embodiments, the variant Fc polypeptide is such as those provided herein. In some embodiments, the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19, 20, 21, 22, 23, 24, 25, 42, 43, 44, 45, 47, 48, or 49. In some embodiments, the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 19. In some embodiments, the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 20. In some embodiments, the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 21. In some embodiments, the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 22. In some embodiments, the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 23. In some embodiments, the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 24. In some embodiments, the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 25. In some embodiments, the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 42. In some embodiments, the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 43. In some embodiments, the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 44. In some embodiments, the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 45. In some embodiments, the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 46. In some embodiments, the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 47. In some embodiments, the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 48. In some embodiments, the variant Fc polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 49.

In some embodiments, the variant Fc polypeptide comprises an amino acid sequence of SEQ ID NO: 19, 20, 21, 22, 23, 24, 25, 42, 43, 44, 45, 47, 48, or 49. In some embodiments, the variant Fc polypeptide comprises an amino acid sequence of SEQ ID NO: 19. In some embodiments, the variant Fc polypeptide comprises an amino acid sequence of SEQ ID NO: 20. In some embodiments, the variant Fc polypeptide comprises an amino acid sequence of SEQ ID NO: 21. In some embodiments, the variant Fc polypeptide comprises an amino acid sequence of SEQ ID NO: 22. In some embodiments, the variant Fc polypeptide comprises an amino acid sequence of SEQ ID NO: 23. In some embodiments, the variant Fc polypeptide comprises an amino acid sequence of SEQ ID NO: 24. In some embodiments, the variant Fc polypeptide comprises an amino acid sequence of SEQ ID NO: 25. In some embodiments, the variant Fc polypeptide comprises an amino acid sequence of SEQ ID NO: 42. In some embodiments, the variant Fc polypeptide comprises an amino acid sequence of SEQ ID NO: 43. In some embodiments, the variant Fc polypeptide comprises an amino acid sequence of SEQ ID NO: 44. In some embodiments, the variant Fc polypeptide comprises an amino acid sequence of SEQ ID NO: 45. In some embodiments, the variant Fc polypeptide comprises an amino acid sequence of SEQ ID NO: 46. In some embodiments, the variant Fc polypeptide comprises an amino acid sequence of SEQ ID NO: 47. In some embodiments, the variant Fc polypeptide comprises an amino acid sequence of SEQ ID NO: 48. In some embodiments, the variant Fc polypeptide comprises an amino acid sequence of SEQ ID NO: 49.

In some embodiments, N1 comprises a nanobody comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 30, 32, or 33. In some embodiments, N1 comprises a nanobody comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 30. In some embodiments, N1 comprises a nanobody comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 32. In some embodiments, N1 comprises a nanobody comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 33.

In some embodiments, N1 comprises a nanobody comprising an amino acid sequence of SEQ ID NO: 30, 32, or 33. In some embodiments, N1 comprises a nanobody comprising an amino acid sequence of SEQ ID NO: 30. In some embodiments, N1 comprises a nanobody comprising an amino acid sequence of SEQ ID NO: 32. In some embodiments, N1 comprises a nanobody comprising an amino acid sequence of SEQ ID NO: 33.

In some embodiments, R4 comprises a nanobody comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 30, 32, or 33. In some embodiments, R4 comprises a nanobody comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 30. In some embodiments, R4 comprises a nanobody comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 32. In some embodiments, R4 comprises a nanobody comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to SEQ ID NO: 33.

In some embodiments, R4 comprises a nanobody comprising an amino acid sequence of SEQ ID NO: 30, 32, or 33. In some embodiments, R4 comprises a nanobody comprising an amino acid sequence of SEQ ID NO: 30. In some embodiments, R4 comprises a nanobody comprising an amino acid sequence of SEQ ID NO: 32. In some embodiments, R4 comprises a nanobody comprising an amino acid sequence of SEQ ID NO: 33.

In some embodiments, a polypeptide having the formula from N-terminus to C-terminus:

N1-P1-variant Fc-R2-R4, further comprises a histidine tag (His-tag), wherein the His-tag is covalently or non-covalently conjugated to the C-terminus of the polypeptide. In some embodiments, the His-tag is such as those provided herein.

In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 56, provided that the variant Fc polypeptide comprises a set of mutations selected from: L234A, L235A, G237A, Y296Q, and P329K; L234A, L235A, G237A, Y296Q, S298K, and P329K; L234A, L235A, G237A, D265K, E269S, Y296Q, and P329K; or L234A, L235A, G237A, D265K, E269S, Y296Q, S298K, and P329K, as compared to SEQ ID NO: 1; and a protease. In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 56, provided that the variant Fc polypeptide comprises a set of mutations of L234A, L235A, G237A, Y296Q, and P329K, as compared to SEQ ID NO: 1; and a protease. In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 56, provided that the variant Fc polypeptide comprises a set of mutations of L234A, L235A, G237A, Y296Q, S298K, and P329K, as compared to SEQ ID NO: 1; and a protease. In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 56, provided that the variant Fc polypeptide comprises a set of mutations of L234A, L235A, G237A, D265K, E269S, Y296Q, and P329K, as compared to SEQ ID NO: 1; and a protease. In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 56, provided that the variant Fc polypeptide comprises a set of mutations of L234A, L235A, G237A, D265K, E269S, Y296Q, S298K, and P329K, as compared to SEQ ID NO: 1; and a protease. In some embodiments, the protease is selected from IdeS, IdeSsuis, IdeE, IdeZ, IdeE2, IdeZ2, or IdeC protease, or a variant thereof.

In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to any one of SEQ ID NO: 23, 19, 20, 21, 22, 23, 24, 25, 42, 43, 44, 45, 46, 47, 48, or 49; and a protease. In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23; and a protease. In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19; and a protease. In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20; and a protease. In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21; and a protease. In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22; and a protease. In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24; and a protease. In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25; and a protease. In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 42; and a protease. In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 43; and a protease. In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 44; and a protease. In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 45; and a protease. In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 46; and a protease. In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 47; and a protease. In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 48; and a protease. In some embodiments, a molecule comprises a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 49; and a protease. In some embodiments, the protease is selected from IdeS, IdeSsuis, IdeE, IdeZ, IdeE2, IdeZ2, or IdeC protease, or a variant thereof.

In some embodiments, a molecule comprises a variant Fc polypeptide comprising an amino acid sequence of any one of SEQ ID NO: 23, 19, 20, 21, 22, 23, 24, 25, 42, 43, 44, 45, 46, 47, 48, or 49; and a protease. In some embodiments, a molecule comprises a variant Fc polypeptide comprising an amino acid sequence of SEQ ID NO: 23; and a protease. In some embodiments, a molecule comprises a variant Fc polypeptide comprising an amino acid sequence of SEQ ID NO: 19; and a protease. In some embodiments, a molecule comprises a variant Fc polypeptide comprising an amino acid sequence of SEQ ID NO: 20; and a protease. In some embodiments, a molecule comprises a variant Fc polypeptide comprising an amino acid sequence of SEQ ID NO: 21; and a protease. In some embodiments, a molecule comprises a variant Fc polypeptide comprising an amino acid sequence of SEQ ID NO: 22; and a protease. In some embodiments, a molecule comprises a variant Fc polypeptide comprising an amino acid sequence of SEQ ID NO: 24; and a protease. In some embodiments, a molecule comprises a variant Fc polypeptide comprising an amino acid sequence of SEQ ID NO: 25; and a protease. In some embodiments, a molecule comprises a variant Fc polypeptide comprising an amino acid sequence of SEQ ID NO: 42; and a protease. In some embodiments, a molecule comprises a variant Fc polypeptide comprising an amino acid sequence of SEQ ID NO: 43; and a protease. In some embodiments, a molecule comprises a variant Fc polypeptide comprising an amino acid sequence of SEQ ID NO: 44; and a protease. In some embodiments, a molecule comprises a variant Fc polypeptide comprising an amino acid sequence of SEQ ID NO: 45; and a protease. In some embodiments, a molecule comprises a variant Fc polypeptide comprising an amino acid sequence of SEQ ID NO: 46; and a protease. In some embodiments, a molecule comprises a variant Fc polypeptide comprising an amino acid sequence of SEQ ID NO: 47; and a protease. In some embodiments, a molecule comprises a variant Fc polypeptide comprising an amino acid sequence of SEQ ID NO: 48; and a protease. In some embodiments, a molecule comprises a variant Fc polypeptide comprising an amino acid sequence of SEQ ID NO: 49; and a protease. In some embodiments, the protease is selected from IdeS, IdeSsuis, IdeE, IdeZ, IdeE2, IdeZ2, or IdeC protease, or a variant thereof.

In some embodiments, a polypeptide comprises an amino acid sequence, and N-terminus to C-terminus orientation, as provided in Table 7, Table 8, Table 9, Table 10, and Table 11.

TABLE 7

| ID | N-terminus IdeS | Fc | C-terminus His-tag |
|---|---|---|---|
| VRT-1 | ANQEIRYSEVTPYHVTSVWTKGVTPPAQFT QGEDVFHAPYVANQGWYDITKTFNGKDDLL CGAATAGNMLHWWFDQNKDQIKRYLEEHPE KQKINFNGEQMFDVKEAIDTKNHQLDSKLF EYFKEKAFPYLSTKHLGVFPDHVIDMFING YRLSLINHGPTPVKEGSKDPRGGIFDAVFT RGDQSKLLTSRHDFKEKNLKEISDLIKKEL TEGKALGLSHTYANVRINHVINLWGADEDS NGNLKAIYVTDSDSNASIGMKKYFVGVNSA GKVAISAKEIKEDNIGAQVLGLFTLSTGQD SWNQIN (SEQ ID NO: 26) | DKTHTCPPCPAPEAAGAPSVFL FPPKPKDTLMISRTPEVTCVVV DVSHEDPEVKFNWYVDGVEVHN AKTKPREEQQNSTYRVVSVLTV LHQDWLNGKEYKCKVSNKALKA PIEKTISKAKGQPREPQVYTLP PSRDELTKNQVSLTCLVKGFYP SDIAVEWESNGQPENNYKTTPP VLDSDGSFFLYSKLTVDKSRWQ QGNVFSCSVMHEALHNHYTQKS LSLSPG (SEQ ID NO: 23) | HHHHHHHH (SEQ ID NO: 27) |
| VRT-2 | ANQEIRYSEVTPYHVTSVWTKGVTPPAQFT QGEDVFHAPYVANQGWYDITKTFNGKDDLL CGAATAGNMLHWWFDQNKDQIKRYLEEHPE KQKINFNGEQMFDVKEAIDTKNHQLDSKLF EYFKEKAFPYLSTKHLGVFPDHVIDMFING YRLSLTNHGPTPVKEGSKDPRGGIFDAVFT RGDQSKLLTSRHDFKEKNLKEISDLIKKEL TEGKALGLSHTYANVRINHVINLWGADEDS NGNLKAIYVTDSDSNASIGMKKYFVGVNSA GKVAISAKEIKEDNIGAQVLGLFTLSTGQD SWNQTN (SEQ ID NO: 26) | DKTHTCPPCPAPEAAGAPSVFL FPPKPKDTLMISRTPEVTCVVV DVSHEDPEVKFNWYVDGVEVHN AKTKPREEQQNSTYRVVSVLTV LHQDWLNGKEYKCKVSNKALKA PIEKTISKAKGQPREPQVYTLP PSRDELTKNQVSLWCLVKGFYP SDIAVEWESNGQPENNYKTTPP VLDSDGSFFLYSKLTVDKSRWQ QGNVFSCSVMHEALHNHYTQKS LSLSPG (SEQ ID NO: 24) | HHHHHHHH (SEQ ID NO: 27) |
| VRT-3 | ANQEIRYSEVTPYHVISVWTKNVTPPAQFT QGEDVFHAPYVANQGWYDITKTFNGKDDLL CGAATAGNMLHWWFDQNKDQIKRYLEEHPE KQKINFNGSQMFDVKEAIDTKNHQLDSKLF EYFKEKAFPYLSTKHLGVFPDHVIDMFING YRLSLNNSGPTPVKNGSKDPRGGIFDAVFT RGDQSKLLTSRHDFKNKSLKEISDLIKKEL TEGKALGLSHTYANVRINHVINLWGADFDS NGTLKAIYVTDSDSNASIGMKKYFVGVNNA TKVAISAKEIKENNTGAQVLGLFTLSTGQD SWNQTN (SEQ ID NO: 28) | DKTHTCPPCPAPEAAGAPSVFL FPPKPKDTLMISRTPEVTCVVV DVSHEDPEVKFNWYVDGVEVHN AKTKPREEQQNSTYRVVSVLTV LHQDWLNGKEYKCKVSNKALKA PIEKTISKAKGQPREPQVYTLP PSRDELTKNQVSLTCLVKGFYP SDIAVEWESNGQPENNYKTTPP VLDSDGSFFLYSKLTVDKSRWQ QGNVFSCSVMHEALHNHYTQKS LSLSPG (SEQ ID NO: 23) | HHHHHHHH (SEQ ID NO: 27) |
| VRT-4 | ANQEIRYSEVTPYHVTSVWTKGVTPPAQFT QGEDVFHAPYVANQGWYDITKTFNGKDDLL CGAATAGNMLHWWFDQNKDQIKRYLEEHPE KQKINFNGEQMEDVKEAIDTKNHQLDSKLF EYFKEKAFPYLSTKHLGVFPDHVIDMFING YRLSLINHGPTPVKEGSKDPRGGIFDAVFT RGDQSKLLTSRHDFKEKNLKEISDLIKKEL TEGKALGLSHTYANVRINHVINLWGADEDS NGNLKAIYVTDSDSNAQIGMKKYFVGVNSA GKVAISAKEIKEDNIGAQVLGLFTLSTGQD SWNQTN (SEQ ID NO: 29) | DKTHTCPPCPAPEAAGAPSVFL FPPKPKDTLMISRTPEVTCVVV DVSHEDPEVKFNWYVDGVEVHN AKTKPREEQQNSTYRVVSVLTV LHQDWLNGKEYKCKVSNKALKA PIEKTISKAKGQPREPQVYTLP PSRDELTKNQVSLTCLVKGFYP SDIAVEWESNGQPENNYKTTPP VLDSDGSFFLYSKLTVDKSRWQ QGNVFSCSVMHEALHNHYTQKS LSLSPG (SEQ ID NO: 23) | HHHHHHHH (SEQ ID NO: 27) |
| VRT-5 | ANQEIRYSEVTPYHVTSVWTKGVTPPAQFT QGEDVFHAPYVANQGWYDITKTENGKDDLL CGAATAGNMLHWWFDQNKDQIKRYLEEHPE KQKINFNGEQMFDVKEAIDTKNHQLDSKLF EYFKEKAFPYLSTKHLGVFPDHVIDMFING YRLSLINHGPTPVKEGSKDPRGGIFDAVFT RGDQSKLLTSRHDFKEKNLKEISDLIKKEL TEGKALGLSHTYANVRINHVINLWGADEDS NGNLKAIYVTDSDSNASIGMKKYFVGVNSA GKVAISAKEIKEDNIGAQVLGLFTLSTGQD SWNQTN (SEQ ID NO: 26) | DKTHTCPPCPAPEAAGAPSVFL FPPKPKDTLMISRTPEVTCVVV DVSHEDPEVKFNWYVDGVEVHN AKTKPREEQQNSTYRVVSVLTV LHQDWLNGKEYKCKVSNKALKA PIEKTISKAKGQPREPQVYTLP PSRDELTKNQVSLTCLVKGFYP SDIAVEWESNGQPENNYKTTPP VLDSDGSFFLYSKLTVDKSRWQ QGNVFSCSVMHEALHNHYTQKS LSLSPG (SEQ ID NO: 23) | (N/A) |
| VRT-6 | ANQEIRYSEVTPYHVTSVWTKGVTPPAQFT QGEDVFHAPYVANQGWYDITKTFNGKDDLL CGAATAGNMLHWWFDQNKDQIKRYLEEHPE KQKINFNGEQMEDVKEAIDTKNHQLDSKLF EYFKEKAFPYLSTKHLGVFPDHVIDMFING YRLSLTNHGPTPVKEGSKDPRGGIFDAVFT RGDQSKLLTSRHDFKEKNLKEISDLIKKEL TEGKALGLSHTYANVRINHVINLWGADEDS | DKTHTCPPCPAPEAAGAPSVFL FPPKPKDTLMISRTPEVTCVVV DVSHEDPEVKFNWYVDGVEVHN AKTKPREEQQNSTYRVVSVLTV LHQDWLNGKEYKCKVSNKALKA PIEKTISKAKGQPREPQVYTLP PSRDELTKNQVSLWCLVKGFYP SDIAVEWESNGQPENNYKTTPP | (N/A) |

TABLE 7-continued

| ID | N-terminus IdeS | Fc | C-terminus His-tag |
|---|---|---|---|
| | NGNLKAIYVTDSDSNASIGMKKYFVGVNSA GKVAISAKEIKEDNIGAQVLGLFTLSTGQD SWNQTN (SEQ ID NO: 26) | VLDSDGSFFLYSKLTVDKSRWQ QGNVFSCSVMHEALHNHYTQKS LSLSPG (SEQ ID NO: 24) | |
| VRT-7 | ANQEIRYSEVTPYHVTSVWTKGVTPPAQFT QGEDVFHAPYVANQGWYDITKTFNGKDDLL CGAATAGNMLHWWFDQNKDQIKRYLEEHPE KQKINFNGEQMFDVKEAIDTKNHQLDSKLF EYFKEKAFPYLSTKHLGVFPDHVIDMFING YRLSLINHGPTPVKEGSKDPRGGIFDAVFT RGDQSKLLTSRHDFKEKNLKEISDLIKKEL TEGKALGLSHTYANVRINHVINLWGADEDS NGNLKAIYVTDSDSNAQIGMKKYFVGVNSA GKVAISAKEIKEDNIGAQVLGLFTLSTGQD SWNQTN (SEQ ID NO: 29) | DKTHTCPPCPAPEAAGAPSVFL FPPKPKDTLMISRTPEVTCVVV DVSHEDPEVKFNWYVDGVEVHN AKTKPREEQQNSTYRVVSVLTV LHQDWLNGKEYKCKVSNKALKA PIEKTISKAKGQPREPQVYTLP PSRDELTKNQVSLTCLVKGFYP SDIAVEWESNGQPENNYKTTPP VLDSDGSFFLYSKLTVDKSRWQ QGNVFSCSVMHEALHNHYTQKS LSLSPG (SEQ ID NO: 23) | (N/A) |
| VRT-8 | ANQEIRYSEVTPYHVTSVWTKGVTPPANFT QGEDVFHAPYVANQGWYDITKTENGKDDLL CGAATAGNMLHWWFDQNKDQIKRYLEEHPE KQKINFNGEQMFDVKEAIDTKNHQLDSKLF EYFKEKAFPYLSTKHLGVFPDHVIDMFING YRLSLTNHGPTPVKEGSKDPRGGIFDAVFT RGDQSKLLTSRHDFKEKNLKEISDLIKKEL TEGKALGLSHTYANVRINHVINLWGADFDS NGNLKAIYVTDSDSNASIGMKKYFVGVNSA GKVAISAKEIKEDNIGAQVLGLFTLSTGQD SWNQTN | DKTHTSPPCPAPEAAGAPSVFL FPPKPKDTLMISRTPEVTCVVV DVSHEDPEVKFNWYVDGVEVHN AKTKPREEQQNSTYRVVSVLTV LHQDWLNGKEYKCKVSNKALKA PIEKTISKAKGQPREPQVYTLP PSRDELTKNQVSLTCLVKGFYP SDIAVEWESNGQPENNYKTTPP VLDSDGSFFLYSKLTVDKSRWQ QGNVFSCSVMHEALHNHYTQKS LSLSPGK | (N/A) |
| VRT-9 | ANQEIRYSEVTPYHVTSVWTKGVTPPANFT QGEDVFHAPYVANQGWYDITKTFNGKDDLL CGAATAGNMLHWWFDQNKDQIKRYLEEHPE KQKINFNGEQMFDVKEAIDTKNHQLDSKLF EYFKEKAFPYLSTKHLGVFPDHVIDMFING YRLSLINHGPTPVKEGSKDPRGGIFDAVFT RGDQSKLLTSRHDFKEKNLKEISDLIKKEL TEGKALGLSHTYANVRINHVINLWGADEDS NGNLKAIYVTDSDSNASIGMKKYFVGVNSA GKVAISAKEIKEDNIGAQVLGLFTLSTGQD SWNQTN | DKTHTSPPSPAPEAAGAPSVFL FPPKPKDTLMISRTPEVTCVVV DVSHEDPEVKFNWYVDGVEVHN AKTKPREEQQNSTYRVVSVLTV LHQDWLNGKEYKCKVSNKALKA PIEKTISKAKGQPREPQVYTLP PSRDELTKNQVSLTCLVKGFYP SDIAVEWESNGQPENNYKTTPP VLDSDGSFFLYSKLTVDKSRWQ QGNVFSCSVMHEALHNHYTQKS LSLSPGK | (N/A) |
| VRT-10 | ANQEIRYSEVTPYHVTSVWTKGVTPPANFT QGEDVFHAPYVANQGWYDITKTFNGKDDLL CGAATAGNMLHWWFDQNKDQIKRYLEEHPE KQKINFNGEQMFDVKEAIDTKNHQLDSKLF EYFKEKAFPYLSTKHLGVFPDHVIDMFING YRLSLINHGPTPVKEGSKDPRGGIFDAVFT RGDQSKLLTSRHDFKEKNLKEISDLIKKEL TEGKALGLSHTYANVRINHVINLWGADFDS NGNLKAIYVTDSDSNASIGMKKYFVGVNSA GKVAISAKEIKEDNIGAQVLGLFTLSTGQD SWNQTN | DKTHTCPPCPAPELLGDSGVFL FPPKPKDTLMISRTPEVTCVVV DVSHDEPEVKFNWYVDGVEVHN AKTKPREEQYNSTYRVVSVLTV LHQDWLNGKEYKCKVSNKALPR PIEKTISKAKGQPREPQVYTLP PSRDELTKNQVSLWCLVKGFYP SDIAVEWESNGQPENNYKTTPP VLDSDGSFFLYSKLTVDKSRWQ QGNVFSCSVMHEALHNHYTQKS LSLSPGK | (N/A) |
| VRT-11 | ANQEIRYSEVTPYHVTSVWTKGVTPPANFT QGEDVFHAPYVANQGWYDITKTFNGKDDLL CGAATAGNMLHWWFDQNKDQIKRYLEEHPE KQKINFNGEQMFDVKEAIDTKNHQLDSKLF EYFKEKAFPYLSTKHLGVFPDHVIDMFING YRLSLTNHGPTPVKEGSKDPRGGIFDAVFT RGDQSKLLTSRHDFKEKNLKEISDLIKKEL TEGKALGLSHTYANVRINHVINLWGADEDS NGNLKAIYVTDSDSNASIGMKKYFVGVNSA GKVAISAKEIKEDNIGAQVLGLFTLSTGQD SWNQTN | DKTHTCPPCPAPEFEGGPSVFL FPPKPKDTLMISRTPEVTCVVV DVSDEDGEVKFNWYVDGVEVHN AKTKPREEQYNSTYRVVSVLTV LHQDWLNGKEYKCKVSNKALAA PIEKTISKAKGQPREPQVYTLP PSRDELTKNQVSLSCAVKGFYP SDIAVEWESNGQPENNYKTTPP VLDSDGSFFLVSKLTVDKSRWQ QGNVFSCSVMHEALHNHYTQKS LSLSPGK | (N/A) |
| VRT-12 | ANQEIRYSEVTPYHVTSVWTKGVTPPANFT QGEDVFHAPYVANQGWYDITKTFNGKDDLL CGAATAGNMLHWWFDQNKDQIKRYLEEHPE KQKINFNGEQMFDVKEAIDTKNHQLDSKLF EYFKEKAFPYLSTKHLGVFPDHVIDMFING YRLSLTNHGPTPVKEGSKDPRGGIFDAVFT RGDQSKLLTSRHDFKEKNLKEISDLIKKEL TEGKALGLSHTYANVRINHVINLWGADEDS NGNLKAIYVTDSDSNASIGMKKYFVGVNSA GKVAISAKEIKEDNIGAQVLGLFTLSTGQD SWNQTN | DKTHTCPPCPAPEFEGGPSVFL FPPKPKDTLMISRTPEVTCVVV DVSQEDPEVQFNWYVDGVEVHN AKTKPREEQFNSTYRVVSVLTV LHQDWLNGKEYKCKVSNKALPS SIEKTISKAKGQPREPQVYTLP PSRDELTKNQVSLWCLVKGFYP SDIAVEWESNGQPENNYKTTPP VLDSDGSFFLYSKLTVDKSRWQ QGNVFSCSVMHEALHNHYTQKS LSLSPGK | (N/A) |

TABLE 7-continued

| ID | N-terminus IdeS | Fc | C-terminus His-tag |
|---|---|---|---|
| VRT-13 | ANQEIRYSEVTPYHVISVWTKGVTPPANFTQGEDVFHAPYVANQGWYDITKTFNGKDDLLCGAATAGNMLHWWFDQNKDQIKRYLEEHPEKQKINFNGEQMFDVKEAIDTKNHQLDSKLFEYFKEKAFPYLSTKHLGVFPDHVIDMFINGYRLSLTNHGPTPVKEGSKDPRGGIFDAVFTRGDQSKLLTSRHDFKEKNLKEISDLIKKELTEGKALGLSHTYANVRINHVINLWGADEDSNGNLKAIYVTDSDSNASIGMKKYFVGVNSAGKVAISAKEIKEDNIGAQVLGLFTLSTGQDSWNQTN | DKTHTCPPCPAPEFEGGPSVFLFPPKPKDTLMISRTPEVTCVVVDVSDEDGEVQFNWYVDGVEVHNAKTKPREEQFNSTYRVVSVLTVLHQDWLNGKEYKCKVSNKALASSIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | (N/A) |
| VRT-14 | RNATEAYAKEVPHQITSVWTKGVTPLTPEQFRYNNEDVIHAPYLAHQGWYDITKAFDGKDNLLCGAATAGNMLHWWFDQNKTEIEAYLSKHPEKQKIIFNNQELFDLKAAIDTKDSQTNSQLFNYFRDKAFPNLSARQLGVMPDLVLDMFINGYYLNVFKTQSTDVNRPYQDKDKRGGIFDAVFTRGDQTTLLTARHDLKNKGLNDISTIIKQELTEGRALALSHTYANVSISHVINLWGADFNAEGNLEAIYVTDSDANASIGMKKYFVGINAHGHVAISAKKIEGENIGAQVLGLFTLSSGKDIWQKLS | DKTHTSPPCPAPEAAGAPSVFLFPPKPKDTLMISRTPEVTCVVVDVSHEDPEVKFNWYVDGVEVHNAKTKPREEQQNSTYRVVSVLTVLHQDWLNGKEYKCKVSNKALKAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | (N/A) |
| VRT-15 | ANQEIRYSNVTPYHVTSVWTKGVTPPANFTQGEDVFHAPYVANQGWYDITKTFNGKDDLLCGAATAGNMLHWWFDQNKDQIKRYLEEHPEKQKINFNGEQMFDVKEAIDTKNHQLDSKLFEYFKEKAFPYLSTKHLGVFPDHVIDMFINGYRLSLTNHGPTPVKEGSKDPRGGIFDAVFTRGDQSKLLTSRHDFKEKNLKEISDLIKKELTEGKALGLSHTYANVRINHVINLWGADFDSNGNLKAIYVTDSDSNASIGMKKYFVGVNSAGKVAISAKEIKEDNIGAQVLGLFTLSTGQDSWNQTN | DKTHTCPPCPAPEAAGAPSVFLFPPKPKDTLMISRTPEVTCVVVDVSHEDPEVKFNWYVDGVEVHNAKTKPREEQQNSTYRVVSVLTVLHQDWLNGKEYKCKVSNKALKAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | (N/A) |
| VRT-16 | ANQEIRYSEVTPYHNTSVWTKGVTPPANFTQGEDVFHAPYVANQGWYDITKTENGKDDLLCGAATAGNMLHWWFDQNKDQIKRYLEEHPEKQKINFNGEQMFDVKEAIDTKNHQLDSKLFEYFKEKAFPYLSTKHLGVFPDHVIDMFINGYRLSLTNHGPTPVKEGSKDPRGGIFDAVFTRGDQSKLLTSRHDFKEKNLKEISDLIKKELTEGKALGLSHTYANVRINHVINLWGADEDSNGSLKAIYVTDSDSNASIGMKKYFVGVNSAGKVAISAKEIKEDNIGAQVLGLFTLSTGQDSWNQTN | DKTHTCPPCPAPEAAGAPSVFLFPPKPKDTLMISRTPEVTCVVVDVSHEDPEVKFNWYVDGVEVHNAKTKPREEQQNSTYRVVSVLTVLHQDWLNGKEYKCKVSNKALKAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | (N/A) |
| VRT-17 | ANQEIRYSEVTPYHVISVWTKGVTPPANFTQGEDVFHAPYVANQGWYDITKTFNGKDDLLCGAATAGNMLHWWFDQNKDQIKRYLEEHPEKQKINFNGEQMFDVKEAIDTKNHQLDSKLFEYFKEKAFPYLSTKHLGVFPDHVIDMFINGYRLSLTNHGPTPVKEGSKDPRGGIFDAVFTRGDQSKLLTSRHDFKEKNLKEISDLIKKELTEGKALGLSHTYANVRINHVINLWGADFDSNGNLKAIYVTDSDSNASIGMKKYFVGVNSAGKVAISAKEIKEDNIGAQVLGLFTLSTGQDSWNQTN | DKTHTSPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | (N/A) |
| VRT-18 | ANQEIRYSEVTPYHVISVWTKGVTPPANFTQGEDVFHAPYVANQGWYDITKTFNGKDDLLCGAATAGNMLHWWFDQNKDQIKRYLEEHPEKQKINFNGEQMFDVKEAIDTKNHQLDSKLFEYFKEKAFPYLSTKHLGVFPDHVIDMFINGYRLSLTNHGPTPVKEGSKDPRGGIFDAVFTRGDQSKLLTSRHDFKEKNLKEISDLIKKELTEGKALGLSHTYANVRINHVINLWGADFDSNGNLKAIYVTDSDSNASIGMKKYFVGVNSAGKVAISAKEIKEDNIGAQVLGLFTLSTGQDLSLSPGK | DKTHTSPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSSWNQTN | (N/A) |

TABLE 8

| ID | Fc | C-terminus IdeS | C-terminus His-tag |
|---|---|---|---|
| VRT-19 | DKTHTCPPCPAPEAAGAPSVFLFPPKPKDTLMISRTPEVTCVVVDVSHEDPEVKFNWYVDGVEVHNAKTKPREEQQNSTYRVVSVLTVLHQDWLNGKEYKCKVSNKALKAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 23) | ANQEIRYSEVTPYHVISVWTKGVTPPAQFTQGEDVFHAPYVANQGWYDITKTFNGKDDLLCGAATAGNMLHWWFDQNKDQIKRYLEEHPEKQKINFNGEQMEDVKEAIDTKNHQLDSKLFEYFKEKAFPYLSTKHLGVFPDHVIDMFINGYRLSLINHGPTPVKEGSKDPRGGIFDAVFTRGDQSKLLTSRHDFKEKNLKEISDLIKKELTEGKALGLSHTYANVRINHVINLWGADFDSNGNLKAIYVTDSDSNASIGMKKYFVGVNSAGKVAISAKEIKEDNIGAQVLGLFTLSTGQDSWNQTN (SEQ ID NO: 26) | HHHHHHHH (SEQ ID NO: 27) |
| VRT-20 | DKTHTCPPCPAPEAAGAPSVFLFPPKPKDTLMISRTPEVTCVVVDVSHEDPEVKFNWYVDGVEVHNAKTKPREEQQNSTYRVVSVLTVLHQDWLNGKEYKCKVSNKALKAPIEKTISKAKGQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPG (SEQ ID NO: 24) | ANQEIRYSEVTPYHVTSVWTKGVTPPAQFTQGEDVFHAPYVANQGWYDITKTFNGKDDLLCGAATAGNMLHWWFDQNKDQIKRYLEEHPEKQKINFNGEQMFDVKEAIDTKNHQLDSKLFEYFKEKAFPYLSTKHLGVFPDHVIDMFINGYRLSLINHGPTPVKEGSKDPRGGIFDAVFTRGDQSKLLTSRHDFKEKNLKEISDLIKKELTEGKALGLSHTYANVRINHVINLWGADFDSNGNLKAIYVTDSDSNASIGMKKYFVGVNSAGKVAISAKEIKEDNIGAQVLGLFTLSTGQDSWNQTN (SEQ ID NO: 26) | HHHHHHHH (SEQ ID NO: 27) |
| VRT-21 | DKTHTCPPCPAPEAAGAPSVFLFPPKPKDTLMISRTPEVTCVVVDVSHEDPEVKFNWYVDGVEVHNAKTKPREEQQNSTYRVVSVLTVLHQDWLNGKEYKCKVSNKALKAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 23) | ANQEIRYSEVTPYHVTSVWTKGVTPPAQFTQGEDVFHAPYVANQGWYDITKTFNGKDDLLCGAATAGNMLHWWFDQNKDQIKRYLEEHPEKQKINFNGEQMFDVKEAIDTKNHQLDSKLFEYFKEKAFPYLSTKHLGVFPDHVIDMFINGYRLSLTNHGPTPVKEGSKDPRGGIFDAVFTRGDQSKLLTSRHDFKEKNLKEISDLIKKELTEGKALGLSHTYANVRINHVINLWGADFDSNGNLKAIYVTDSDSNAQIGMKKYFVGVNSAGKVAISAKEIKEDNIGAQVLGLFTLSTGQDSWNQTN (SEQ ID NO: 29) | HHHHHHHH (SEQ ID NO: 27) |
| VRT-22 | DKTHTCPPCPAPEAAGAPSVFLFPPKPKDTLMISRTPEVTCVVVDVSHEDPEVKFNWYVDGVEVHNAKTKPREEQQNSTYRVVSVLTVLHQDWLNGKEYKCKVSNKALKAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 23) | ANQEIRYSEVTPYHVTSVWTKGVTPPAQFTQGEDVFHAPYVANQGWYDITKTFNGKDDLLCGAATAGNMLHWWFDQNKDQIKRYLEEHPEKQKINFNGEQMEDVKEAIDTKNHQLDSKLFEYFKEKAFPYLSTKHLGVFPDHVIDMFINGYRLSLINHGPTPVKEGSKDPRGGIFDAVFTRGDQSKLLTSRHDFKEKNLKEISDLIKKELTEGKALGLSHTYANVRINHVINLWGADFDSNGNLKAIYVTDSDSNASIGMKKYFVGVNSAGKVAISAKEIKEDNIGAQVLGLFTLSTGQDSWNQTN (SEQ ID NO: 26) | (N/A) |
| VRI-23 | DKTHTCPPCPAPEAAGAPSVFLFPPKPKDTLMISRTPEVTCVVVDVSHEDPEVKFNWYVDGVEVHNAKTKPREEQQNSTYRVVSVLTVLHQDWLNGKEYKCKVSNKALKAPIEKTISKAKGQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPG (SEQ ID NO: 24) | ANQEIRYSEVTPYHVTSVWTKGVTPPAQFTQGEDVFHAPYVANQGWYDITKTFNGKDDLLCGAATAGNMLHWWFDQNKDQIKRYLEEHPEKQKINFNGEQMEDVKEAIDTKNHQLDSKLFEYFKEKAFPYLSTKHLGVFPDHVIDMFINGYRLSLINHGPTPVKEGSKDPRGGIFDAVFTRGDQSKLLTSRHDFKEKNLKEISDLIKKELTEGKALGLSHTYANVRINHVINLWGADFDSNGNLKAIYVTDSDSNASIGMKKYFVGVNSAGKVAISAKEIKEDNIGAQVLGLFTLSTGQDSWNQTN (SEQ ID NO: 26) | (N/A) |
| VRT-24 | DKTHTCPPCPAPEAAGAPSVFLFPPKPKDTLMISRTPEVTCVVVDVSHEDPEVKFNWYVDGVEVHNAKTKPREEQQNSTYRVVSVLTVLHQDWLNGKEYKCKVSNKALKAPIEKTISKAKGQPREPQVYTLPPSRDELTKNQVSLTCLVKGFYPSDIAVEWESNGQPENNYKTTPPVLDSDGSFFLYSKLTVDKSRWQ | ANQEIRYSEVTPYHVTSVWTKGVTPPAQFTQGEDVFHAPYVANQGWYDITKTENGKDDLLCGAATAGNMLHWWFDQNKDQIKRYLEEHPEKQKINFNGEQMFDVKEAIDTKNHQLDSKLFEYFKEKAFPYLSTKHLGVFPDHVIDMFINGYRLSLINHGPTPVKEGSKDPRGGIFDAVFTRGDQSKLLTSRHDFKEKNLKEISDLIKKELTEGKALGLSHTYANVRINHVINLWGADFDSNGNLKAIYVTDSDSNAQIGMKKYFVGVNSA | (N/A) |

TABLE 8-continued

| ID | Fc | C-terminus IdeS | C-terminus His-tag |
|---|---|---|---|
| | QGNVFSCSVMHEALHNHYTQKSLSLSPG (SEQ ID NO: 23) | GKVAISAKEIKEDNIGAQVLGLFTLSTGQDSWNQTN (SEQ ID NO: 29) | |

TABLE 9

| ID | C-terminus IdeS | Fc | C-terminus IdeS | C-terminus His-tag |
|---|---|---|---|---|
| VRT-25 | ANQEIRYSEVTPYHVTSVWTKGVTPPAQFTQGEDVFHAPYVANQGWYDITKTFNGKDDLLCGAATAGNMLHWWFDQNKDQIKRYLEEHPEKQKINFNGEQMFDVKEAIDTKNHQLDSKLFEYFKEKAFPYLSTKHLGVFPDHVIDMFINGYRLSLTNHGPTPVKEGSKDPRGGIFDAVFTRGDQSKLLTSRHDFKEKNLKEISDLIKKELTEGKALGLSHTYANVRINHVINLWGADFDSNGNLKAIYVTDSDSNASIGMKKYFVGVNSAGKVAISAKEIKEDNIGAQVLGLFTLSTGQDSWNQTN (SEQ ID NO: 26) | DKTHTCPPCPAPEAAGAPSVFLFPPKPKDTLMISRTPEVTCVVVDVSHEDPEVKFNWYVDGVEVHNAKTKPREEQQNSTYRVVSVLTVLHQDWLNGKEYKCKVSNKALKAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 23) | ANQEIRYSEVTPYHVTSVWTKGVTPPAQFTQGEDVFHAPYVANQGWYDITKTFNGKDDLLCGAATAGNMLHWWFDQNKDQIKRYLEEHPEKQKINFNGEQMEDVKEAIDTKNHQLDSKLFEYFKEKAFPYLSTKHLGVFPDHVIDMFINGYRLSLTNHGPTPVKEGSKDPRGGIFDAVFTRGDQSKLLTSRHDFKEKNLKEISDLIKKELTEGKALGLSHTYANVRINHVINLWGADFDSNGNLKAIYVIDSDSNASIGMKKYFVGVNSAGKVAISAKEIKEDNIGAQVLGLFTLSTGQDSWNQTN (SEQ ID NO: 26) | HHHHHHHH (SEQ ID NO: 27) |
| VRT-26 | ANQEIRYSEVTPYHVTSVWTKGVTPPAQFTQGEDVFHAPYVANQGWYDITKTFNGKDDLLCGAATAGNMLHWWFDQNKDQIKRYLEEHPEKQKINFNGEQMEDVKEAIDTKNHQLDSKLFEYFKEKAFPYLSTKHLGVFPDHVIDMFINGYRLSLINHGPTPVKEGSKDPRGGIFDAVFTRGDQSKLLTSRHDFKEKNLKEISDLIKKELTEGKALGLSHTYANVRINHVINLWGADFDSNGNLKAIYVTDSDSNASIGMKKYFVGVNSAGKVAISAKEIKEDNIGAQVLGLFTLSTGQDSWNQTN (SEQ ID NO: 26) | DKTHTCPPCPAPEAAGAPSVFLFPPKPKDTLMISRTPEVTCVVVDVSHEDPEVKFNWYVDGVEVHNAKTKPREEQQNSTYRVVSVLTVLHQDWLNGKEYKCKVSNKALKAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 23) | ANQEIRYSEVTPYHVTSVWTKGVTPPAQFTQGEDVFHAPYVANQGWYDITKTFNGKDDLLCGAATAGNMLHWWFDQNKDQIKRYLEEHPEKQKINENGEQMFDVKEAIDTKNHQLDSKLFEYFKEKAFPYLSTKHLGVFPDHVIDMFINGYRLSLINHGPTPVKEGSKDPRGGIFDAVFTRGDQSKLLTSRHDFKEKNLKEISDLIKKELTEGKALGLSHTYANVRINHVINLWGADFDSNGNLKAIYVTDSDSNASIGMKKYFVGVNSAGKVAISAKEIKEDNIGAQVLGLFTLSTGQDSWNQTN (SEQ ID NO: 26) | (N/A) |

TABLE 10

| ID | N-terminus VHH | N-terminus IdeS | Fc | C-terminus His-tag |
|---|---|---|---|---|
| VRT-27 | QVQLQESGGGLVQAGGSLRLSCAASGYISDAYYMGWYRQAPGKEREFVATITHGTNTYYADSVKGRFTISRDNAKNTVYLQMNSLKPEDTAVYYCAVLETRSYSFRYWGQGTQVTVSSLEGGGGS (SEQ ID NO: 30) | ANQEIRYSEVTPYHVTSVWTKGVTPPAQFTQGEDVFHAPYVANQGWYDITKTFNGKDDLLCGAATAGNMLHWWFDQNKDQIKRYLEEHPEKQKINFNGEQMEDVKEAIDTKNHQLDSKLFEYFKEKAFPYLSTKHLGVFPDHVIDMFINGYRLSLTNHGPTPVKEGSKDPRGGIFDAVFTRGDQSKLLTSRHDFKEKNLKEISDLIKKELTEGKALGLSHTYANVRINHVINLWGADFDSNGNLKAIYVTDSDSNAQIGMKKYFVGVNSAGKVAISAKEIKEDNIGAQVLGLFTLSTGQDSWNQTN (SEQ ID NO: 29) | DKTHTCPPCPAPEAAGAPSVFLFPPKPKDTLMISRTPEVTCVVVDVSHEDPEVKFNWYVDGVEVHNAKTKPREEQQNSTYRVVSVLTVLHQDWLNGKEYKCKVSNKALKAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 23) | HHHHHHHH (SEQ ID NO: 27) |

TABLE 10-continued

| ID | N-terminus VHH | N-terminus IdeS | Fc | C-terminus His-tag |
|---|---|---|---|---|
| VRT-28 | QVQLQESGGG LVQAGGSLRL SCAASGYISD AYYMGWYRQA PGKEREFVAT ITHGTNTYYA DSVKGRFTIS RDNAKNTVYL QMNSLKPEDT AVYYCAVLET RSYSFRYWGQ GTQVTVSSLE GGGGS (SEQ ID NO: 30) | ANQEIRYSEVTPYHVISVWTKGV TPPAQFTQGEDVFHAPYVANQGW YDITKTFNGKDDLLCGAATAGNM LHWWFDQNKDQIKRYLEEHPEKQ KINFNGEQMFDVKEAIDTKNHQL DSKLFEYFKEKAFPYLSTKHLGV FPDHVIDMFINGYRLSLINHGPT PVKEGSKDPRGGIFDAVFTRGDQ SKLLTSRHDFKEKNLKEISDLIK KELTEGKALGLSHTYANVRINHV INLWGADFDSNGNLKAIYVTDSD SNAQIGMKKYFVGVNSAGKVAIS AKEIKEDNIGAQVLGLFTLSTGQ DSWNQTN (SEQ ID NO: 29) | DKTHTCPPCPAPEAAGA PSVFLFPPKPKDTLMIS RTPEVTCVVVDVSHEDP EVKFNWYVDGVEVHNAK TKPREEQQNSTYRVVSV LTVLHQDWLNGKEYKCK VSNKALKAPIEKTISKA KGQPREPQVYTLPPSRD ELTKNQVSLTCLVKGFY PSDIAVEWESNGQPENN YKTTPPVLDSDGSFFLY SKLTVDKSRWQQGNVFS CSVMHEALHNHYTQKSL SLSPG (SEQ ID NO: 23) | (N/A) |

TABLE 11

| ID | Fc | C-terminus IdeS | N-terminus VHH | C-terminus His-tag |
|---|---|---|---|---|
| VRT-29 | DKTHTCPPCPAPEAAGA PSVFLFPPKPKDTLMIS RTPEVTCVVVDVSHEDP EVKFNWYVDGVEVHNAK TKPREEQQNSTYRVVSV LTVLHQDWLNGKEYKCK VSNKALKAPIEKTISKA KGQPREPQVYTLPPSRD ELTKNQVSLTCLVKGFY PSDIAVEWESNGQPENN YKTTPPVLDSDGSFFLY SKLTVDKSRWQQGNVFS CSVMHEALHNHYTQKSL SLSPG (SEQ ID NO: 23) | ANQEIRYSEVTPYHVTSVWTKGV TPPAQFTQGEDVFHAPYVANQGW YDITKTFNGKDDLLCGAATAGNM LHWWFDQNKDQIKRYLEEHPEKQ KINFNGEQMFDVKEAIDTKNHQL DSKLFEYFKEKAFPYLSTKHLGV FPDHVIDMFINGYRLSLINHGPT PVKEGSKDPRGGIFDAVFTRGDQ SKLLTSRHDFKEKNLKEISDLIK KELTEGKALGLSHTYANVRINHV INLWGADFDSNGNLKAIYVTDSD SNAQIGMKKYFVGVNSAGKVAIS AKEIKEDNIGAQVLGLFTLSTGQ DSWNQTNGGGGS (SEQ ID NO: 31) | QVQLQESGGG LVQAGGSLRL SCAASGYISD AYYMGWYRQA PGKEREFVAT ITHGTNTYYA DSVKGRFTIS RDNAKNTVYL QMNSLKPEDT AVYYCAVLET RSYSFRYWGQ GTQVTVSSLE GG (SEQ ID NO: 32) | HHHHHHHH (SEQ ID NO: 27) |
| VRT-30 | DKTHTCPPCPAPEAAGA PSVFLFPPKPKDTLMIS RTPEVTCVVVDVSHEDP EVKFNWYVDGVEVHNAK TKPREEQQNSTYRVVSV LTVLHQDWLNGKEYKCK VSNKALKAPIEKTISKA KGQPREPQVYTLPPSRD ELTKNQVSLTCLVKGFY PSDIAVEWESNGQPENN YKTTPPVLDSDGSFFLY SKLTVDKSRWQQGNVFS CSVMHEALHNHYTQKSL SLSPG (SEQ ID NO: 23) | ANQEIRYSEVTPYHVISVWTKGV TPPAQFTQGEDVFHAPYVANQGW YDITKTFNGKDDLLCGAATAGNM LHWWFDQNKDQIKRYLEEHPEKQ KINFNGEQMFDVKEAIDTKNHQL DSKLFEYFKEKAFPYLSTKHLGV FPDHVIDMFINGYRLSLTNHGPT PVKEGSKDPRGGIFDAVETRGDQ SKLLTSRHDFKEKNLKEISDLIK KELTEGKALGLSHTYANVRINHV INLWGADFDSNGNLKAIYVTDSD SNAQIGMKKYFVGVNSAGKVAIS AKEIKEDNIGAQVLGLFTLSTGQ DSWNQTNGGGGS (SEQ ID NO: 31) | QVQLQESGGG LVQAGGSLRL SCAASGYISD AYYMGWYRQA PGKEREFVAT ITHGTNTYYA DSVKGRFTIS RDNAKNTVYL QMNSLKPEDT AVYYCAVLET RSYSFRYWGQ GTQVTVSSLE (SEQ ID NO: 33) | (N/A) |

In some embodiments, the polypeptides do not comprise the histidine illustrated in the table above.

In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity, or is identical, to any one sequence of VRT-1, VRT-2, VRT-3, VRT-4, VRT-5, VRT-6, VRT-7, VRT-8, VRT-9, VRT-10, VRT-11, VRT-12, VRT-13, VRT-14, VRT-15, VRT-16, VRT-17, VRT-18, VRT-19, VRT-20, VRT-21, VRT-22, VRT-23, VRT-24, VRT-25, VRT-26, VRT-27, VRT-28, VRT-29, or VRT-30.

In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-1. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-2.

In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-3. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-4. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-5. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-6. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-7. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-8. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-9. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-10. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-11. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-12. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-13. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-14. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-15. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-16. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-17. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-18. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-19. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-20. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-21. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-22. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-23. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-24. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-25. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-26. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-27. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the e sequence of VRT-28. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-29. In some embodiments, a polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the amino acid sequence of VRT-30.

In some embodiments, the polypeptide that is less than 100% identical to the reference sequence retains the protease activity and the Fc polypeptide is protease resistant. In some embodiments, the protease resistant Fc polypeptide comprise a Y296Q and/or a P329K mutation. In some embodiments, the protease resistant Fc polypeptide comprises a L234A, L235A, and/or G237A mutation. In some embodiments, the protease resistant Fc polypeptide comprises one, two, or each of L234A, L235A, and/or G237A mutations and one or both of Y296Q and/or a P329K mutations. In some embodiments, the protease resistant Fc polypeptide comprises a set of L234A, L235A, G237A, Y296Q and P329K mutations.

In some embodiments, a polypeptide comprises an amino acid sequence of any one of VRT-1, VRT-2, VRT-3, VRT-4, VRT-5, VRT-6, VRT-7, VRT-8, VRT-9, VRT-10, VRT-11, VRT-12, VRT-13, VRT-14, VRT-15, VRT-16, VRT-17, VRT-18, VRT-19, VRT-20, VRT-21, VRT-22, VRT-23, VRT-24, VRT-25, VRT-26, VRT-27, VRT-28, VRT-29, or VRT-30. In some embodiments, a polypeptide comprises an amino acid sequence of VRT-1. In some embodiments, a polypeptide comprises an amino acid sequence of VRT-2. In some embodiments, a polypeptide comprises an amino acid sequence of VRT-3. In some embodiments, a polypeptide comprises an amino acid sequence of VRT-4. In some embodiments, a polypeptide comprises an amino acid sequence of VRT-5. In some embodiments, a polypeptide comprises an amino acid sequence of VRT-6. In some embodiments, a polypeptide comprises an amino acid sequence of VRT-7. In some embodiments, a polypeptide comprises an amino acid sequence of VRT-8. In some embodiments, a polypeptide comprises an amino acid sequence of VRT-9. In some embodiments, a polypeptide comprises an amino acid sequence of VRT-10. In some embodiments, a polypeptide comprises an amino acid sequence of VRT-11. In some embodiments, a polypeptide comprises an amino acid sequence of VRT-12. In some embodiments, a polypeptide comprises an amino acid sequence of VRT-13. In some embodiments, a polypeptide comprises an amino acid sequence of VRT-14. In some embodiments, a polypeptide comprises an amino acid sequence of VRT-15. In some embodiments, a polypeptide comprises an amino acid sequence of VRT-16. In some embodiments, a polypeptide comprises an amino acid sequence of VRT-17. In some embodiments, a polypeptide comprises an amino acid sequence of VRT-18. In some embodiments, a polypeptide comprises an amino acid sequence of VRT-19. In some embodiments, a polypeptide comprises an amino acid sequence of VRT-20. In some embodiments, a polypeptide comprises an amino acid sequence of VRT-21. In some embodiments, a polypeptide comprises an amino acid sequence of VRT-22. In some embodiments, a polypeptide comprises an amino acid sequence of VRT-23. In some embodiments, a polypeptide comprises an amino acid sequence of VRT-24. In some embodiments, a polypeptide comprises an amino acid sequence of VRT-25. In some embodiments, a polypeptide comprises an amino acid sequence of VRT-26. In some embodiments, a polypeptide comprises an amino acid sequence of VRT-27. In some embodiments, a polypeptide comprises an amino acid sequence of VRT-28. In some embodiments, a polypeptide comprises an amino acid sequence of VRT-29. In some embodiments, a polypeptide comprises an amino acid sequence of VRT-30.

In some embodiments, two (or more) polypeptides associate, either covalently or non-covalently, e.g., to form a hetero or homo-dimeric therapeutic compound. In some embodiments, the linker can comprise an Fc region and two Fc regions associate with one another. In some embodiments of a therapeutic compound comprising two linker regions, the linker regions can self-associate, e.g., as two identical Fc regions. In some embodiments of a therapeutic compound comprising two linker regions, the linker regions are not capable of, or not capable of substantial, self-association, e.g., the two Fc regions can be members of a knob and hole pair.

In some embodiments, a polypeptide can associate with another polypeptide. In some embodiments, the polypeptide associated with another polypeptide forms a dimer molecule. In some embodiments, the polypeptide comprises a first polypeptide and a second polypeptide. In some embodiments, the first polypeptide comprises a knob mutation, and the second polypeptide comprises a hole mutation. In some embodiments, the first polypeptide comprises a hole mutation, and the second polypeptide comprises a knob mutation. In some embodiments, the knob mutation is such as those provided herein. In some embodiments, the hole mutation is such as those provided herein.

In some embodiments, a dimer molecule comprises a first polypeptide and a second polypeptide. In some embodiments, a first polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any one sequence of VRT-1, VRT-2, VRT-3, VRT-4, VRT-5, VRT-6, VRT-7, VRT-8, VRT-9, VRT-10, VRT-11, VRT-12, VRT-13, VRT-14, VRT-15, VRT-16, VRT-17, VRT-18, VRT-19, VRT-20, VRT-21, VRT-22, VRT-23, VRT-24, VRT-25, VRT-26, VRT-27, VRT-28, VRT-29, or VRT-30. In some embodiments, a second polypeptide comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any one sequence of VRT-1, VRT-2, VRT-3, VRT-4, VRT-5, VRT-6, VRT-7, VRT-8, VRT-9, VRT-10, VRT-11, VRT-12, VRT-13, VRT-14, VRT-15, VRT-16, VRT-17, VRT-18, VRT-19, VRT-20, VRT-21, VRT-22, VRT- 23, VRT-24, VRT-25, VRT-26, VRT-27, VRT-28, VRT-29, or VRT-30. In some embodiments, a dimer molecule comprises a first polypeptide comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any one sequence of VRT-1, VRT-2, VRT-3, VRT-4, VRT-5, VRT-6, VRT-7, VRT-8, VRT-9, VRT-10, VRT-11, VRT-12, VRT-13, VRT-14, VRT-15, VRT-16, VRT-17, VRT-18, VRT-19, VRT-20, VRT-21, VRT-22, VRT-23, VRT-24, VRT-25, VRT-26, VRT-27, VRT-28, VRT-29, or VRT-30; and a second polypeptide comprising an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to any one sequence of VRT-1, VRT-2, VRT-3, VRT-4, VRT-5, VRT-6, VRT-7, VRT-8, VRT-9, VRT-10, VRT-11, VRT-12, VRT-13, VRT-14, VRT-15, VRT-16, VRT-17, VRT-18, VRT-19, VRT-20, VRT-21, VRT-22, VRT-23, VRT-24, VRT-25, VRT-26, VRT-27, VRT-28, VRT-29, or VRT-30.

In some embodiments, the dimer is a homodimer molecule. In some embodiments, the dimer is a heterodimer molecule.

As used herein, the term "non-covalently conjugated" can mean that a polypeptide is tethered to another polypeptide through a linker. In some embodiments, the linker is a peptide linker. Non-limiting examples of peptide linkers that can be used are known in the art and are provide for herein.

As discussed herein the different domains, molecules, or polypeptide can be linked together with a linker domain or region. Any linker region described herein can be used as a linker. Linkers can be for example, glycine/serine linkers. In some embodiments, the linker can comprise one or more repeats of GGGGS (SEQ ID NO: 57). In some embodiments, the linker comprises 1, 2, 3, 4, or 5 repeats. In some embodiments, the linker comprises GGGGSGGGGS (SEQ ID NO: 58). In some embodiments, the linker comprises GGGGSGGGGSGGGGS (SEQ ID NO: 59). In some embodiments, the linker comprises: GGGGS (SEQ ID NO: 57), (GGGGS)$_3$ (SEQ ID NO: 59), (GGGGS)$_n$ (n=1, 2, 3, 4) (SEQ ID NO: 57, SEQ ID NO: 58, SEQ ID NO: 59, SEQ ID NO: 60), (Gly); (SEQ ID NO: 61), (Gly)$_6$ (SEQ ID NO: 62), (EAAAK)$_3$ (SEQ ID NO: 63), (EAAK)$_n$ (n=1-3) (SEQ ID NO: 64, SEQ ID NO: 65, SEQ ID NO: 66), A(EAAAK)$_4$ ALEA(EAAAK)4A (SEQ ID NO: 67), or AEAAAKEAAAKA (SEQ ID NO: 68). These linkers can be used in any of the compounds or compositions provided herein.

Antibody molecule, as that term is used herein, refers to a polypeptide, e.g., an immunoglobulin chain or fragment thereof, comprising at least one functional immunoglobulin variable domain sequence. An antibody molecule encompasses antibodies (e.g., full-length antibodies) and antibody fragments. In some embodiments, an antibody molecule comprises an antigen binding or functional fragment of a full length antibody, or a full length immunoglobulin chain. For example, a full-length antibody is an immunoglobulin (Ig) molecule (e.g., an IgG antibody) that is naturally occurring or formed by normal immunoglobulin gene fragment recombinatorial processes). In embodiments, an antibody molecule refers to an immunologically active, antigen-binding portion of an immunoglobulin molecule, such as an antibody fragment. An antibody fragment, e.g., functional fragment, comprises a portion of an antibody, e.g., Fab, Fab', F(ab')2, F(ab)2, variable fragment (Fv), domain antibody (dAb), or single chain variable fragment (scFv). A functional antibody fragment binds to the same antigen as that recognized by the intact (e.g., full-length) antibody. The terms "antibody fragment" or "functional fragment" also include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). In some embodiments, an antibody fragment does not include portions of antibodies without antigen binding activity, such as Fc fragments or single amino acid residues. Exemplary antibody molecules include full length antibodies and antibody fragments, e.g., dAb (domain antibody), single chain, Fab, Fab', and F(ab')2 fragments, and single chain variable fragments (scFvs).

The term "antibody molecule" also encompasses whole or antigen binding fragments of domain, or single domain, antibodies, which can also be referred to as "sdAb" or "VHH." Domain antibodies comprise either $V_H$ or $V_L$ that can act as stand-alone, antibody fragments. Additionally, domain antibodies include heavy-chain-only antibodies (HCAbs). Domain antibodies also include a CH2 domain of an IgG as the base scaffold into which CDR loops are grafted. It can also be generally defined as a polypeptide or protein comprising an amino acid sequence that is comprised of four framework regions interrupted by three complementarity determining regions. This is represented as FP1-CDP1-FR2-CDR2-FN1-CDN1-FR4. sdAbs can be produced in camelids such as llamas, but can also be synthetically generated using techniques that are well known in the art. The numbering of the amino acid residues of a sdAb or polypeptide is according to the general numbering for VH domains given by Kabat et al. ("Sequence of proteins of immunological interest," US Public Health Services, NIH Bethesda, MD, Publication No. 91, which is hereby incorporated by reference). According to this numbering, FP1 of a sdAb comprises the amino acid residues at positions 1-30, CDP1 of a sdAb comprises the amino acid residues at positions 31-36, FR2 of a sdAb comprises the amino acids at positions 36-49, CDR2 of a sdAb comprises the amino acid residues at positions 50-65, FN1 of a sdAb comprises the amino acid residues at positions 66-94, CDN1 of a sdAb comprises the amino acid residues at positions 95-102, and FR4 of a sdAb comprises the amino acid residues at positions 103-113. Domain antibodies are also described in WO2004041862 and WO2016065323, each of which is hereby incorporated by reference. The domain antibodies can be a targeting moiety as described herein.

Antibody molecules can be monospecific (e.g., monovalent or bivalent), bispecific (e.g., bivalent, trivalent, tetravalent, pentavalent, or hexavalent), trispecific (e.g., trivalent, tetravalent, pentavalent, hexavalent), or with higher orders of specificity (e.g, tetraspecific) and/or higher orders of valency beyond hexavalency. An antibody molecule can comprise a functional fragment of a light chain variable region and a functional fragment of a heavy chain variable region, or heavy and light chains may be fused together into a single polypeptide. Effector, as that term is used herein, refers to an entity, e.g., a cell or molecule, e.g., a soluble or cell surface molecule, which mediates an immune response. In some embodiments, the effector is an antibody. In some embodiments, the effectors binding domains as provided for herein, refers to a polypeptide (e.g.) that has sufficient binding specificity that it can bind the effector with sufficient specificity that it can serve as an effector binding/modulating molecule. In some embodiments, it binds to effector with at least 10, 20, 30, 40, 50, 60, 70, 80, 90, or 95% of the affinity of the naturally occurring counter-ligand. In some embodiments, it has at least 60, 70, 80, 90, 95, 99, or 100% sequence identity, or substantial sequence identity, with a naturally occurring counter-ligand for the effector.

Elevated risk, as used herein, refers to the risk of a disorder in a subject, wherein the subject has one or more of a medical history of the disorder or a symptom of the disorder, a biomarker associated with the disorder or a symptom of the disorder, or a family history of the disorder or a symptom of the disorder.

The domains can have similarity to those as provided for herein or those that are incorporated by reference. Sequence identity, percentage identity, and related terms, as those terms are used herein, refer to the relatedness of two sequences, e.g., two nucleic acid sequences or two amino acid or polypeptide sequences. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%. 91%, 92%, 93%, 94%, 95%, 96%, 97%, 98% or 99% identity to a reference sequence, e.g., an amino acid sequence provided herein.

In the context of nucleotide sequence, such as those encoding for the domains, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., an amino acid sequence provided herein.

The term "functional variant" refers to polypeptides that have a substantially identical amino acid sequence to the naturally-occurring sequence, or are encoded by a substantially identical nucleotide sequence, and are capable of having one or more activities of the naturally-occurring sequence. For example, a Fc variant can have the amino acid sequence of a Fc polypeptide but comprise a mutation that prevents or disrupts cleavage by a protease.

Calculations of homology or sequence identity between sequences (the terms are used interchangeably herein) can be performed as follows.

To determine the percent identity of two amino acid sequences, or of two nucleic acid sequences, the amino acid sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the amino acid sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) J. Mol. Biol. 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215: 403-10. BLAST nucleotide searches can be performed with the NBLAST program, score=100, wordlength=12 to obtain nucleotide sequences homologous to for example any a nucleic acid sequence provided herein. BLAST protein searches can be performed with the XBLAST program, score=50, wordlength=3 to obtain amino acid sequences homologous to protein molecules provided herein. To obtain gapped alignments for comparison purposes, Gapped BLAST can be utilized as described in Altschul et al., (1997) Nucleic Acids Res. 25:3389-3402. When utilizing BLAST and Gapped BLAST programs, the default parameters of the respective programs (e.g., XBLAST and NBLAST) can be used. See http://www.ncbi.nlm.nih.gov.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° ° C., followed by two washes in 0.2×SSC, 0.1% SDS at least at 50° C. (the temperature of the washes can be increased to 55°C for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

It is understood that the molecules of the present embodiments may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The molecules and polypeptides provided for herein can be used to treat diseases and conditions mediated by IgG. Thus, embodiments are provided for methods of treating an IgG mediated disease or disorder in a subject. In some embodiments, the IgG mediated disease or disorder is an autoimmune disease or disorder. In some embodiments, the methods comprise administering to the subject a polypeptide, molecule, compound, or compositions as provided for herein. In some embodiments, the subject has or is at risk of having an IgG mediated disease or disorder. In some embodiments, the subject has or is at risk of having an autoimmune disease or disorder.

Antibody-mediated rejection (AMR) causes severe and rapid dysfunction and loss of allografts. Without wishing to be bound to a particular theory, the most common mechanism underlying AMR is an anamnestic response that originates from previous antigenic exposure. These donor specific antibody (DSA) responses are usually robust and result in the rapid production of high levels of DSA and acute allograft dysfunction. The mechanism of injury in AMR involves antigens that initiate the production of DSAs resulting in antigen-antibody interactions, complement activation and inflammation, and the resultant donor tissue damage. The impact of AMR on graft survival is dramatic and continues long after the initial inflammatory condition has resolved as was recently demonstrated in a study by LeFaucheur and Glotz. In this single center study of a large cohort of sensitized recipients, the investigators compared allograft survival for recipients successfully treated for AMR versus those that never experienced AMR. In some embodiments, the molecules and polypeptides provided for herein can be used to treat AMR.

Non-limiting examples of IgG mediated diseases and disorders, such as autoimmune diseases or disorders, that can be treated with the molecules and polypeptides described herein include, but are not limited to, Addison's disease, Anti-GBM glomerulonephritis, anti-neutrophil cytoplasmic antibody-associated vasculitides, ANCA associated vasculitis, granulomatous polyangiitis (Wegener granulomatosis), eosinophilic granulomatosis with polyangiitis (Churg-Strauss syndrome), microscopic polyangiitis, anti-NMDAR encephalitis, anti-phospholipid antibody syndrome (APS) and catastrophic APS, autoimmune bullous skin diseases, pemphigus, *Pemphigus foliaceus* (PF), fogo selvage (FS), *Pemphigus vulgaris* (PV), autoimmune hemolytic anemia (AIHA), autoimmune hepatitis (AIH), autoimmune neutropenia (AIN), bullous pemphigoid (BP), Celiac's disease, chronic urticaria, complete congenital heart block (CCHB), diabetes type 1A (T1DM), epidermolysis bullosa acquisita (EBA), essential mixed cryoglobulinemia, Goodpasture's syndrome, anti-glomerular basement membrane disease, Graves' disease, Goitre, hyperthyroidism, infiltrative exophthalmos, infiltrative dermopathy, Guillain-Barre syndrome (GBS), acute inflammatory demyelinating polyneuropathy (AIDP), acute motor axonal neuropathy (AMAN), hemophilia, acquired FVII deficiency, idiopathic thrombocytopenia purpura (ITP), Lambert-Eaton myasthenic syndrome (LEMS), mixed connective tissue disease (MCTD), multiple myeloma, myasthenia gravis, myasthenic crisis, myocarditis, dilated cardiomyopathy (DCM), congestive cardiomyopathy, neuromyelitis optica (NMO), primary biliary cirrhosis (PBC), primary progressive multiple sclerosis (PPMS), relapsing-rheumatic multiple sclerosis, acute exacerbation of multiple sclerosis, rheumatic heart disease (RHD), rheumatoid arthritis (RA), serum-sickness, immune complex hypersensitivity (type III), Sjögren's syndrome (SS), lupus nephritis, systemic lupus erythematosus (SLE), cutaneous lupus (CLE), transplant rejection, thrombotic thrombocytopenia purpura (TTP), idiopathic inflammatory myopathies, polymyositis, dermatomyositis, inclusion body myositis, uveitis, scleritis, ankylosing spondylitis, axial spondyloarthritis, reactive arthritis, psoriatic arthritis, IBD-associated arthritis, antiphospholipid syndrome, systemic sclerosis, giant cell arteritis, polymyalgia rheumatic, Takayasu's arteritis, anti-neutrophil cytoplasmic antibody associated vasculitis, Henoch-Schonlein purpura, polyarteritis nodosa, Cogan's syndrome, Buerger's disease, Susan's disease, immune complex vasculitis, primary angiitis of the central nervous system (CNS), Behcet's disease, relapsing polychondritis, juvenile idiopathic arthritis, juvenile dermatomyositis, autoimmune brain disease, sarcoidosis, neurosarcoidosis, IgG4-related diseases, autoimmune complications of immune checkpoint inhibitors (IRAEs), adult onset Still's disease, warm antibody hemolytic anemia (wAIHA), immune thrombocytopenia, immune thrombotic thrombocytopenia, thrombic thrombocytopenia, pernicious anemia, aplastic anemia, Evan's syndrome, autoimmune neutropenia, acquired von Willibrand syndrome, recurring fetal loss, Rh mismatch, ulcerative colitis, autoimmune hepatitis, autoimmune pancreatitis, eosinophilic esophagitis/gastritis, primary sclerosing cholangitis, primary biliary sclerosis, glomerulonephritis, glomerular basement membrane disease, scleritis/episcleritis, uveitis, conjunctivitis, keratitis, type I diabetes mellitus, Hashimoto's thyroiditis, polyglandular autoimmune endocrine syndromes, atopic dermatitis, dermatitis herpetiformis, *Pemphigus foliaceus*, fogo selvagem, cutaneous lupus erythematosus, linear IgA disease, Lichen planus, transplantation, antibody-mediated rejection, alloantibody hypersensitization, xenoantibody mediated rejection, solid organ rejection, graft vs. host disease (GVHD), multiple sclerosis, neuromyelitis optica, amyotrophic lateral sclerosis, Parkinson's disease, autoimmune encephalitis, CNS vasculitis, chronic idiopathic demyletinating polyneuropathy, transverse myelitis, optic neuritis, anti-myelin oligodendrocyte glycoprotein (MOG) disease, chronic meningitis, rheumatic heart disease, infectious disease, vaccination, antibody dependent enhancement, antibody to therapeutic biologic agents (cytokines, monoclonal antibodies, enzymes, coagulation factors), allergic asthma, cosinophilic pneumonia, nonspecific interstitial pneumonia, rheumatoid arthritis-associated interstitial lung disease (RA-ILD), sarcoidosis, hypersensitive pneumonitis, allergic bronchopulmonary mycosis, chronic rhinosinusitis with nasal polyps, and the like.

In some embodiments, the condition or disease to be treated is a neoplastic disorder, such as a cancer. In some embodiments, the cancer is a solid or liquid tumor. In some embodiments, the liquid or solid tumor include, but are not limited to, hematopoietic cancer, lymphoid cancer, skin cancer, head and neck cancer, genitourinary cancer, blood cancer, lung cancer, breast cancer, brain cancer, esophageal cancer, colorectal cancer, pancreatic cancer, and any combination thereof.

Pharmaceutical Compositions and Kits

In some embodiments, the present embodiments provide compositions, e.g., pharmaceutically acceptable compositions, which include a therapeutic compound described herein, formulated together with a pharmaceutically acceptable carrier. As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, local, ophthalmic, topical, spinal or epidermal administration (e.g. by injection or infusion). As used herein, the term "carrier" means a diluent, adjuvant, or excipient with which a compound is administered. In some embodiments, pharmaceutical carriers can also be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used. The carriers can be used in pharmaceutical compositions comprising the therapeutic compounds provided for herein.

The compositions and compounds of the embodiments provided for herein may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Typical compositions are in the form of injectable or infusible solutions. In some embodiments, the mode of administration is parenteral (e.g., intravenous, subcutaneous, intraperitoneal, intramuscular). In some embodiments, the therapeutic molecule is administered by intravenous infusion or injection. In another embodiment, the therapeutic molecule is administered by intramuscular or subcutaneous injection. In another embodiment, the therapeutic molecule is administered locally, e.g., by injection, or topical application, to a target site.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The compositions typically should be sterile and stable under the conditions of manufacture and storage. The composition can be formulated as a solution, microemulsion, dispersion, liposome, or other ordered structure suitable to high therapeutic molecule concentration. Sterile injectable solutions can be prepared by incorporating the active compound (i.e., therapeutic molecule) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. Sec, e.g., Sustained and Controlled Release Drug Delivery Systems, J. R. Robinson, ed., Marcel Dekker, Inc., New York, 1978.

In certain embodiments, a therapeutic compound can be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound by other than parenteral administration, it may be necessary to coat the compound with, or co-administer the compound with, a material to prevent its inactivation. Therapeutic compositions can also be administered with medical devices known in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of a therapeutic compound is 0.1-30 mg/kg, more preferably 1-25 mg/kg. Dosages and therapeutic regimens of the therapeutic compound can be determined by a skilled artisan. In certain embodiments, the therapeutic compound is administered by injection (e.g., subcutaneously or intravenously) at a dose of about 1 to 40 mg/kg, e.g., 1 to 30 mg/kg, e.g., about 5 to 25 mg/kg, about 10 to 20 mg/kg, about 1 to 5 mg/kg, 1 to 10 mg/kg, 5 to 15 mg/kg, 10 to 20 mg/kg. 15 to 25 mg/kg, or about 3 mg/kg. The dosing schedule can vary from e.g., once a week to once every 2, 3, or 4 weeks. In one embodiment, the therapeutic compound is administered at a dose from about 10 to 20 mg/kg every other week. The therapeutic compound can be administered by intravenous infusion at a rate of more than 20 mg/min, e.g., 20-40 mg/min, and typically greater than or equal to 40 mg/min to reach a dose of about 35 to 440 mg/m$^2$, typically about 70 to 310 mg/m$^2$, and more typically, about 110 to 130 mg/m$^2$. In embodiments, the infusion rate of about 110 to 130 mg/m$^2$ achieves a level of about 3 mg/kg. In other embodiments, the therapeutic compound can be administered by intravenous infusion at a rate of less than 10 mg/min, e.g., less than or equal to 5 mg/min to reach a dose of about 1 to 100 mg/m$^2$, e.g., about 5 to 50 mg/m$^2$, about 7 to 25 mg/m$^2$, or, about 10 mg/m$^2$. In some embodiments, the therapeutic compound is infused over a period of about 30 min. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions may include a "therapeutically effective amount" or a "prophylactically effective amount" of a therapeutic molecule. A "therapeutically effective amount" refers to an amount effective, at dosages and for periods of time necessary, to achieve the desired therapeutic result. A therapeutically effective amount of a therapeutic molecule may vary according to factors such as the disease state, age, sex, and weight of the individual, and the ability of the therapeutic compound to elicit a desired response in the individual. A therapeutically effective amount is also one in which any toxic or detrimental effects of a therapeutic molecule is outweighed by the therapeutically beneficial effects. A "therapeutically effective dosage" preferably inhibits a measurable parameter, e.g., immune attack at least about 20%, more preferably by at least about 40%, even more preferably by at least about 60%, and still more preferably by at least about 80% relative to untreated subjects. The ability of a compound to inhibit a measurable parameter, e.g., immune attack, can be evaluated in an animal model system predictive of efficacy in transplant rejection or autoimmune disorders. Alternatively, this property of a composition can be evaluated by examining the ability of the compound to inhibit, such inhibition in vitro by assays known to the skilled practitioner. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within the scope of the embodiments is a kit comprising a therapeutic compound described herein. The kit can include one or more other elements including: instructions for use; other reagents, e.g., a label, a therapeutic agent, or an agent useful for chelating, or otherwise coupling, a therapeutic molecule to a label or other therapeutic agent, or a radioprotective composition; devices or other materials for preparing the a therapeutic molecule for administration; pharmaceutically acceptable carriers; and devices or other materials for administration to a subject.

The following examples are illustrative, but not limiting, of the compounds, compositions and methods described herein. Other suitable modifications and adaptations known to those skilled in the art are within the scope of the following embodiments.

Enumerated Embodiments

1. A variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 1, provided that the variant Fc polypeptide comprises a set of mutations selected from:
   L234A, L235A, G237A, Y296Q, and P329K;
   L234A, L235A, G237A, Y296Q, S298K, and P329K;
   L234A, L235A, G237A, D265K, E269S, Y296Q, and P329K; or
   L234A, L235A, G237A, D265K, E269S, Y296Q, S298K, and P329K;
   as compared to SEQ ID NO: 1.
2. The variant Fc polypeptide of embodiment 1, wherein the variant Fc polypeptide comprises a set of L234A, L235A, G237A, Y296Q, and P329K mutations, as compared to SEQ ID NO: 1.
3. The variant Fc polypeptide of embodiment 1, wherein the variant Fc polypeptide comprises a set of L234A, L235A, G237A, Y296Q, S298K, and P329K mutations, as compared to SEQ ID NO: 1.
4. The variant Fc polypeptide of embodiment 1, wherein the variant Fc polypeptide comprises a set of L234A, L235A, G237A, D265K, E269S, Y296Q, and P329K mutations, as compared to SEQ ID NO: 1.
5. The variant Fc polypeptide of embodiment 1, wherein the variant Fc polypeptide comprises a set of L234A, L235A, G237A, D265K, E269S, Y296Q, S298K, and P329K mutations, as compared to SEQ ID NO: 1.
6. The variant Fc polypeptide of any one of embodiments 1-5, wherein the variant Fc polypeptide is resistant to proteolytic cleavage.

7. The variant Fc polypeptide of any one of embodiments 1-5, wherein the variant Fc polypeptide is resistant to binding by a protease.
8. The variant Fc polypeptide of any one of embodiments 1-5, wherein the variant Fc polypeptide is resistant to proteolytic cleavage and binding by a protease.
9. A variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, 20, 21, 22, 23, 24, or 25, provided that the variant Fc polypeptide comprises a set of mutations selected from:
- L234A, L235A, G237A, Y296Q, and P329K;
- L234A, L235A, G237A, Y296Q, S298K, and P329K;
- L234A, L235A, G237A, D265K, E269S, Y296Q, and P329K; or
- L234A, L235A, G237A, D265K, E269S, Y296Q, S298K, and P329K;

as compared to SEQ ID NO: 19, 20, 21, 22, 23, 24, or 25.
10. The variant Fc polypeptide of embodiment 9, wherein the variant IgG Fc comprises:
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, provided that the variant Fc polypeptide comprises a set of L234A, L235A, G237A, Y296Q, and P329K mutations, as compared to SEQ ID NO: 19;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20, provided that the variant Fc polypeptide comprises a set of L234A, L235A, G237A, Y296Q, and P329K mutations, as compared to SEQ ID NO: 20;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21, provided that the variant Fc polypeptide comprises a set of L234A, L235A, G237A, Y296Q, and P329K mutations, as compared to SEQ ID NO: 21;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22, provided that the variant Fc polypeptide comprises a set of L234A, L235A, G237A, Y296Q, and P329K mutations, as compared to SEQ ID NO: 22;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23, provided that the variant Fc polypeptide comprises a set of L234A, L235A, G237A, Y296Q, and P329K mutations, as compared to SEQ ID NO: 23;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24, provided that the variant Fc polypeptide comprises a set of L234A, L235A, G237A, Y296Q, and P329K mutations, as compared to SEQ ID NO: 24;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25, provided that the variant Fc polypeptide comprises a set of L234A, L235A, G237A, Y296Q, and P329K mutations, as compared to SEQ ID NO: 25;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, provided that the variant Fc polypeptide comprises a set of L234A, L235A, G237A, Y296Q, S298K, and P329K mutations, as compared to SEQ ID NO: 19;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20, provided that the variant Fc polypeptide comprises a set of L234A, L235A, G237A, Y296Q, S298K, and P329K mutations, as compared to SEQ ID NO: 20;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21, provided that the variant Fc polypeptide comprises a set of L234A, L235A, G237A, Y296Q, S298K, and P329K mutations, as compared to SEQ ID NO: 21;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22, provided that the variant Fc polypeptide comprises a set of L234A, L235A, G237A, Y296Q, S298K, and P329K mutations, as compared to SEQ ID NO: 22;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23, provided that the variant Fc polypeptide comprises a set of L234A, L235A, G237A, Y296Q, S298K, and P329K mutations, as compared to SEQ ID NO: 23;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24, provided that the variant Fc polypeptide comprises a set of L234A, L235A, G237A, Y296Q, S298K, and P329K mutations, as compared to SEQ ID NO: 24;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25, provided that the variant Fc polypeptide comprises a set of L234A, L235A, G237A, Y296Q, S298K, and P329K mutations, as compared to SEQ ID NO: 25;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, provided that the variant Fc polypeptide comprises a set of L234A, L235A, G237A, D265K, E269S, Y296Q, and P329K mutations, as compared to SEQ ID NO: 19;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20, provided that the variant Fc polypeptide comprises a set of L234A, L235A, G237A, D265K, E269S, Y296Q, and P329K mutations, as compared to SEQ ID NO: 20;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21, provided that the variant Fc polypeptide comprises a set of L234A, L235A, G237A, D265K, E269S, Y296Q, and P329K mutations, as compared to SEQ ID NO: 21;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22, provided that the variant Fc polypeptide comprises a set of L234A, L235A, G237A, D265K, E269S, Y296Q, and P329K mutations, as compared to SEQ ID NO: 22;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23, provided that the variant Fc polypeptide comprises a set of L234A, L235A, G237A, D265K, E269S, Y296Q, and P329K mutations, as compared to SEQ ID NO: 23;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24, provided that the variant Fc polypeptide comprises a set of L234A, L235A, G237A, D265K, E269S, Y296Q, and P329K mutations, as compared to SEQ ID NO: 24;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25, provided that the variant Fc polypeptide comprises a set of L234A, L235A, G237A, D265K, E269S, Y296Q, and P329K mutations, as compared to SEQ ID NO: 25;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, provided that the variant Fc polypeptide comprises a set of L234A, L235A, G237A, D265K, E269S, Y296Q, S298K, and P329K mutations, as compared to SEQ ID NO: 19;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20, provided that the variant Fc polypeptide comprises a set of L234A, L235A, G237A, D265K, E269S, Y296Q, S298K, and P329K mutations, as compared to SEQ ID NO: 20;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21, provided that the variant Fc polypeptide comprises a set of L234A, L235A, G237A, D265K, E269S, Y296Q, S298K, and P329K mutations, as compared to SEQ ID NO: 21;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22, provided that the variant Fc polypeptide comprises a set of L234A, L235A, G237A, D265K, E269S, Y296Q, S298K, and P329K mutations, as compared to SEQ ID NO: 22;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23, provided that the variant Fc polypeptide comprises a set of L234A, L235A, G237A, D265K, E269S, Y296Q, S298K, and P329K mutations, as compared to SEQ ID NO: 23;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24, provided that the variant Fc polypeptide comprises a set of L234A, L235A, G237A, D265K, E269S, Y296Q, S298K, and P329K mutations, as compared to SEQ ID NO: 24; or an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25, provided that the variant Fc polypeptide comprises a set of L234A, L235A, G237A, D265K, E269S, Y296Q, S298K, and P329K mutations, as compared to SEQ ID NO: 25.

11. The variant Fc polypeptide of any one of embodiments 9-10, wherein the variant Fc polypeptide is resistant to cleavage by a protease, or a variant thereof.

12. The variant Fc polypeptide of any one of embodiments 9-10, wherein the variant Fc polypeptide is resistant to binding by a protease, or a variant thereof.

13. The variant Fc polypeptide of any one of embodiments 9-12, wherein the variant Fc polypeptide is resistant to cleavage by a protease, or a variant thereof, and binding by a protease, or a variant thereof.

14. A variant Fc polypeptide comprising:
    an amino acid sequence of SEQ ID NO: 19;
    an amino acid sequence of SEQ ID NO: 21;
    an amino acid sequence of SEQ ID NO: 22;
    an amino acid sequence of SEQ ID NO: 23;
    an amino acid sequence of SEQ ID NO: 24; or
    an amino acid sequence of SEQ ID NO: 25.

15. The variant Fc polypeptide of any one of embodiments 1-14, wherein the variant Fc polypeptide is resistant to cleavage by a protease, or a variant thereof, and/or binding by a protease, or a variant thereof.

16. The variant Fc polypeptide of any one of embodiments 1-15, wherein the variant Fc polypeptide is covalently or non-covalently conjugated to a polypeptide having IgG protease activity, wherein the polypeptide having IgG protease activity can be conjugated to N-terminus or C-terminus of the variant Fc polypeptide.

17. The variant Fc polypeptide of embodiment 15, wherein the polypeptide having IgG protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 26, 28, 29, 31, 36, 37, 38, 39, 40, 41, 50, 51, 52, or 55.

18. The variant Fc polypeptide of any one of embodiments 16-17, wherein the polypeptide having IgG protease activity comprises an amino acid sequence of SEQ ID NO: 26, 28, 29, 31, 36, 37, 38, 39, 40, 41, 50, 51, 52, or 55.

19. The variant Fc polypeptide of embodiment 17, wherein the polypeptide having IgG protease activity is as effective, or more effective at cleaving IgG than the wild-type protease, and/or is less immunogenic, or as immunogenic, as the wild-type protease.

20. A polypeptide comprising a polypeptide having protease activity and an Fc polypeptide, wherein the polypeptide having protease activity is covalently or non-covalently connected (e.g. conjugated via a peptide bond or through electrostatic interactions) to the Fc polypeptide.

21. The polypeptide of embodiment 20, wherein the polypeptide having protease activity is a polypeptide having IgG cleaving protease activity.

22. The polypeptide of embodiment 21, wherein the polypeptide having IgG cleaving protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 26, 28, 29, 31, 36, 37, 38, 39, 40, 41, 50, 51, 52, or 55.

23. The polypeptide of any one of embodiments 21-22, wherein the polypeptide having IgG cleaving protease activity comprises an amino acid sequence of SEQ ID NO: 26, 28, 29, 31, 36, 37, 38, 39, 40, 41, 50, 51, 52, or 55.

24. The polypeptide of any one of embodiments 20-23, wherein the polypeptide having IgG cleaving protease activity is selected a IdeS, IdeSsuis, IdeE, IdeZ, IdeE2, IdeZ2, or IdeC protease, or a variant thereof.

25. The polypeptide of embodiment 20, wherein the Fc polypeptide is resistant to cleavage by a protease, or a variant thereof, and/or binding by a protease, or a variant thereof.

26. The polypeptide of any one of embodiments 20-25, wherein the Fc polypeptide is a variant Fc polypeptide.

27. The polypeptide of embodiment 26, wherein the variant Fc polypeptide comprises an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 1, provided that the variant Fc polypeptide comprises a mutation set selected from:
  L234A, L235A, G237A, Y296Q, and P329K;
  L234A, L235A, G237A, Y296Q, S298K, and P329K;
  L234A, L235A, G237A, D265K, E269S, Y296Q, and P329K; or
  L234A, L235A, G237A, D265K, E269S, Y296Q, S298K, and P329K.

28. The polypeptide of any one of embodiments 26-27, wherein the variant Fc polypeptide comprises mutations corresponding to L234A, L235A, G237A, Y296Q, and P329K according to SEQ ID NO: 1.

29. The polypeptide of any one of embodiments 26-27, wherein the variant Fc polypeptide comprises mutations corresponding to L234A, L235A, G237A, Y296Q, S298K, and P329K according to SEQ ID NO: 1.

30. The polypeptide of any one of embodiments 26-27, wherein the variant Fc polypeptide comprises mutations corresponding to L234A, L235A, G237A, D265K, E269S, Y296Q, and P329K according to SEQ ID NO: 1.

31. The polypeptide of any one of embodiments 26-27, wherein the variant Fc polypeptide comprises mutations corresponding to L234A, L235A, G237A, D265K, E269S, Y296Q, S298K, and P329K according to SEQ ID NO: 1.

32. The polypeptide of any one of embodiments 26-31, wherein the variant Fc polypeptide comprises an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, 20, 21, 22, 23, 24, or 25, provided that the variant Fc polypeptide comprises a set of mutations selected from:
  L234A, L235A, G237A, Y296Q, and P329K;
  L234A, L235A, G237A, Y296Q, S298K, and P329K;
  L234A, L235A, G237A, D265K, E269S, Y296Q, and P329K; or
  L234A, L235A, G237A, D265K, E269S, Y296Q, S298K, and P329K;
  as compared to SEQ ID NO: 19, 20, 21, 22, 23, 24, or 25.

33. The polypeptide of embodiment 32, wherein the variant IgG Fc comprises:
  an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, provided that the variant Fc polypeptide comprises a set of L234A, L235A, G237A, Y296Q, and P329K mutations, as compared to SEQ ID NO: 19;
  an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20, provided that the variant Fc polypeptide comprises a set of L234A, L235A, G237A, Y296Q, and P329K mutations, as compared to SEQ ID NO: 20;
  an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21, provided that the variant Fc polypeptide comprises a set of L234A, L235A, G237A, Y296Q, and P329K mutations, as compared to SEQ ID NO: 21;
  an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22, provided that the variant Fc polypeptide comprises a set of L234A, L235A, G237A, Y296Q, and P329K mutations, as compared to SEQ ID NO: 22;
  an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23, provided that the variant Fc polypeptide comprises a set of L234A, L235A, G237A, Y296Q, and P329K mutations, as compared to SEQ ID NO: 23;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24, provided that the variant Fc polypeptide comprises a set of L234A, L235A, G237A, Y296Q, and P329K mutations, as compared to SEQ ID NO: 24;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25, provided that the variant Fc polypeptide comprises a set of L234A, L235A, G237A, Y296Q, and P329K mutations, as compared to SEQ ID NO: 25;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, provided that the variant Fc polypeptide comprises a set of L234A, L235A, G237A, Y296Q, S298K, and P329K mutations, as compared to SEQ ID NO: 19;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20, provided that the variant Fc polypeptide comprises a set of L234A, L235A, G237A, Y296Q, S298K, and P329K mutations, as compared to SEQ ID NO: 20;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21, provided that the variant Fc polypeptide comprises a set of L234A, L235A, G237A, Y296Q, S298K, and P329K mutations, as compared to SEQ ID NO: 21;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22, provided that the variant Fc polypeptide comprises a set of L234A, L235A, G237A, Y296Q, S298K, and P329K mutations, as compared to SEQ ID NO: 22;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23, provided that the variant Fc polypeptide comprises a set of L234A, L235A, G237A, Y296Q, S298K, and P329K mutations, as compared to SEQ ID NO: 23;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24, provided that the variant Fc polypeptide comprises a set of L234A, L235A, G237A, Y296Q, S298K, and P329K mutations, as compared to SEQ ID NO: 24;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25, provided that the variant Fc polypeptide comprises a set of L234A, L235A, G237A, Y296Q, S298K, and P329K mutations, as compared to SEQ ID NO: 25;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, provided that the variant Fc polypeptide comprises a set of L234A, L235A, G237A, D265K, E269S, Y296Q, and P329K mutations, as compared to SEQ ID NO: 19;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20, provided that the variant Fc polypeptide comprises a set of L234A, L235A, G237A, D265K, E269S, Y296Q, and P329K mutations, as compared to SEQ ID NO: 20;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21, provided that the variant Fc polypeptide comprises a set of L234A, L235A, G237A, D265K, E269S, Y296Q, and P329K mutations, as compared to SEQ ID NO: 21;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22, provided that the variant Fc polypeptide comprises a set of L234A, L235A, G237A, D265K, E269S, Y296Q, and P329K mutations, as compared to SEQ ID NO: 22;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23, provided that the variant Fc polypeptide comprises a set of L234A, L235A, G237A, D265K, E269S, Y296Q, and P329K mutations, as compared to SEQ ID NO: 23;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24, provided that the variant Fc polypeptide comprises a set of L234A, L235A, G237A, D265K, E269S, Y296Q, and P329K mutations, as compared to SEQ ID NO: 24;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25, provided that the variant Fc polypeptide comprises a set of L234A, L235A, G237A, D265K, E269S, Y296Q, and P329K mutations, as compared to SEQ ID NO: 25;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, provided that the variant Fc polypeptide comprises a set of L234A, L235A, G237A, D265K, E269S, Y296Q, S298K, and P329K mutations, as compared to SEQ ID NO: 19;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20, provided that the variant Fc polypeptide comprises a set of L234A, L235A, G237A, D265K, E269S, Y296Q, S298K, and P329K mutations, as compared to SEQ ID NO: 20;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21, provided that the variant Fc polypeptide comprises a set of L234A, L235A, G237A, D265K, E269S, Y296Q, S298K, and P329K mutations, as compared to SEQ ID NO: 21;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22, provided that the variant Fc polypeptide comprises a set of L234A, L235A, G237A, D265K, E269S, Y296Q, S298K, and P329K mutations, as compared to SEQ ID NO: 22;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23, provided that the variant Fc polypeptide comprises a set of L234A, L235A, G237A, D265K, E269S, Y296Q, S298K, and P329K mutations, as compared to SEQ ID NO: 23;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24, provided that the variant Fc polypeptide comprises a set of L234A, L235A, G237A, D265K, E269S, Y296Q, S298K, and P329K mutations, as compared to SEQ ID NO: 24; or an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25, provided that the variant Fc polypeptide comprises a set of L234A, L235A, G237A, D265K, E269S, Y296Q, S298K, and P329K mutations, as compared to SEQ ID NO: 25.

34. The polypeptide of any one of embodiments 26-33, wherein the variant Fc polypeptide comprises:
an amino acid sequence of SEQ ID NO: 19;
an amino acid sequence of SEQ ID NO: 21;
an amino acid sequence of SEQ ID NO: 22;
an amino acid sequence of SEQ ID NO: 23;
an amino acid sequence of SEQ ID NO: 24; or
an amino acid sequence of SEQ ID NO: 25.

35. The polypeptide of any one of embodiments 20-34, wherein the polypeptide having protease activity is covalently or non-covalently conjugated to the N-terminus of the Fc polypeptide.

36. The polypeptide of any one of embodiments 20-34, wherein the polypeptide having protease activity is covalently or non-covalently conjugated to the C-terminus of the Fc polypeptide.

37. The polypeptide of any one of embodiments 20-36, wherein the polypeptide further comprises a nanobody.

38. The polypeptide of embodiment 37, wherein the nanobody comprises an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 30, 32, or 33.

39. The polypeptide of embodiment 38, wherein the nanobody is covalently or non-covalently conjugated to the N-terminus or the C-terminus of the polypeptide having protease activity.

40. The polypeptide of embodiment 38, wherein the polypeptide having protease activity is covalently or non-covalently conjugated to the N-terminus or the C-terminus of the Fc polypeptide.

41. The polypeptide of embodiment 38, wherein the nanobody is covalently or non-covalently conjugated to the N-terminus of the Fc polypeptide, and wherein the C-terminus of the Fc polypeptide is covalently or non-covalently conjugated to the N-terminus of the polypeptide having protease activity.

42. The polypeptide of embodiment 38, wherein the polypeptide having protease activity is covalently or non-covalently conjugated to the C-terminus of the Fc polypeptide, and wherein the N-terminus of the Fc polypeptide is covalently or non-covalently conjugated to the C-terminus of the polypeptide having protease activity.

43. A polypeptide having a formula from N-terminus to C-terminus selected from:

N1-P1-variant Fc;

variant Fc-P1-N1;

P1-variant Fc-N1; or

N1-variant Fc-P1, wherein,
P1 comprises a polypeptide having protease activity;
N1 comprises a nanobody; and
variant Fc is a variant Fc polypeptide.

44. The polypeptide of embodiment 43, wherein the polypeptide having protease activity is a polypeptide having IgG cleaving protease activity.

45. The polypeptide of embodiment 44, wherein the polypeptide having IgG cleaving protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 26, 28, 29, 31, 36, 37, 38, 39, 40, 41, 50, 51, 52, or 55.

46. The polypeptide of any one of embodiments 43-45, wherein the polypeptide having IgG cleaving protease activity comprises an amino acid sequence of SEQ ID NO: 26, 28, 29, 31, 36, 37, 38, 39, 40, 41, 50, 51, 52, or 55.

47. The polypeptide of any one of embodiments 43-46, wherein the polypeptide having protease activity is selected from IdeS, IdeSsuis, IdeE, IdeZ, IdeE2, IdeZ2, or IdeC protease, or a variant thereof.

48. The polypeptide of embodiment 47, wherein the polypeptide having protease activity is IdeS protease, or a variant thereof.

49. The polypeptide of embodiment 43, wherein the variant Fc molecule is a variant Fc polypeptide.

50. The polypeptide of embodiment 49, wherein the variant Fc polypeptide comprises an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 1, provided that the variant Fc polypeptide comprises a mutation set selected from:
  L234A, L235A, G237A, Y296Q, and P329K;
  L234A, L235A, G237A, Y296Q, S298K, and P329K;
  L234A, L235A, G237A, D265K, E269S, Y296Q, and P329K; or
  L234A, L235A, G237A, D265K, E269S, Y296Q, S298K, and P329K.

51. The polypeptide of any one of embodiments 49-50, wherein the variant Fc polypeptide comprises mutations corresponding to L234A, L235A, G237A, Y296Q, and P329K according to SEQ ID NO: 1.

52. The polypeptide of any one of embodiments 49-50, wherein the variant Fc polypeptide comprises mutations corresponding to L234A, L235A, G237A, Y296Q, S298K, and P329K according to SEQ ID NO: 1.

53. The polypeptide of any one of embodiments 49-50, wherein the variant Fc polypeptide comprises mutations corresponding to L234A, L235A, G237A, D265K, E269S, Y296Q, and P329K according to SEQ ID NO: 1.

54. The polypeptide of any one of embodiments 49-50, wherein the variant Fc polypeptide comprises mutations corresponding to L234A, L235A, G237A, D265K, E269S, Y296Q, S298K, and P329K according to SEQ ID NO: 1.

55. The polypeptide of any one of embodiments 49-54, wherein the variant Fc polypeptide comprises an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, 20, 21, 22, 23, 24, or 25, provided that the variant Fc polypeptide comprises a set of mutations selected from:
  L234A, L235A, G237A, Y296Q, and P329K;
  L234A, L235A, G237A, Y296Q, S298K, and P329K;
  L234A, L235A, G237A, D265K, E269S, Y296Q, and P329K; or
  L234A, L235A, G237A, D265K, E269S, Y296Q, S298K, and P329K;
  as compared to SEQ ID NO: 19, 20, 21, 22, 23, 24, or 25.

56. The polypeptide of embodiment 55, wherein the variant IgG Fc comprises:
  an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, provided that the variant Fc polypeptide comprises a set of L234A, L235A, G237A, Y296Q, and P329K mutations, as compared to SEQ ID NO: 19;
  an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20, provided that the variant Fc polypeptide comprises a set of L234A, L235A, G237A, Y296Q, and P329K mutations, as compared to SEQ ID NO: 20;
  an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21, provided that the variant Fc polypeptide comprises a set of L234A, L235A, G237A, Y296Q, and P329K mutations, as compared to SEQ ID NO: 21;
  an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22, provided that the variant Fc polypeptide comprises a set of L234A, L235A, G237A, Y296Q, and P329K mutations, as compared to SEQ ID NO: 22;
  an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23, provided that the variant Fc polypeptide comprises a set of L234A, L235A, G237A, Y296Q, and P329K mutations, as compared to SEQ ID NO: 23;
  an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24, provided that the variant Fc polypeptide comprises a set of L234A, L235A, G237A, Y296Q, and P329K mutations, as compared to SEQ ID NO: 24;
  an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25, provided that the variant Fc polypeptide comprises a set of L234A, L235A, G237A, Y296Q, and P329K mutations, as compared to SEQ ID NO: 25;
  an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, provided that the variant Fc polypeptide comprises a set of L234A, L235A, G237A, Y296Q, S298K, and P329K mutations, as compared to SEQ ID NO: 19;
  an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20, provided that the variant Fc polypeptide comprises a set of L234A, L235A, G237A, Y296Q, S298K, and P329K mutations, as compared to SEQ ID NO: 20;
  an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21, provided that the variant Fc polypeptide comprises a set of L234A, L235A, G237A, Y296Q, S298K, and P329K mutations, as compared to SEQ ID NO: 21;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22, provided that the variant Fc polypeptide comprises a set of L234A, L235A, G237A, Y296Q, S298K, and P329K mutations, as compared to SEQ ID NO: 22;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23, provided that the variant Fc polypeptide comprises a set of L234A, L235A, G237A, Y296Q, S298K, and P329K mutations, as compared to SEQ ID NO: 23;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24, provided that the variant Fc polypeptide comprises a set of L234A, L235A, G237A, Y296Q, S298K, and P329K mutations, as compared to SEQ ID NO: 24;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25, provided that the variant Fc polypeptide comprises a set of L234A, L235A, G237A, Y296Q, S298K, and P329K mutations, as compared to SEQ ID NO: 25;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, provided that the variant Fc polypeptide comprises a set of L234A, L235A, G237A, D265K, E269S, Y296Q, and P329K mutations, as compared to SEQ ID NO: 19;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20, provided that the variant Fc polypeptide comprises a set of L234A, L235A, G237A, D265K, E269S, Y296Q, and P329K mutations, as compared to SEQ ID NO: 20;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21, provided that the variant Fc polypeptide comprises a set of L234A, L235A, G237A, D265K, E269S, Y296Q, and P329K mutations, as compared to SEQ ID NO: 21;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22, provided that the variant Fc polypeptide comprises a set of L234A, L235A, G237A, D265K, E269S, Y296Q, and P329K mutations, as compared to SEQ ID NO: 22;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23, provided that the variant Fc polypeptide comprises a set of L234A, L235A, G237A, D265K, E269S, Y296Q, and P329K mutations, as compared to SEQ ID NO: 23;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24, provided that the variant Fc polypeptide comprises a set of L234A, L235A, G237A, D265K, E269S, Y296Q, and P329K mutations, as compared to SEQ ID NO: 24;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25, provided that the variant Fc polypeptide comprises a set of L234A, L235A, G237A, D265K, E269S, Y296Q, and P329K mutations, as compared to SEQ ID NO: 25;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, provided that the variant Fc polypeptide comprises a set of L234A, L235A, G237A, D265K, E269S, Y296Q, S298K, and P329K mutations, as compared to SEQ ID NO: 19;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20, provided that the variant Fc polypeptide comprises a set of L234A, L235A, G237A, D265K, E269S, Y296Q, S298K, and P329K mutations, as compared to SEQ ID NO: 20;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21, provided that the variant Fc polypeptide comprises a set of L234A, L235A, G237A, D265K, E269S, Y296Q, S298K, and P329K mutations, as compared to SEQ ID NO: 21;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22, provided that the variant Fc polypeptide comprises a set of L234A, L235A, G237A, D265K, E269S, Y296Q, S298K, and P329K mutations, as compared to SEQ ID NO: 22;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23, provided that the variant Fc polypeptide comprises a set of L234A, L235A, G237A, D265K, E269S, Y296Q, S298K, and P329K mutations, as compared to SEQ ID NO: 23;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24, provided that the variant Fc polypeptide comprises a set of L234A, L235A, G237A, D265K, E269S, Y296Q, S298K, and P329K mutations, as compared to SEQ ID NO: 24; or
an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25, provided that the variant Fc polypeptide comprises a set of L234A, L235A, G237A, D265K, E269S, Y296Q, S298K, and P329K mutations, as compared to SEQ ID NO: 25.

57. The polypeptide of any one of embodiments 49-56, wherein the variant Fc polypeptide comprises:
an amino acid sequence of SEQ ID NO: 19;
an amino acid sequence of SEQ ID NO: 21;
an amino acid sequence of SEQ ID NO: 22;
an amino acid sequence of SEQ ID NO: 23;
an amino acid sequence of SEQ ID NO: 24; or
an amino acid sequence of SEQ ID NO: 25.

58. The polypeptide of any one of embodiments 43-57, wherein the polypeptide further comprises a tag, such as a purification tag or detection tag (e.g., a His-tag).

59. The polypeptide of embodiment 58, wherein the tag is conjugated to the C-terminus of the polypeptide.

60. The polypeptide of any one of embodiments 58-59, wherein the His-tag has the amino acid sequence of SEQ ID NO: 27, or 34.

61. A polypeptide having a formula from N-terminus to C-terminus selected from:

N1-P1-variant Fc;

variant Fc-P1-N1;

P1-variant Fc-N1; or

N1-variant Fc-P1, wherein,
P1 comprises a polypeptide having protease activity;
N1 comprises a nanobody;
variant Fc is a variant Fc polypeptide; and
optionally wherein the protease is a glycosylation-resistant protease.

62. The polypeptide of embodiment 61, wherein the polypeptide having protease activity is a polypeptide having IgG cleaving protease activity.

63. The polypeptide of embodiment 62, wherein the polypeptide having IgG cleaving protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 26, 28, 29, 31, 36, 37, 38, 39, 40, 41, 50, 51, 52, or 55.

64. The polypeptide of any one of embodiments 61-63, wherein the polypeptide having IgG cleaving protease activity comprises an amino acid sequence of SEQ ID NO: 26, 28, 29, 31, 36, 37, 38, 39, 40, 41, 50, 51, 52, or 55.

65. The polypeptide of any one of embodiments 61-64, wherein the polypeptide having protease activity is selected from IdeS, IdeSsuis, IdeE, IdeZ, IdeE2, IdeZ2, or IdeC protease, or a variant thereof.

66. The polypeptide of any one of embodiments 61-65, wherein the polypeptide having protease activity comprises a mutation at one, or more, glycosylation sites.

67. The polypeptide of embodiment 61, wherein the variant Fc molecule is a variant Fc polypeptide.

68. The polypeptide of embodiment 67, wherein the variant Fc polypeptide comprises an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 1, provided that the variant Fc polypeptide comprises a mutation set selected from:
L234A, L235A, G237A, Y296Q, and P329K;
L234A, L235A, G237A, D265K, E269S, Y296Q, and P329K; or
L234A, L235A, G237A, D265K, E269S, Y296Q, S298K, and P329K.

69. The polypeptide of any one of embodiments 67-68, wherein the variant Fc polypeptide comprises mutations corresponding to L234A, L235A, G237A, Y296Q, and P329K according to SEQ ID NO: 1.

70. The polypeptide of any one of embodiments 67-68, wherein the variant Fc polypeptide comprises mutations corresponding to L234A, L235A, G237A, D265K, E269S, Y296Q, and P329K according to SEQ ID NO: 1.

71. The polypeptide of any one of embodiments 67-68, wherein the variant Fc polypeptide comprises mutations corresponding to L234A, L235A, G237A, D265K, E269S, Y296Q, S298K, and P329K according to SEQ ID NO: 1.

72. The polypeptide of any one of embodiments 67-68, wherein the variant Fc polypeptide comprises an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, 20, 21, 22, 23, 24, or 25, provided that the variant Fc polypeptide comprises a set of mutations selected from:
L234A, L235A, G237A, Y296Q, S298K, and P329K;
L234A, L235A, G237A, D265K, E269S, Y296Q, and P329K; or
L234A, L235A, G237A, D265K, E269S, Y296Q, S298K, and P329K;
as compared to SEQ ID NO: 19, 20, 21, 22, 23, 24, or 25.

73. The polypeptide of embodiment 72, wherein the variant IgG Fc comprises:
an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, provided that the variant Fc polypeptide comprises a set of L234A, L235A, G237A, Y296Q, S298K, and P329K mutations, as compared to SEQ ID NO: 19;
an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20, provided that the variant Fc polypeptide comprises a set of L234A, L235A, G237A, Y296Q, S298K, and P329K mutations, as compared to SEQ ID NO: 20;
an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21, provided that the variant Fc polypeptide comprises a set of L234A, L235A, G237A, Y296Q, S298K, and P329K mutations, as compared to SEQ ID NO: 21;
an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22, provided that the variant Fc polypeptide comprises a set of L234A, L235A, G237A, Y296Q, S298K, and P329K mutations, as compared to SEQ ID NO: 22;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23, provided that the variant Fc polypeptide comprises a set of L234A, L235A, G237A, Y296Q, S298K, and P329K mutations, as compared to SEQ ID NO: 23;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24, provided that the variant Fc polypeptide comprises a set of L234A, L235A, G237A, Y296Q, S298K, and P329K mutations, as compared to SEQ ID NO: 24;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25, provided that the variant Fc polypeptide comprises a set of L234A, L235A, G237A, Y296Q, S298K, and P329K mutations, as compared to SEQ ID NO: 25;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, provided that the variant Fc polypeptide comprises a set of L234A, L235A, G237A, D265K, E269S, Y296Q, and P329K mutations, as compared to SEQ ID NO: 19;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20, provided that the variant Fc polypeptide comprises a set of L234A, L235A, G237A, D265K, E269S, Y296Q, and P329K mutations, as compared to SEQ ID NO: 20;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21, provided that the variant Fc polypeptide comprises a set of L234A, L235A, G237A, D265K, E269S, Y296Q, and P329K mutations, as compared to SEQ ID NO: 21;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22, provided that the variant Fc polypeptide comprises a set of L234A, L235A, G237A, D265K, E269S, Y296Q, and P329K mutations, as compared to SEQ ID NO: 22;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23, provided that the variant Fc polypeptide comprises a set of L234A, L235A, G237A, D265K, E269S, Y296Q, and P329K mutations, as compared to SEQ ID NO: 23;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24, provided that the variant Fc polypeptide comprises a set of L234A, L235A, G237A, D265K, E269S, Y296Q, and P329K mutations, as compared to SEQ ID NO: 24;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25, provided that the variant Fc polypeptide comprises a set of L234A, L235A, G237A, D265K, E269S, Y296Q, and P329K mutations, as compared to SEQ ID NO: 25;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, provided that the variant Fc polypeptide comprises a set of L234A, L235A, G237A, D265K, E269S, Y296Q, S298K, and P329K mutations, as compared to SEQ ID NO: 19;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20, provided that the variant Fc polypeptide comprises a set of L234A, L235A, G237A, D265K, E269S, Y296Q, S298K, and P329K mutations, as compared to SEQ ID NO: 20;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21, provided that the variant Fc polypeptide comprises a set of L234A, L235A, G237A, D265K, E269S, Y296Q, S298K, and P329K mutations, as compared to SEQ ID NO: 21;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22, provided that the variant Fc polypeptide comprises a set of L234A, L235A, G237A, D265K, E269S, Y296Q, S298K, and P329K mutations, as compared to SEQ ID NO: 22;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23, provided that the variant Fc polypeptide comprises a set of L234A, L235A, G237A, D265K, E269S, Y296Q, S298K, and P329K mutations, as compared to SEQ ID NO: 23;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24, provided that the variant Fc polypeptide comprises a set of L234A, L235A, G237A, D265K, E269S, Y296Q, S298K, and P329K mutations, as compared to SEQ ID NO: 24; or an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25, provided that the variant Fc polypeptide comprises a set of L234A, L235A, G237A, D265K, E269S, Y296Q, S298K, and P329K mutations, as compared to SEQ ID NO: 25.

74. The polypeptide of any one of embodiments 67-73, wherein the variant Fc polypeptide comprises:
   an amino acid sequence of SEQ ID NO: 19;
   an amino acid sequence of SEQ ID NO: 21;
   an amino acid sequence of SEQ ID NO: 22;
   an amino acid sequence of SEQ ID NO: 23;
   an amino acid sequence of SEQ ID NO: 24; or
   an amino acid sequence of SEQ ID NO: 25.

75. The polypeptide of any one of embodiments 61-74, wherein the polypeptide further comprises a His-tag.

76. The polypeptide of embodiment 72, wherein the His-tag is conjugated to the C-terminus of the polypeptide.

77. The polypeptide of any one of embodiments 75-76, wherein the His-tag has the amino acid sequence of SEQ ID NO: 27, or 34.

78. A polypeptide having a formula from N-terminus to C-terminus selected from:

N1-P1; or

P1-N1, wherein,
   P1 comprises a polypeptide having protease activity;
   N1 comprises a nanobody; and
   optionally wherein the protease is a glycosylation-resistant protease.

79. The polypeptide of embodiment 78, wherein the polypeptide having protease activity is a polypeptide having IgG cleaving protease activity.

80. The polypeptide of embodiment 79, wherein the polypeptide having IgG cleaving protease activity comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 26, 28, 29, 31, 36, 37, 38, 39, 40, 41, 50, 51, 52, or 55.

81. The polypeptide of any one of embodiments 79-80, wherein the polypeptide having IgG cleaving protease activity comprises an amino acid sequence of SEQ ID NO: 26, 28, 29, 31, 36, 37, 38, 39, 40, 41, 50, 51, 52, or 55.

82. The polypeptide of any one of embodiments 78-81, wherein the polypeptide having protease activity is selected from IdeS, IdeSsuis, IdeE, IdeZ, IdeE2, IdeZ2, or IdeC protease, or a variant thereof.

83. The polypeptide of any one of embodiments 78-82, wherein the polypeptide having protease activity comprises a mutation at one, or more, glycosylation sites.

84. The polypeptide of any one of embodiments 78-83, wherein the polypeptide further comprises a His-tag.

85. The polypeptide of embodiment 84, wherein the His-tag is conjugated to the C-terminus of the polypeptide.

86. The polypeptide of any one of embodiments 84-85, wherein the His-tag has the amino acid sequence of SEQ ID NO: 27, or 34.

87. A polypeptide having a formula from N-terminus to C-terminus selected from:

N1-IdeS-variant Fc;

variant Fc-IdeS-N1;

IdeS-variant Fc-N1; or

N1-variant Fc-IdeS, wherein,
   N1 comprises a nanobody; and
   variant Fc is a variant Fc polypeptide.

88. The polypeptide of embodiment 87, wherein IdeS comprises an amino acid sequence having at least 50%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 26, 28, 29, 31, 36, 50, or 51.

89. The polypeptide of any one of embodiments 87-88, wherein IdeS comprises an amino acid sequence of SEQ ID NO: 26, 28, 29, 31, 36, 50, or 51.

90. The polypeptide of any one of embodiments 87-89, wherein the IdeS protease comprises a mutation at position 42, 47, 61, 62, 63, 274, 288, 289, 290, 336, 337, 338, or any combination thereof, as compared to SEQ ID NO: 36.

91. The polypeptide of any one of embodiments 87-90, wherein the IdeS protease comprises a mutation at position N61, as compared to SEQ ID NO: 36.

92. The polypeptide of any one of embodiments 87-90, wherein the IdeS protease comprises a mutation at position S290, as compared to SEQ ID NO: 36.

93. The polypeptide of any one of embodiments 87-90, wherein the IdeS protease comprises mutations at position N61 and S290, as compared to SEQ ID NO: 36.

94. The polypeptide of any one of embodiments 87-90, wherein the IdeS protease comprises mutations at positions N42, as compared to SEQ ID NO: 36.

95. The polypeptide of any one of embodiments 87-90, wherein the IdeS protease comprises mutations at positions N47, as compared to SEQ ID NO: 36.

96. The polypeptide of any one of embodiments 87-90, wherein the IdeS protease comprises mutations at positions N274, as compared to SEQ ID NO: 36.

97. The polypeptide of any one of embodiments 87-90, wherein the IdeS protease comprises mutations at positions N47 and N274, as compared to SEQ ID NO: 36.

98. The polypeptide of any one of embodiments 87-90, wherein the IdeS protease comprises a N61Q mutation, as compared to SEQ ID NO: 36.

99. The polypeptide of any one of embodiments 87-90, wherein the IdeS protease comprises a S290Q mutation, as compared to SEQ ID NO: 36.

100. The polypeptide of any one of embodiments 87-90, wherein the IdeS protease comprises N61Q and S290Q mutations, as compared to SEQ ID NO: 36.

101. The polypeptide of any one of embodiments 87-100, wherein the IdeS protease is resistant to N-glycosylation at one or more N-glycosylation motifs, as compared to SEQ ID NO: 36.

102. The polypeptide of embodiment 87, wherein the variant Fc molecule is a variant Fc polypeptide.

103. The polypeptide of embodiment 102, wherein the variant Fc polypeptide comprises an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 1, provided that the variant Fc polypeptide comprises a mutation set selected from:
- L234A, L235A, G237A, Y296Q, and P329K;
- L234A, L235A, G237A, Y296Q, S298K, and P329K;
- L234A, L235A, G237A, D265K, E269S, Y296Q, and P329K; or
- L234A, L235A, G237A, D265K, E269S, Y296Q, S298K, and P329K.

104. The polypeptide of any one of embodiments 102-103, wherein the variant Fc polypeptide comprises mutations corresponding to L234A, L235A, G237A, Y296Q, and P329K according to SEQ ID NO: 1.

105. The polypeptide of any one of embodiments 102-103, wherein the variant Fc polypeptide comprises mutations corresponding to L234A, L235A, G237A, Y296Q, S298K, and P329K according to SEQ ID NO: 1.

106. The polypeptide of any one of embodiments 102-103, wherein the variant Fc polypeptide comprises mutations corresponding to L234A, L235A, G237A, D265K, E269S, Y296Q, and P329K according to SEQ ID NO: 1.

107. The polypeptide of any one of embodiments 102-103, wherein the variant Fc polypeptide comprises mutations corresponding to L234A, L235A, G237A, D265K, E269S, Y296Q, S298K, and P329K according to SEQ ID NO: 1.

108. The polypeptide of any one of embodiments 102-107, wherein the variant Fc polypeptide comprises an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, 20, 21, 22, 23, 24, or 25, provided that the variant Fc polypeptide comprises a set of mutations selected from:
- L234A, L235A, G237A, Y296Q, and P329K;
- L234A, L235A, G237A, Y296Q, S298K, and P329K;
- L234A, L235A, G237A, D265K, E269S, Y296Q, and P329K; or
- L234A, L235A, G237A, D265K, E269S, Y296Q, S298K, and P329K;

as compared to SEQ ID NO: 19, 20, 21, 22, 23, 24, or 25.

109. The polypeptide of embodiment 108, wherein the variant IgG Fc comprises:
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, provided that the variant Fc polypeptide comprises a set of L234A, L235A, G237A, Y296Q, and P329K mutations, as compared to SEQ ID NO: 19;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20, provided that the variant Fc polypeptide comprises a set of L234A, L235A, G237A, Y296Q, and P329K mutations, as compared to SEQ ID NO: 20;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21, provided that the variant Fc polypeptide comprises a set of L234A, L235A, G237A, Y296Q, and P329K mutations, as compared to SEQ ID NO: 21;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22, provided that the variant Fc polypeptide comprises a set of L234A, L235A, G237A, Y296Q, and P329K mutations, as compared to SEQ ID NO: 22;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23, provided that the variant Fc polypeptide comprises a set of L234A, L235A, G237A, Y296Q, and P329K mutations, as compared to SEQ ID NO: 23;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24, provided that the variant Fc polypeptide comprises a set of L234A, L235A, G237A, Y296Q, and P329K mutations, as compared to SEQ ID NO: 24;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25, provided that the variant Fc polypeptide comprises a set of L234A, L235A, G237A, Y296Q, and P329K mutations, as compared to SEQ ID NO: 25;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, provided that the variant Fc polypeptide comprises a set of L234A, L235A, G237A, Y296Q, S298K, and P329K mutations, as compared to SEQ ID NO: 19;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20, provided that the variant Fc polypeptide comprises a set of L234A, L235A, G237A, Y296Q, S298K, and P329K mutations, as compared to SEQ ID NO: 20;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21, provided that the variant Fc polypeptide comprises a set of L234A, L235A, G237A, Y296Q, S298K, and P329K mutations, as compared to SEQ ID NO: 21;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22, provided that the variant Fc polypeptide comprises a set of L234A, L235A, G237A, Y296Q, S298K, and P329K mutations, as compared to SEQ ID NO: 22;
- an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23, provided that the variant Fc polypeptide comprises a set of L234A, L235A, G237A, Y296Q, S298K, and P329K mutations, as compared to SEQ ID NO: 23;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24, provided that the variant Fc polypeptide comprises a set of L234A, L235A, G237A, Y296Q, S298K, and P329K mutations, as compared to SEQ ID NO: 24;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25, provided that the variant Fc polypeptide comprises a set of L234A, L235A, G237A, Y296Q, S298K, and P329K mutations, as compared to SEQ ID NO: 25;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, provided that the variant Fc polypeptide comprises a set of L234A, L235A, G237A, D265K, E269S, Y296Q, and P329K mutations, as compared to SEQ ID NO: 19;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20, provided that the variant Fc polypeptide comprises a set of L234A, L235A, G237A, D265K, E269S, Y296Q, and P329K mutations, as compared to SEQ ID NO: 20;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21, provided that the variant Fc polypeptide comprises a set of L234A, L235A, G237A, D265K, E269S, Y296Q, and P329K mutations, as compared to SEQ ID NO: 21;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22, provided that the variant Fc polypeptide comprises a set of L234A, L235A, G237A, D265K, E269S, Y296Q, and P329K mutations, as compared to SEQ ID NO: 22;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23, provided that the variant Fc polypeptide comprises a set of L234A, L235A, G237A, D265K, E269S, Y296Q, and P329K mutations, as compared to SEQ ID NO: 23;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24, provided that the variant Fc polypeptide comprises a set of L234A, L235A, G237A, D265K, E269S, Y296Q, and P329K mutations, as compared to SEQ ID NO: 24;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25, provided that the variant Fc polypeptide comprises a set of L234A, L235A, G237A, D265K, E269S, Y296Q, and P329K mutations, as compared to SEQ ID NO: 25;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19, provided that the variant Fc polypeptide comprises a set of L234A, L235A, G237A, D265K, E269S, Y296Q, S298K, and P329K mutations, as compared to SEQ ID NO: 19;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20, provided that the variant Fc polypeptide comprises a set of L234A, L235A, G237A, D265K, E269S, Y296Q, S298K, and P329K mutations, as compared to SEQ ID NO: 20;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 21, provided that the variant Fc polypeptide comprises a set of L234A, L235A, G237A, D265K, E269S, Y296Q, S298K, and P329K mutations, as compared to SEQ ID NO: 21;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 22, provided that the variant Fc polypeptide comprises a set of L234A, L235A, G237A, D265K, E269S, Y296Q, S298K, and P329K mutations, as compared to SEQ ID NO: 22;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 23, provided that the variant Fc polypeptide comprises a set of L234A, L235A, G237A, D265K, E269S, Y296Q, S298K, and P329K mutations, as compared to SEQ ID NO: 23;

an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 24, provided that the variant Fc polypeptide comprises a set of L234A, L235A, G237A, D265K, E269S, Y296Q, S298K, and P329K mutations, as compared to SEQ ID NO: 24; or an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 25, provided that the variant Fc polypeptide comprises a set of L234A, L235A, G237A, D265K, E269S, Y296Q, S298K, and P329K mutations, as compared to SEQ ID NO: 25.

110. The polypeptide of any one of embodiments 102-109, wherein the variant Fc polypeptide comprises:
- an amino acid sequence of SEQ ID NO: 19;
- an amino acid sequence of SEQ ID NO: 21;
- an amino acid sequence of SEQ ID NO: 22;
- an amino acid sequence of SEQ ID NO: 23;
- an amino acid sequence of SEQ ID NO: 24; or
- an amino acid sequence of SEQ ID NO: 25.

111. The polypeptide of any one of embodiments 87-110, wherein the polypeptide further comprises a His-tag.

112. The polypeptide of embodiment 111, wherein the His-tag is conjugated to the C-terminus of the polypeptide.

113. The polypeptide of any one of embodiments 111-112, wherein the His-tag has the amino acid sequence of SEQ ID NO: 27, or 34.

114. The polypeptide of any one of embodiments 1-113, wherein the polypeptide has an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to any one of sequence of VRT-1, VRT-2, VRT-3, VRT-4, VRT-5, VRT-6, VRT-7, VRT-8, VRT-9, VRT-10, VRT-11, VRT-12, VRT-13, VRT-14, VRT-15, VRT-16, VRT-17, VRT-18, VRT-19, VRT-20, VRT-21, VRT-22, VRT-23, VRT-24, VRT-25, VRT-26, VRT-27, VRT-28, VRT-29, or VRT-30, wherein the polypeptide has protease activity and the Fc polypeptide is protease resistant.

115. The polypeptide of any of embodiments 1-114, wherein the polypeptide has an amino acid sequence of any one of VRT-1, VRT-2, VRT-3, VRT-4, VRT-5, VRT-6, VRT-7, VRT-8, VRT-9, VRT-10, VRT-11, VRT-12, VRT-13, VRT-14, VRT-15, VRT-16, VRT-17, VRT-18, VRT-19, VRT-20, VRT-21, VRT-22, VRT-23, VRT-24, VRT-25, VRT-26, VRT-27, VRT-28, VRT-29, or VRT-30.

116. A method of treating a disease or disorder in a subject, the method comprising administering the polypeptide of any of embodiments 1-115 to the subject to treat the disease or disorder.

117. The method of embodiment 116, wherein the disease or disorder is selected from Addison's disease, Anti-GBM glomerulonephritis, anti-neutrophil cytoplasmic antibody-associated vasculitides, ANCA associated vasculitis, granulomatous polyangiitis (Wegener granulomatosis), eosinophilic granulomatosis with polyangiitis (Churg-Strauss syndrome), microscopic polyangiitis, anti-NMDAR encephalitis, anti-phospholipid antibody syndrome (APS) and catastrophic APS, autoimmune bullous skin diseases, pemphigus, *Pemphigus foliaceus* (PF), fogo selvage (FS), *Pemphigus vulgaris* (PV), autoimmune hemolytic anemia (AIHA), autoimmune hepatitis (AIH), autoimmune neutropenia (AIN), bullous pemphigoid (BP), Celiac's disease, chronic urticaria, complete congenital heart block (CCHB), diabetes type 1A (TIDM), epidermolysis bullosa acquisita (EBA), essential mixed cryoglobulinemia, Goodpasture's syndrome, anti-glomerular basement membrane disease, Graves' disease, Goitre, hyperthyroidism, infiltrative exophthalmos, infiltrative dermopathy, Guillain-Barre syndrome (GBS), acute inflammatory demyelinating polyneuropathy (AIDP), acute motor axonal neuropathy (AMAN), hemophilia, acquired FVII deficiency, idiopathic thrombocytopenia purpura (ITP), Lambert-Eaton myasthenic syndrome (LEMS), mixed connective tissue disease (MCTD), multiple myeloma, myasthenia gravis, myasthenic crisis, myocarditis, dilated cardiomyopathy (DCM), congestive cardiomyopathy, neuromyelitis optica (NMO), primary biliary cirrhosis (PBC), primary progressive multiple sclerosis (PPMS), relapsing-rheumatic multiple sclerosis, acute exacerbation of multiple sclerosis, rheumatic heart disease (RHD), rheumatoid arthritis (RA), serum-sickness, immune complex hypersensitivity (type III), Sjögren's syndrome (SS), lupus nephritis, systemic lupus erythematosus (SLE), cutaneous lupus (CLE), transplant rejection, thrombotic thrombocytopeniarpura (TTP), idiopathic inflammatory myopathies, polymyositis, dermatomyositis, inclusion body myositis, uveitis, scleritis, ankylosing spondylitis, axial spondyloarthritis, reactive arthritis, psoriatic arthritis, IBD-associated arthritis, antiphospholipid syndrome, systemic sclerosis, giant cell arteritis, polymyalgia rheumatic, Takayasu's arteritis, anti-neutrophil cytoplasmic antibody associated vasculitis, Henoch-Schonlein purpura, polyarteritis nodosa, Cogan's syndrome, Buerger's disease, Susan's disease, immune complex vasculitis, primary angiitis of the central nervous system (CNS), Behcet's disease, relapsing polychondritis, juvenile idiopathic arthritis, juvenile dermatomyositis, autoimmune brain disease, sarcoidosis, neurosarcoidosis, IgG4-related diseases, autoimmune complications of immune checkpoint inhibitors (IRAEs), adult onset Still's disease, warm antibody hemolytic anemia (wAIHA), immune thrombocytopenia, immune thrombotic thrombocytopenia, thrombic thrombocytopenia, pernicious anemia, aplastic anemia, Evan's syndrome, autoimmune neutropenia, acquired von Willibrand syndrome, recurring fetal loss, Rh mismatch, ulcerative colitis, autoimmune hepatitis, autoimmune pancreatitis, eosinophilic esophagitis/gastritis, primary sclerosing cholangitis, primary biliary sclerosis, glomerulonephritis, glomerular basement membrane disease, scleritis/episcleritis, uveitis, conjunctivitis, keratitis, type I diabetes mellitus, Hashimoto's thyroiditis, polyglandular autoimmune endocrine syndromes, atopic dermatitis, dermatitis herpetiformis, *Pemphigus foliaceus*, fogo selvagem, cutaneous lupus erythematosus, linear IgA disease, Lichen planus, transplantation, antibody-mediated rejection, alloantibody hypersensitization, xenoantibody mediated rejection, solid organ rejection, graft vs. host disease (GVHD), multiple sclerosis, neuromyelitis optica, amyotrophic lateral sclerosis, Parkinson's disease, autoimmune encephalitis, CNS vasculitis, chronic idiopathic demyletinating polyneuropathy, transverse myelitis, optic neuritis, anti-myelin oligodendrocyte glycoprotein (MOG) disease, chronic meningitis, rheumatic heart disease, infectious disease, vaccination, antibody dependent enhancement, antibody to therapeutic biologic agents (cytokines, monoclonal antibodies, enzymes, coagulation factors), allergic asthma, eosinophilic pneumonia, nonspecific interstitial pneumonia, rheumatoid arthritis-associated interstitial lung disease (RA-ILD), sarcoidosis, hypersensitive pneumonitis, allergic bronchopulmonary mycosis, chronic rhinosinusitis with nasal polyps, or any combination thereof.

118. A method of treating a transplant subject comprising administering a therapeutically effective amount of the polypeptide of any of embodiments 1-115 to the subject, thereby treating the transplant (recipient) subject.

119. A method of improving a gene-therapy in subject comprising administering a therapeutically effective amount of the polypeptide of any of embodiments 1-115 to the subject, thereby improving the gene-therapy in the subject.

120. A method of treating a subject having, or at risk, or elevated risk, for having, an IgG mediated disease or disorder, comprising administering a therapeutically effective amount of the polypeptide of any embodiments 1-115, thereby treating the subject.

121. A nucleic acid encoding the polypeptide of any of embodiments 1-115.

122. A vector comprising the nucleic acid of embodiment 121.

123. A cell comprising the nucleic acid of embodiment 121 or the vector of embodiment 122.

124. A method of making the polypeptide comprising culturing a cell of embodiment 123 to make the therapeutic compound.

125. A method of making a nucleic acid sequence encoding the polypeptide of any one of embodiments 1-115, comprising
   a) providing a vector comprising sequence encoding a polypeptide having protease activity and inserting into the vector sequence encoding a variant Fc molecule to form an amino acid sequence encoding the polypeptide; or
   b) providing a vector comprising sequence encoding a variant Fc molecule and inserting into the vector sequence encoding a polypeptide having protease activity to form an amino acid sequence encoding the polypeptide, thereby making an amino acid sequence encoding the polypeptide.

126. A variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 56, provided that the variant Fc polypeptide comprises a set of mutations selected from:
   L234A, L235A, G237A, Y296Q, and P329K;
   L234A, L235A, G237A, Y296Q, S298K, and P329K;
   L234A, L235A, G237A, D265K, E269S, Y296Q, and P329K; or
   L234A, L235A, G237A, D265K, E269S, Y296Q, S298K, and P329K;
   as compared to SEQ ID NO: 1.

127. The variant Fc polypeptide of embodiment 126, wherein the variant Fc polypeptide comprises a set of L234A, L235A, G237A, Y296Q, and P329K mutations, as compared to SEQ ID NO: 1.

128. The variant Fc polypeptide of embodiment 126, wherein the variant Fc polypeptide comprises a set of L234A, L235A, G237A, Y296Q, S298K, and P329K mutations, as compared to SEQ ID NO: 1.

129. The variant Fc polypeptide of embodiment 126, wherein the variant Fc polypeptide comprises a set of L234A, L235A, G237A, D265K, E269S, Y296Q, and P329K mutations, as compared to SEQ ID NO: 1.

130. The variant Fc polypeptide of embodiment 126, wherein the variant Fc polypeptide comprises a set of L234A, L235A, G237A, D265K, E269S, Y296Q, S298K, and P329K mutations, as compared to SEQ ID NO: 1.

131. The variant Fc polypeptide of embodiment 126, wherein the variant Fc polypeptides comprises an amino acid sequence having at least 95% identity to an amino acid sequence comprising the amino acid sequence of SEQ ID NO: 56 provided that the polypeptide comprises an alanine (A) residue at position 234, an alanine (A) residue at position 235, an alanine (A) residue at position 237, a glutamine (Q) residue at position 296, and a lysine (K) residue at position 329, wherein the positions are according to EU numbering.

132. The variant Fc polypeptide of embodiment 131, wherein the variant Fc polypeptide has at least 95% identity to an amino acid sequence comprising the amino acid sequence of SEQ ID NO: 1 provided that the polypeptide comprises an alanine (A) residue at position 234, an alanine (A) residue at position 235, an alanine (A) residue at position 237, a glutamine (Q) residue at position 296, and a lysine (K) residue at position 329, wherein the positions are according to EU numbering.

133. The variant Fc polypeptide of any one of embodiments 126-132, wherein the variant Fc polypeptide is resistant to proteolytic cleavage and/or binding by a protease.

134. The variant Fc polypeptide of any one of embodiments 126-133, wherein the variant Fc polypeptide comprises an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to any one of SEQ ID NO: 23, 19, 20, 21, 22, 23, 24, 25, 42, 43, 44, 45, 46, 47, 48, or 49.

135. The variant Fc polypeptide of embodiment 134, wherein the variant Fc polypeptide comprises an amino acid sequence of any one of SEQ ID NO: 23, 19, 20, 21, 22, 23, 24, 25, 42, 43, 44, 45, 46, 47, 48, or 49.

136. The variant Fc polypeptide of any one of embodiments 126-135, wherein the variant Fc polypeptide forms a dimer, such as a homodimer, or a heterodimer.

137. The variant Fc polypeptide of any one of embodiments 126-136, wherein the variant Fc polypeptide is linked or fused to a protease.

138. The variant Fc polypeptide of embodiment 137, wherein the variant Fc polypeptide is linked to the protease via a peptide linker.

139. The variant Fc polypeptide of embodiment 138, wherein the protease is selected from IdeS, IdeSsuis, IdeE, IdeZ, IdeE2, IdeZ2, or IdeC protease, or a variant thereof.

140. A variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to any one of SEQ ID NO: 23, 19, 20, 21, 22, 23, 24, 25, 42, 43, 44, 45, 46, 47, 48, or 49.

141. The variant Fc polypeptide of embodiment 140, wherein the variant Fc polypeptide comprises a set of mutations selected from:
   L234A, L235A, G237A, Y296Q, and P329K;
   L234A, L235A, G237A, Y296Q, S298K, and P329K;
   L234A, L235A, G237A, D265K, E269S, Y296Q, and P329K; or
   L234A, L235A, G237A, D265K, E269S, Y296Q, S298K, and P329K;
   as compared to SEQ ID NO: 1.

142. The variant Fc polypeptide of embodiment 141, wherein the variant Fc polypeptides comprises an amino acid sequence having at least 95% identity to an amino acid sequence comprising the amino acid sequence of SEQ ID NO: 56 provided that the polypeptide comprises an alanine (A) residue at position 234, an alanine (A) residue at position 235, an alanine (A) residue at position 237, a glutamine (Q) residue at position 296, and a lysine (K) residue at position 329, wherein the positions are according to EU numbering.

143. The variant Fc polypeptide of embodiment 142, wherein the variant Fc polypeptide has at least 95% identity to an amino acid sequence comprising the amino acid sequence of SEQ ID NO: 1 provided that the polypeptide comprises an alanine (A) residue at position 234, an alanine (A) residue at position 235, an alanine (A) residue at position 237, a glutamine (Q) residue at position 296, and a lysine (K) residue at position 329, wherein the positions are according to EU numbering.

144. The variant Fc polypeptide of any one of embodiments 140-143, wherein the variant Fc polypeptide is resistant to proteolytic cleavage and/or binding by a protease.

145. The variant Fc polypeptide of embodiment 144, wherein the variant Fc polypeptide comprises an amino acid sequence of any one of SEQ ID NO: 23, 19, 20, 21, 22, 23, 24, 25, 42, 43, 44, 45, 46, 47, 48, or 49.

146. The variant Fc polypeptide of any one of embodiments 140-145, wherein the variant Fc polypeptide forms a dimer, such as a homodimer, or a heterodimer.

147. The variant Fc polypeptide of any one of embodiments 140-146, wherein the variant Fc polypeptide is linked or fused to a protease.

148. The variant Fc polypeptide of embodiment 147, wherein the variant Fc polypeptide is linked to the protease via a peptide linker.

149. The variant Fc polypeptide of embodiment 148, wherein the protease is selected from IdeS, IdeSsuis, IdeE, IdeZ, IdeE2, IdeZ2, or IdeC protease, or a variant thereof.

150. A molecule comprising:
   a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 56, provided that the variant Fc polypeptide comprises a set of mutations selected from:
      L234A, L235A, G237A, Y296Q, and P329K;
      L234A, L235A, G237A, Y296Q, S298K, and P329K;
      L234A, L235A, G237A, D265K, E269S, Y296Q, and P329K; or
      L234A, L235A, G237A, D265K, E269S, Y296Q, S298K, and P329K;
   as compared to SEQ ID NO: 1; and
   a protease.

151. The molecule of embodiment 150, wherein the variant Fc polypeptides comprises an amino acid sequence having at least 95% identity to an amino acid sequence comprising the amino acid sequence of SEQ ID NO: 56 provided that the polypeptide comprises an alanine (A) residue at position 234, an alanine (A) residue at position 235, an alanine (A) residue at position 237, a glutamine (Q) residue at position 296, and a lysine (K) residue at position 329, wherein the positions are according to EU numbering.

152. The molecule of embodiment 151, wherein the variant Fc polypeptide has at least 95% identity to an amino acid sequence comprising the amino acid sequence of SEQ ID NO: 1 provided that the polypeptide comprises an alanine (A) residue at position 234, an alanine (A) residue at position 235, an alanine (A) residue at position 237, a glutamine (Q) residue at position 296, and a lysine (K) residue at position 329, wherein the positions are according to EU numbering.

153. The molecule of any one of embodiments 150-152, wherein the variant Fc polypeptide is resistant to proteolytic cleavage and/or binding by a protease.

154. The molecule of any one of embodiments 150-153, wherein the variant Fc polypeptide comprises an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to any one of SEQ ID NO: 23, 19, 20, 21, 22, 23, 24, 25, 42, 43, 44, 45, 46, 47, 48, or 49.

155. The molecule of embodiment 154, wherein the variant Fc polypeptide comprises an amino acid sequence of any one of SEQ ID NO: 23, 19, 20, 21, 22, 23, 24, 25, 42, 43, 44, 45, 46, 47, 48, or 49.

156. The molecule of any one of embodiments 150-155, wherein the variant Fc polypeptide forms a dimer, such as a homodimer, or a heterodimer.

157. The molecule of embodiment 156, wherein the variant Fc polypeptide is linked or fused to the protease via a peptide linker.

158. The molecule of any one of embodiments 150-157, wherein the protease is selected from IdeS, IdeSsuis, IdeE, IdeZ, IdeE2, IdeZ2, or IdeC protease, or a variant thereof.

159. A molecule comprising:
   a variant Fc polypeptide comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identity to any one of SEQ ID NO: 23, 19, 20, 21, 22, 23, 24, 25, 42, 43, 44, 45, 46, 47, 48, or 49; and
   a protease.

160. The molecule of embodiment 159, wherein the variant Fc polypeptide comprises a set of mutations selected from:
   L234A, L235A, G237A, Y296Q, and P329K;
   L234A, L235A, G237A, Y296Q, S298K, and P329K;
   L234A, L235A, G237A, D265K, E269S, Y296Q, and P329K; or
   L234A, L235A, G237A, D265K, E269S, Y296Q, S298K, and P329K;
   as compared to SEQ ID NO: 1.

161. The molecule of embodiment 160, wherein the variant Fc polypeptides comprises an amino acid sequence having at least 95% identity to an amino acid sequence comprising the amino acid sequence of SEQ ID NO: 56 provided that the polypeptide comprises an alanine (A) residue at position 234, an alanine (A) residue at position 235, an alanine (A) residue at position 237, a glutamine (Q) residue at position 296, and a lysine (K) residue at position 329, wherein the positions are according to EU numbering.

162. The molecule of embodiment 161, wherein the variant Fc polypeptide has at least 95% identity to an amino acid sequence comprising the amino acid sequence of SEQ ID NO: 1 provided that the polypeptide comprises an alanine (A) residue at position 234, an alanine (A) residue at position 235, an alanine (A) residue at position 237, a glutamine (Q) residue at position 296, and a lysine (K) residue at position 329, wherein the positions are according to EU numbering.

163. The molecule of any one of embodiments 159-162, wherein the variant Fc polypeptide is resistant to proteolytic cleavage and/or binding by a protease.

164. The molecule of embodiment 163, wherein the variant Fc polypeptide comprises an amino acid sequence of any one of SEQ ID NO: 23, 19, 20, 21, 22, 23, 24, 25, 42, 43, 44, 45, 46, 47, 48, or 49.

165. The molecule of any one of embodiments 159-164, wherein the variant Fc polypeptide forms a dimer, such as a homodimer, or a heterodimer.

166. The molecule of any one of embodiments 159-165, wherein the variant Fc polypeptide is linked to the protease via a peptide linker.

167. The molecule of any one of embodiments 159-166, wherein the protease is selected from IdeS, IdeSsuis, IdeE, IdeZ, IdeE2, IdeZ2, or IdeC protease, or a variant thereof.

168. A pharmaceutical composition comprising the variant Fc polypeptide of any of embodiments 126-149, or the molecule of any one of embodiments 150-167.

169. A method of treating a disease or disorder in a subject, the method comprising administering the variant Fc polypeptide of any of embodiments 126-149, or the molecule of any one of embodiments 150-167 to the subject to treat the disease or disorder.

170. The method of embodiment 169, wherein the disease or disorder is selected from IgG mediated disease or disorder, Addison's disease, Anti-GBM glomerulonephritis, anti-neutrophil cytoplasmic antibody-associated vasculitides, ANCA associated vasculitis, granulomatous polyangiitis (Wegener granulomatosis), cosinophilic granulomatosis with polyangiitis (Churg-Strauss syndrome), microscopic polyangiitis, anti-NMDAR encephalitis, anti-phospholipid antibody syndrome (APS) and catastrophic APS, autoimmune bullous skin diseases, pemphigus, Pemphigus foliaceus (PF), fogo selvage (FS), Pemphigus vulgaris (PV), autoimmune hemolytic anemia (AIHA), autoimmune hepatitis (AIH), autoimmune neutropenia (AIN), bullous pemphigoid (BP), Celiac's disease, chronic urticaria, complete congenital heart block (CCHB), diabetes type 1A (T1DM), epidermolysis bullosa acquisita (EBA), essential mixed cryoglobulinemia, Goodpasture's syndrome, anti-glomerular basement membrane disease, Graves' disease, Goitre, hyperthyroidism, infiltrative exophthalmos, infiltrative dermopathy, Guillain-Barre syndrome (GBS), acute inflammatory demyelinating polyneuropathy (AIDP), acute motor axonal neuropathy (AMAN), hemophilia, acquired FVII deficiency, idiopathic thrombocytopenia purpura (ITP), Lambert-Eaton myasthenic syndrome (LEMS), mixed connective tissue disease (MCTD), multiple myeloma, myasthenia gravis, myasthenic crisis, myocarditis, dilated cardiomyopathy (DCM), congestive cardiomyopathy, neuromyelitis optica (NMO), primary biliary cirrhosis (PBC), primary progressive multiple sclerosis (PPMS), relapsing-rheumatic multiple sclerosis, acute exacerbation of multiple sclerosis, rheumatic heart disease (RHD), rheumatoid arthritis (RA), serum-sickness, immune complex hypersensitivity (type III), Sjögren's syndrome (SS), lupus nephritis, systemic lupus erythematosus (SLE), cutaneous lupus (CLE), transplant rejection, thrombotic thrombocytopenia purpura (TTP), idiopathic inflammatory myopathies, polymyositis, dermatomyositis, inclusion body myositis, uveitis, scleritis, ankylosing spondylitis, axial spondyloarthritis, reactive arthritis, psoriatic arthritis, IBD-associated arthritis, antiphospholipid syndrome, systemic sclerosis, giant cell arteritis, polymyalgia rheumatic, Takayasu's arteritis, anti-neutrophil cytoplasmic antibody associated vasculitis, Henoch-Schonlein purpura, polyarteritis nodosa, Cogan's syndrome, Buerger's disease, Susan's disease, immune complex vasculitis, primary angiitis of the central nervous system (CNS), Behcet's disease, relapsing polychondritis, juvenile idiopathic arthritis, juvenile dermatomyositis, autoimmune brain disease, sarcoidosis, neurosarcoidosis, IgG4-related diseases, autoimmune complications of immune checkpoint inhibitors (IRAEs), adult onset Still's disease, warm antibody hemolytic anemia (wAIHA), immune thrombocytopenia, immune thrombotic thrombocytopenia, thrombic thrombocytopenia, pernicious anemia, aplastic anemia, Evan's syndrome, autoimmune neutropenia, acquired von Willibrand syndrome, recurring fetal loss, Rh mismatch, ulcerative colitis, autoimmune hepatitis, autoimmune pancreatitis, cosinophilic esophagitis/gastritis, primary sclerosing cholangitis, primary biliary sclerosis, glomerulonephritis, glomerular basement membrane disease, scleritis/episcleritis, uveitis, conjunctivitis, keratitis, type I diabetes mellitus, Hashimoto's thyroiditis, polyglandular autoimmune endocrine syndromes, atopic dermatitis, dermatitis herpetiformis, Pemphigus foliaceus, fogo selvagem, cutaneous lupus erythematosus, linear IgA disease, Lichen planus, transplantation, antibody-mediated rejection, alloantibody hypersensitization, xenoantibody mediated rejection, solid organ rejection, graft vs. host disease (GVHD), multiple sclerosis, neuromyelitis optica, amyotrophic lateral sclerosis, Parkinson's disease, autoimmune encephalitis, CNS vasculitis, chronic idiopathic demyletinating polyneuropathy, transverse myelitis, optic neuritis, anti-myelin oligodendrocyte glycoprotein (MOG) disease, chronic meningitis, rheumatic heart disease, infectious disease, vaccination, antibody dependent enhancement, antibody to therapeutic biologic agents (cytokines, monoclonal antibodies, enzymes, coagulation factors), allergic asthma, cosinophilic pneumonia, nonspecific interstitial pneumonia, rheumatoid arthritis-associated interstitial lung disease (RA-ILD), sarcoidosis, hypersensitive pneumonitis, allergic bronchopulmonary mycosis, chronic rhinosinusitis with nasal polyps, or any combination thereof.

171. A method of treating a transplant subject comprising administering a therapeutically effective amount of the variant Fc polypeptide of any of embodiments 126-149, or the molecule of any one of embodiments 150-167 to the subject, thereby treating the transplant (recipient) subject.

172. A method of improving a gene-therapy in subject comprising administering a therapeutically effective amount of the variant Fc polypeptide of any of embodiments 126-149, or the molecule of any one of embodiments 150-167 to the subject, thereby improving the gene-therapy in the subject.

173. A nucleic acid encoding the variant Fc polypeptide of any of embodiments 126-149, or the molecule of any one of embodiments 150-167.

174. A vector comprising the nucleic acid of embodiment 173.

175. A cell comprising the nucleic acid of embodiment 173 or the vector of embodiment 174.

EXAMPLES

Example 1: Ides-Fc Polypeptides Exhibit High Yield in a Mammalian Expression System IdeS-Fc polypeptides provided herein were transiently expressed in Expi293 cells. Volumes of 2-5 ul of the supernatants were loaded onto SDS-PAGE or CE-SDS gels to visualize the bands of target proteins. All fusion formats had yields in excess of 100 mg/L. Homo-dimeric formats, including IdeS-Fc, Fc-IdeS, VHH(nanobody)-IdeS-Fc, and Fc-IdeS-VHH(nanobody), had approximately 500 mg/L yield. Knob-in-hole Fc formats produced mixture of correct paired and mis-paired species.

Example 2: Ides-Fc Polypeptides from Mammalian Expression were Catalytically Active Against Human IgG1

IdeS-Fc polypeptides provided herein were transiently expressed in Expi293 cells. Supernatants were incubated with a substrate human IgG1 kappa monoclonal antibody. Samples were loaded onto an SDS-PAGE gel to assess whether IgG1 was cleaved. All fusion formats, except the heavily glycosylated VRT-20, were catalytically active. IdeS with glycosylation knock out mutation at N61 remained active. VRT-20 was engineered to have 9 additional glycosylation sites comparing to wild type IdeS. Thus, the glycan shield blocked its activity.

Example 3: Ides-Fc Polypeptides Exhibit Aggregation in Low pH Elution from ProA Resin Columns Supernatants of Ides-Fc polypeptides from Expi293 expression were loaded onto protein A resin (ProA). Resin was eluted with low pH buffer at pH 2.8-3.3. ProA elution was neutralized with 1M Tris pH 8. Neutralized samples were spun down and the supernatant was loaded onto a 24 mL Superdex 75 size exclusion column. IdeS-Fc polypeptides precipitated heavily during low pH elution from protein A column. The protein A eluates were mainly aggregates on size exclusion column.

In another experiment, 5 mL of supernatants of Ides-Fc polypeptides from Expi293 expression were loaded onto protein A column. Column was eluted with low pH buffer at pH of 2.8-3.3. ProA elution was neutralized with 1M Tris pH 8. Precipitates were spun down and pellets were resuspended for SDS-PAGE. Neutralized samples were run on a SDS-PAGE gel. Inter-molecule disulfide bonds, were observed in the protein A elution fractions. The resuspended precipitates had primarily inter-molecule disulfide linked species.

Example 4: Addition of Arg and 2-MEA to the Elution Buffer Prevents Precipitation During ProA Purification Supernatants of Ides-Fc polypeptides from Expi293 expression were loaded onto protein A resin (ProA). Resin was eluted with low pH buffer at pH 2.8-3.3, as well as with and without arginine and 2-mercapto ethanolamine. ProA elution was neutralized with 1M Tris pH 8. Neutralized samples were spun down and the supernatant was loaded onto a 24 mL Superdex 75 size exclusion column. No precipitation of IdeS-Fc polypeptides was observed when arginine and 2-mercapto ethanolamine were included in low pH protein A elution buffer. Eluates arginine and 2-mercapto ethanolamine produced more monomeric species on size exclusion column than the elutes with only low pH buffer.

Example 5: SEC Purified Ides-Fc Polypeptides with Optimized Purification Process have Similar Activity to IdeS from E. coli Purified Ides-Fc polypeptides were subjected to Protein A elution and two step purified. Next, samples were incubated with substrate human monoclonal IgG1 at 1:100 Fc fusion: IgG molar ratio, for 4 hours at 37°C. IdeS purified from E. coli was assessed side by side, using 1:100 and 1:50 IdeS: IgG molar ratio. Digestion samples were loaded onto a CE-SDS gel to separate the bands of intact IgG (substrate), single cut IgG (intermediate product), and F(ab')2 (final product). Intensity of the target bands were used to visualize the data shown in FIG. 1. Two step purified IdeS-Fc polypeptides displayed similar activity to IdeS alone produced from E. coli.

Example 6: Low pH Destabilization of IdeS and IdeS-Fc Polypeptides

Ni-NTA one step purified IdeS and Ides-Fc polypeptides were incubated with different buffers, covering pH range 2.8 to 8. Thermostability and turbidity were measured at temperatures ranging from 25° C. to 90° C. At pH 2.8 to pH 4.5, no phase transition from folded to unfolded was observed on IdeS and IdeS Fc fusion protein. This indicates the polypeptides were destabilized by low pH. At pH above 6, clear phase transition from folded to unfolded was observed on IdeS and IdeS Fc fusion protein, with Tm around 50-55°C. This indicates the polypeptides were stable between pH 6 and pH 8.

Example 7: Screening of Excipients Identified Chemicals that Increase Ides-Fc Polypeptide Thermostability Two step purified Ides-Fc polypeptide VRT-5 was incubated with chemicals from two 96 well screening kits (HR2-072 and HR2-413 from Hampton Research). Thermostability and turbidity of each condition were measured at temperatures ranging from 25° C. to 90°C. As shown in the tables below, certain chemicals and buffers were identified to increase thermostability (Tm and Tagg). VRT-5 was more stable at neutral and basic pH in pH range 4.5 to 9. VRT-5 was more stable at higher sodium chloride concentration in range of 0.05 to 1M. Top 3 chemicals that increased Tm were D-sorbitol, Sucrose, and sodium sulfate. Succinic acid, sodium malonate, DL-malic acid also increased Tm at pH 7.0. Combination of D-sorbitol, Sucrose, and sodium sulfate in one buffer produced synergistic increase of thermostability.

| Conditions | Tm (° C.) | Tagg (° C.) |
|---|---|---|
| 0.05M Sodium acetate trihydrate pH 4.5, 1M Sodium chloride | 34.98 | 65.25 |
| 0.05M Sodium citrate tribasic dihydrate pH 5.0, 1M Sodium chloride | 50.38 | 81.01 |
| 0.05M Succinic acid pH 5.5, 1M Sodium chloride | 52.83 | 82.31 |
| 0.05M MES monohydrate pH 6.0, 1M Sodium chloride | 49.23 | 78.28 |
| 0.05M BIS-TRIS pH 6.5, 1M Sodium chloride | 52.70 | 81.80 |
| 0.05M Imidazole pH 7.0, 1M Sodium chloride | 53.29 | 81.93 |
| 0.05M HEPES pH 7.5, 1M Sodium chloride | 54.57 | 83.41 |
| 0.05M Tris pH 8.0, 1M Sodium chloride | 54.12 | 83.39 |
| 0.05M BIS-TRIS Propane pH 8.5, 1M Sodium chloride | 53.94 | 83.72 |
| 0.05M AMPD pH 9.0, 1M Sodium chloride | 53.26 | 83.03 |
| 0.05M Glycine pH 9.5, 1M Sodium chloride | 53.41 | 83.48 |

Thermostability of VRT-5 increased as NaCl concentration increased.

| Conditions | Tagg (° C.) | Tagg (° C.) |
|---|---|---|
| Water | 48.76 | 56.74 |
| 0.05M NaCl | 51.05 | 70.25 |
| 0.1M NaCl | 51.82 | 72.05 |
| 0.15M NaCl | 52.24 | 77.97 |
| 0.2M NaCl | 52.35 | 78.98 |
| 0.25M NaCl | 52.59 | 80.17 |
| 0.5M NaCl | 53.42 | 81.91 |
| 1M NaCl | 54.34 | 83.31 |

Thermostability of VRT-5 increased when the chemicals provided in the table below were included in solution.

| Conditions in water | Tm (° C.) | Tagg (° C.) |
|---|---|---|
| Water | 48.76 | 56.74 |
| 1M D-sorbitol | 53.37 | 77.07 |
| 1M sucrose | 54.32 | 82.72 |
| 0.5M sodium sulfate decahydrate | 55.45 | 55.09 |
| 0.5M NaCl | 53.44 | 81.80 |
| 0.25M sodium malonate pH 7.0 | 54.35 | 54.65 |
| 0.25M succinic acid pH 7.0 | 54.71 | 54.49 |
| 0.25M DL-malic acid pH 7.0 | 54.87 | 54.73 |
| 0.375M D-(+)-Trehalose dihydrate | 51.48 | 56.74 |
| 1.25M Betaine monohydrate | 52.35 | 73.38 |
| 1M Xylitol | 52.41 | 82.37 |
| 2.5% v/v Tacsimate pH 7.0 | 52.70 | 75.57 |
| 25% v/v Glycerol | 52.77 | 58.48 |
| 1.25M Trimethylamine N-oxide dihydrate | 54.00 | 84.17 |

Combination of D-sorbitol, Sucrose, and sodium sulfate in one buffer produced synergistic increase of thermostability.

| Conditions | Excipients | Tm (° C.) | Tagg (° C.) |
|---|---|---|---|
| Water control | None | 47.24 | 56.43 |
| pH 3.5 Glycine 50 mM, 166 mM NaCl | NaCl | 51.76 | 73.15 |
| pH 3.5 Glycine 50 mM, 166 mM NaCl, 350 mM D-sorbitol | NaCl + D-sorbitol | 53.08 | 80.92 |
| pH 3.5 Glycine 50 mM, 166 mM NaCl, 175 mM sodium sulfate decahydrate | NaCl + sodium sulfate decahydrate | 53.17 | 79.79 |
| pH 3.5 Glycine 50 mM, 166 mM NaCl, 350 mM sucrose | NaCl + sucrose | 53.87 | 84.00 |
| pH 3.5 Glycine 50 mM, 166 mM NaCl, 350 mM D-sorbitol, 350 mM sucrose | NaCl + D-sorbitol + sucrose | 54.96 | 85.29 |
| pH 3.5 Glycine 50 mM, 166 mM NaCl, 350 mM D-sorbitol, 175 mM sodium sulfate decahydrate | NaCl + D-sorbitol + sodium sulfate decahydrate | 55.06 | 83.27 |
| pH 3.5 Glycine 50 mM, 166 mM NaCl, 350 mM sucrose, 175 mM sodium sulfate decahydrate | NaCl + sucrose + sodium sulfate decahydrate | 55.44 | 85.22 |
| pH 3.5 Glycine 50 mM, 166 mM NaCl, 350 mM D-sorbitol, 350 mM sucrose, 175 mM sodium sulfate decahydrate | NaCl + D-sorbitol + sucrose + sodium sulfate decahydrate | 56.94 | Too close to 90° C. to be measured |

Example 8: Fc-IdeS Fusion Molecule Exhibits Extended PK and PD In Vivo

Figure 2A:
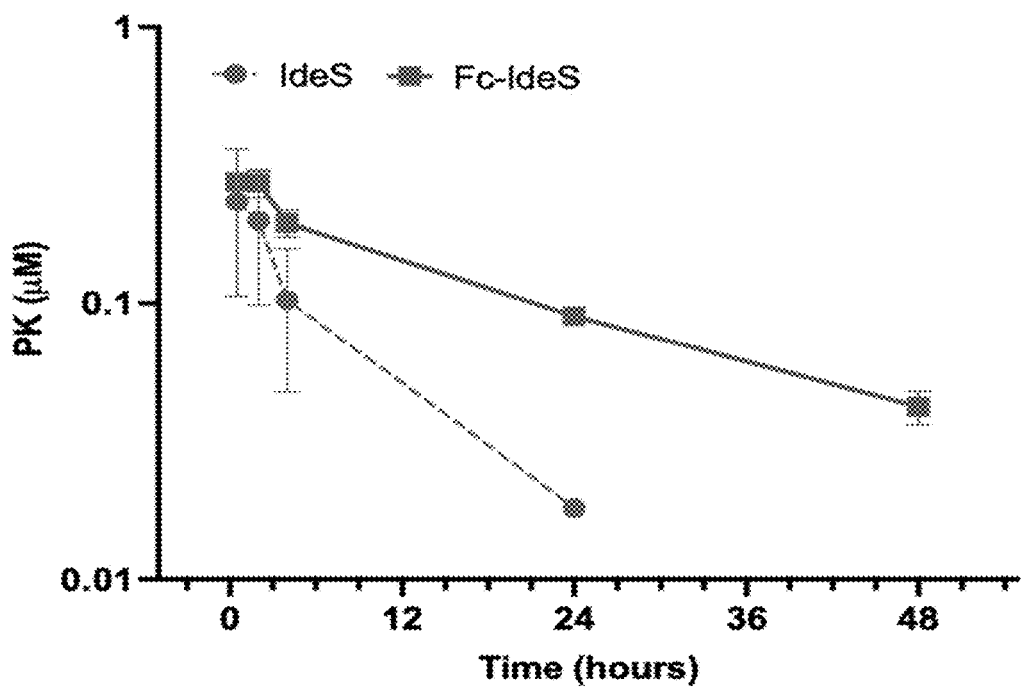
FIG. 2A illustrates PK measurements.
Figure 2B:
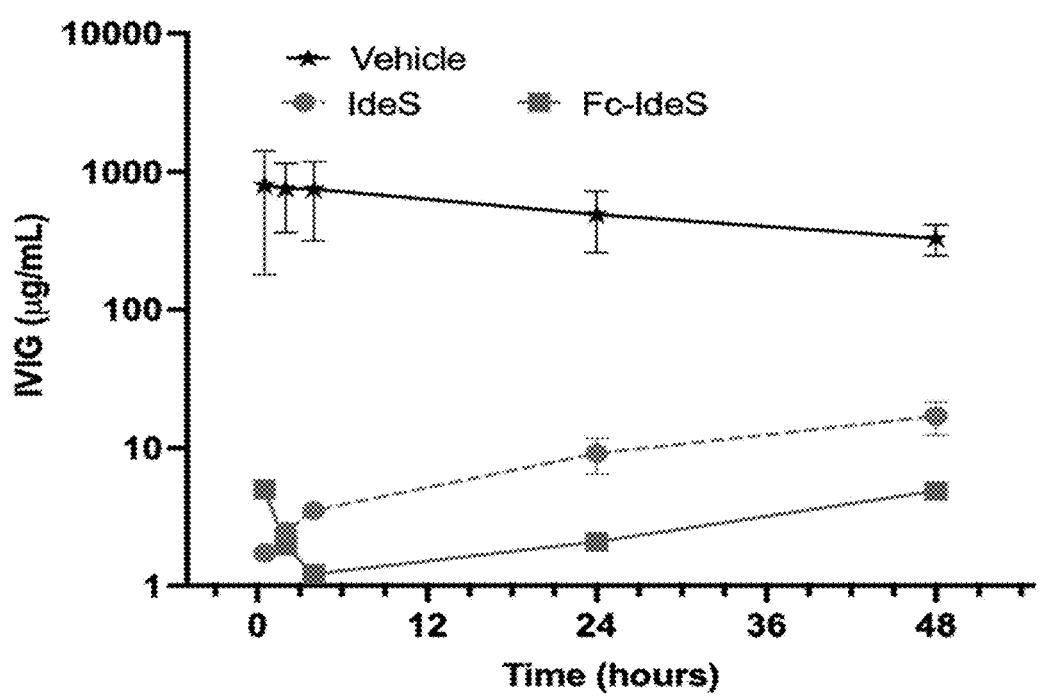
FIG. 2B illustrates PD measurements.

C57BL/6 mice (n=3/group) were injected with human intravenous immunoglobulin (IVIG) and allowed to equilibrate for 24 hours before being injected with the vehicle, IdeS protease (0.5 mg/kg), or the Fc-IdeS fusion molecule (0.9 mg/kg). Mice were euthanized for blood collection at 0 hours, 0.5 hours, 2 hours, 4 hours, 24 hours, and 48 hours following injection of the vehicle, IdeS, or Fc-IdeS. Plasma was collected for exposure analysis and measurement of human IgG levels. Fc-IdeS exhibited extended PK in mice in the presence of human IgG (FIG. 2A), as compared to IdeS. Fc-IdeS also exhibited improved PD as evidence by improved IVIG cleavage (FIG. 2B).

Example 9: Fc-IdeS Fusion Molecule Remains Active In Vivo for at Least 4 Days

Figure 3:
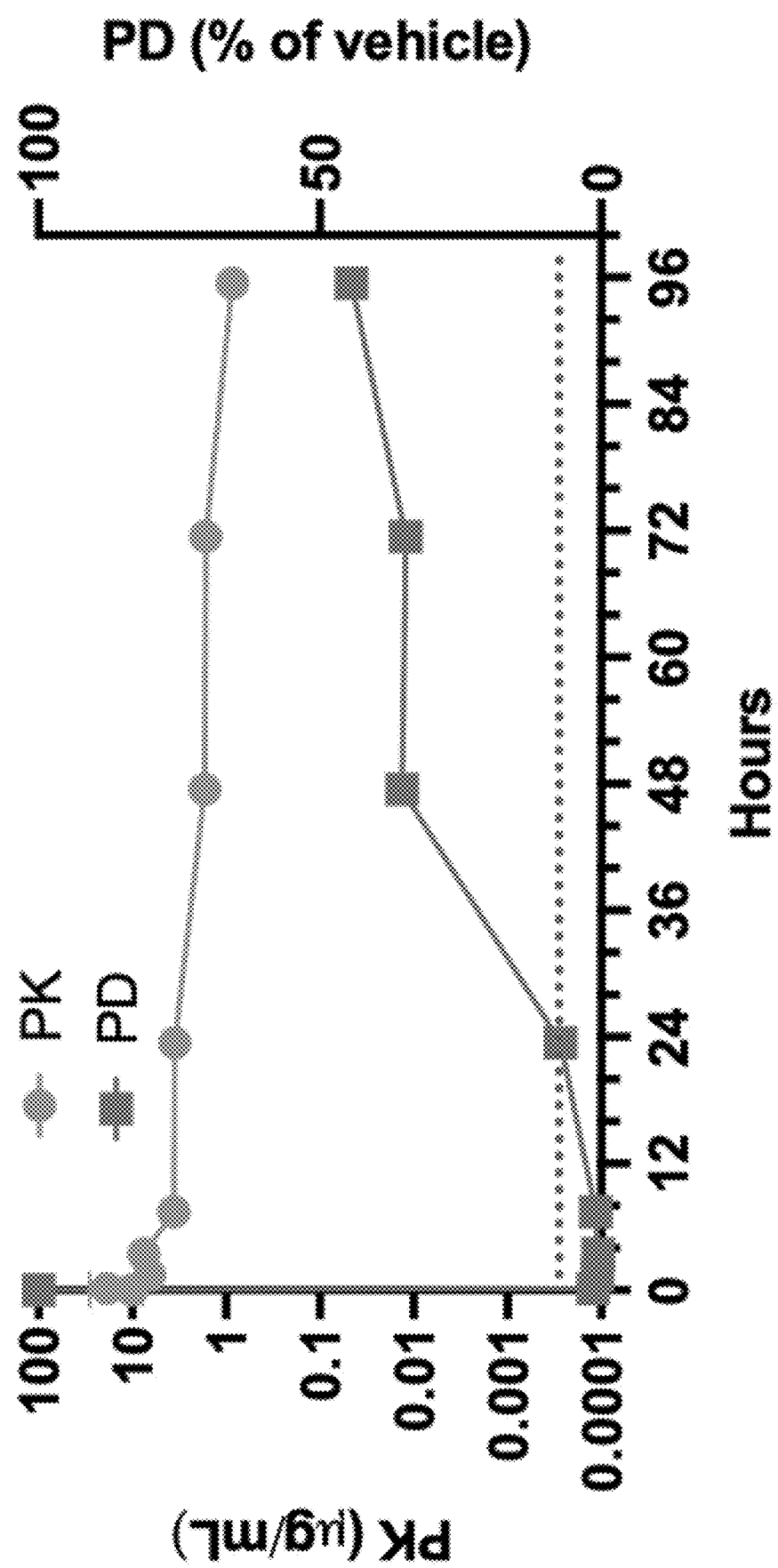
FIG. 3 illustrates PK and PD measurements.

C57BL/6 mice (n=6 for the vehicle treated mice; and n=3 per group for the Fc-IdeS treated mice) were injected intravenously with 0.9 mg/kg Fc-IdeS, followed by injection of human intravenous immunoglobulin (IVIG) at 0.5 hours, 2 hours, 4 hours, 6 hours, 8 hours, 24 hours, 48 hours, 72 hours, or 96 hours following Fc-IdeS injection. Blood was first collected 15 minutes prior to injection of IVIG for PK determination, and mice were euthanized 2 hours after IVIG injection for PD measurements. Fc-IdeS exhibited extended PK in mice (FIG. 3). PD analysis showed reduced human IgG level even 4 days following injection with Fc-IdeS, illustrating that Fc-IdeS remained active 4 days after injection in mice (FIG. 3).

Figure 4A:
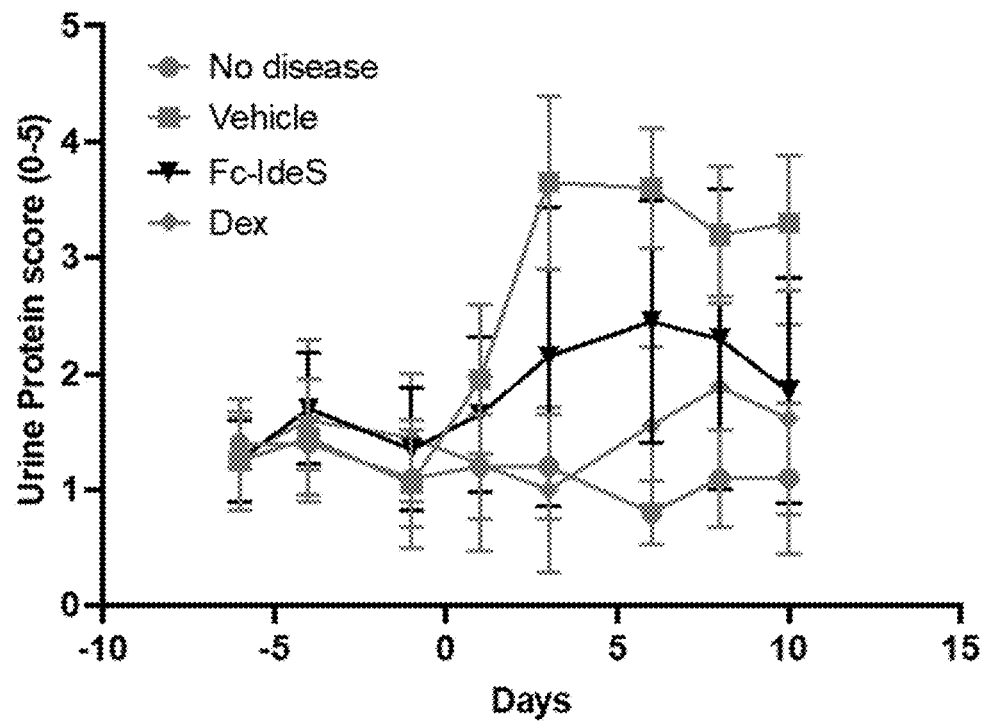
FIG. 4A illustrates urine protein scores.
Figure 4B:
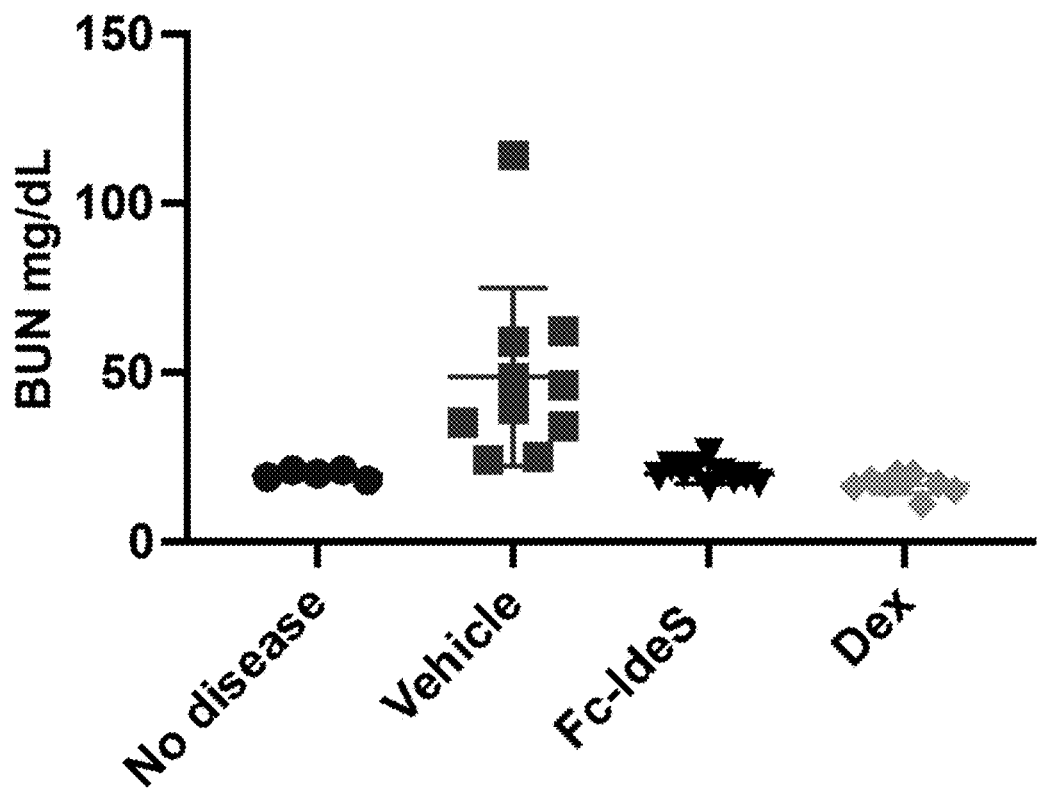
FIG. 4B illustrates blood urea nitrogen levels.

Example 10: Fc-IdeS Demonstrates Efficacy in an IgG Immune Complex-Mediated Kidney Disease In Vivo Model Without wishing to be bound to a particular theory, pathology in the anti-GBM (glomerular basement membrane) mouse model of kidney disease is driven by immune complex deposition in the kidneys. Immune complexes bind to the glomerular basement membrane in the kidney, inducing tissue damage via complement activation, proteinuria and an increase in blood urea nitrogen (BUN). Fc-IdeS was used to treat the disease by cleaving sheep IgG immune complexes prophylactically. In brief, female 129/SvJ mice (n=10 per group) were sensitized by immunization with sheep IgG (IP injection) followed by injection of sheep ant-rat GBM serum (which is cross-reactive to mouse GBM) five days following immunization. At 4 days following immunization, mice were intravenously injected with 8 mg/kg Fc-IdeS, a vehicle, or dexamethasone (dex). Mice were euthanized 15 days following immunization. Plasma PK was measured at days 5 and 15 following immunization. Proteinuria was measured the day before immunization and at days 1, 4, 6, 8, 11, 13, and 15 following immunization. Blood urea nitrogen (BUN) was measured at day 15 following immunization. Additionally, kidney histology was assessed at day 15 following immunization. Prophylactic treatment with Fc-IdeS prevented immune complex-driven proteinuria and increase in blood urea nitrogen (BUN), as shown in FIGS. 4A-4B.

Example 11: In Vivo PK/PD of an Fc-Protease Shows Greater than 90% Reduction in Human IVIG at 30 Min after Dosing C57/BL6 mice were administered intravenous immune globulin (IVIG) at a dose of 450 mg/kg, and randomized based on body weight for treatment with a VFC-5 fused to an exemplary protease administered intravenously at various doses, or a vehicle control (PBS). Treatment was administered at 1 hour following administration of IVIG. Blood was collected at 0.5 hours, 2 hours, 4 hours, 24 hours, 48 hours, and 72 hours following treatment. The VFC-5 fused to an exemplary protease had a half-life extending 24 hours, and showed a greater than 90% reduction of IVIG at all tested timepoints and at both treatment doses relative to vehicle treated animals.

Example 12: In Vivo PK/PD of an Fc-Protease Shows Greater than 95% Reduction in Human IVIG at 30 Min after Dosing C57/BL6 animals were administered IVIG at a dose of 450 mg/kg, and randomized based on body weight for treatment with a VFC-5 fused to an exemplary protease administered intravenously, or a vehicle control (PBS). Treatment was administered 1 hour following administration of IVIG. Blood was collected at 0.5 hours, 2 hours, 4 hours, 24 hours, 48 hours, and 72 hours following treatment. The VFC-5 fused to an exemplary protease showed a half-life extending 24 hours, and greater than 95% reduction in blood IVIG at all tested timepoints relative to vehicle treated animals.

The disclosures of each and every patent, patent application, and publication cited herein are hereby incorporated herein by reference in their entirety. While various embodiments have been disclosed with reference to specific aspects, it is apparent that other aspects and variations of these embodiments may be devised by others skilled in the art without departing from the true spirit and scope of the embodiments. The appended claims are intended to be construed to include all such aspects and equivalent variations.

What is claimed:

1. A Fc polypeptide comprising the amino acid sequence of SEQ ID NO: 23.

2. A composition comprising a homodimer comprising a first Fc polypeptide and a second Fc polypeptide, wherein the first Fc polypeptide and the second Fc polypeptide each comprise the Fc polypeptide of claim 1.

3. A molecule comprising the Fc polypeptide of claim 1 linked to a protease.

4. The molecule of claim 3, wherein the Fc polypeptide consists of the amino acid sequence of SEQ ID NO: 23.

5. The molecule of claim 3, wherein the Fc polypeptide is linked to the protease via a peptide linker.

6. The molecule of claim 3, wherein the protease is an IgG protease.

7. The molecule of claim 3, wherein the protease is selected from IdeS, IdeSsuis, IdeE, IdeZ, IdeE2, IdeZ2, or IdeC protease.

8. The molecule of claim 3, wherein the protease is an IdeS protease.

9. A pharmaceutical composition comprising the Fc polypeptide of claim 1.

10. A pharmaceutical composition comprising the molecule of claim 3.

11. A pharmaceutical composition comprising the composition of claim 2.

12. A pharmaceutical composition comprising the molecule of claim 4.

13. A pharmaceutical composition comprising the molecule of claim 5.

14. A pharmaceutical composition comprising the molecule of claim 6.

15. A pharmaceutical composition comprising the molecule of claim 7.

16. A pharmaceutical composition comprising the molecule of claim 8.

* * * * *

SEQUENCE LISTING

```
Sequence total quantity: 68
SEQ ID NO: 1            moltype = AA  length = 330
FEATURE                 Location/Qualifiers
source                  1..330
                        mol_type = protein
                        organism = synthetic construct
SEQUENCE: 1
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 2            moltype = AA  length = 326
FEATURE                 Location/Qualifiers
source                  1..326
                        mol_type = protein
                        organism = synthetic construct
SEQUENCE: 2
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDISVEW ESNGQPENNY KTTPPMLDSD GSFFLYSKLT VDKSRWQQGN  300
VFSCSVMHEA LHNHYTQKSL SLSPGK                                       326

SEQ ID NO: 3            moltype = AA  length = 377
FEATURE                 Location/Qualifiers
source                  1..377
                        mol_type = protein
                        organism = synthetic construct
SEQUENCE: 3
ASTKGPSVFP LAPCSRSTSG GTAALGCLVK DYFPEPVTVS WNSGALTSGV HTFPAVLQSS  60
GLYSLSSVVT VPSSSLGTQT YTCNVNHKPS NTKVDKRVEL KTPLGDTTHT CPRCPEPKSC  120
DTPPPCPRCP EPKSCDTPPP CPRCPEPKSC DTPPPCPRCP APELLGGPSV FLFPPKPKDT  180
LMISRTPEVT CVVVDVSHED PEVQFKWYVD GVEVHNAKTK PREEQYNSTF RVVSVLTVLH  240
QDWLNGKEYK CKVSNKALPA PIEKTISKTK GQPREPQVYT LPPSREEMTK NQVSLTCLVK  300
GFYPSDIAVE WESSGQPENN YNTTPPMLDS DGSFFLYSKL TVDKSRWQQG NIFSCSVMHE  360
ALHNRFTQKS LSLSPGK                                                 377

SEQ ID NO: 4            moltype = AA  length = 327
FEATURE                 Location/Qualifiers
source                  1..327
                        mol_type = protein
                        organism = synthetic construct
SEQUENCE: 4
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                      327

SEQ ID NO: 5            moltype = AA  length = 23
FEATURE                 Location/Qualifiers
source                  1..23
```

```
                        mol_type = protein
                        organism = synthetic construct
SEQUENCE: 5
EPKSCDKTHT CPPCPAPELL GGP                                             23

SEQ ID NO: 6            moltype = AA   length = 25
FEATURE                 Location/Qualifiers
source                  1..25
                        mol_type = protein
                        organism = synthetic construct
SEQUENCE: 6
ELKTPLGDTT HTCPRCPAPE LLGGP                                           25

SEQ ID NO: 7            moltype = AA   length = 70
FEATURE                 Location/Qualifiers
source                  1..70
                        mol_type = protein
                        organism = synthetic construct
SEQUENCE: 7
ELKTPLGDTT HTCPRCPEPK SCDTPPPCPR CPEPKSCDTP PPCPRCPEPK SCDTPPPCPR     60
CPAPELLGGP                                                            70

SEQ ID NO: 8            moltype = AA   length = 20
FEATURE                 Location/Qualifiers
source                  1..20
                        mol_type = protein
                        organism = synthetic construct
SEQUENCE: 8
ESKYGPPCPS CPAPEFLGGP                                                 20

SEQ ID NO: 9            moltype =     length =
SEQUENCE: 9
000

SEQ ID NO: 10           moltype =     length =
SEQUENCE: 10
000

SEQ ID NO: 11           moltype =     length =
SEQUENCE: 11
000

SEQ ID NO: 12           moltype =     length =
SEQUENCE: 12
000

SEQ ID NO: 13           moltype =     length =
SEQUENCE: 13
000

SEQ ID NO: 14           moltype =     length =
SEQUENCE: 14
000

SEQ ID NO: 15           moltype =     length =
SEQUENCE: 15
000

SEQ ID NO: 16           moltype =     length =
SEQUENCE: 16
000

SEQ ID NO: 17           moltype =     length =
SEQUENCE: 17
000

SEQ ID NO: 18           moltype =     length =
SEQUENCE: 18
000

SEQ ID NO: 19           moltype = AA   length = 227
FEATURE                 Location/Qualifiers
source                  1..227
                        mol_type = protein
                        organism = synthetic construct
SEQUENCE: 19
DKTHTCPPCP APEAAGAPSV FLFPPKPKDT LMISRTPEVT CVVVDVSHED PEVKFNWYVD     60
GVEVHNAKTK PREEQQNSTY RVVSVLTVLH QDWLNGKEYK CKVSNKALKA PIEKTISKAK    120
GQPREPQVYT LPPSRDELTK NQVSLTCLVK GFYPSDIAVE WESNGQPENN YKTTPPVLDS    180
```

```
DGSFFLYSKL TVDKSRWQQG NVFSCSVMHE ALHNHYTQKS LSLSPGK            227

SEQ ID NO: 20          moltype = AA  length = 227
FEATURE                Location/Qualifiers
source                 1..227
                       mol_type = protein
                       organism = synthetic construct
SEQUENCE: 20
DKTHTCPPCP APEAAGAPSV FLFPPKPKDT LMISRTPEVT CVVVDVSHED PEVKFNWYVD 60
GVEVHNAKTK PREEQYNSTY RVVSVLTVLH QDWLNGKEYK CKVSNKALPA PIEKTISKAK 120
GQPREPQVYT LPPSRDELTK NQVSLTCLVK GFYPSDIAVE WESNGQPENN YKTTPPVLDS 180
DGSFFLYSKL TVDKSRWQQG NVFSCSVMHE ALHNHYTQKS LSLSPGK            227

SEQ ID NO: 21          moltype = AA  length = 227
FEATURE                Location/Qualifiers
source                 1..227
                       mol_type = protein
                       organism = synthetic construct
SEQUENCE: 21
DKTHTCPPCP APEAAGAPSV FLFPPKPKDT LMISRTPEVT CVVVKVSHSD PEVKFNWYVD 60
GVEVHNAKTK PREEQQNSTY RVVSVLTVLH QDWLNGKEYK CKVSNKALKA PIEKTISKAK 120
GQPREPQVYT LPPSRDELTK NQVSLTCLVK GFYPSDIAVE WESNGQPENN YKTTPPVLDS 180
DGSFFLYSKL TVDKSRWQQG NVFSCSVMHE ALHNHYTQKS LSLSPGK            227

SEQ ID NO: 22          moltype = AA  length = 227
FEATURE                Location/Qualifiers
source                 1..227
                       mol_type = protein
                       organism = synthetic construct
SEQUENCE: 22
DKTHTCPPCP APEAAGAPSV FLFPPKPKDT LMISRTPEVT CVVVKVSHSD PEVKFNWYVD 60
GVEVHNAKTK PREEQQNKTY RVVSVLTVLH QDWLNGKEYK CKVSNKALKA PIEKTISKAK 120
GQPREPQVYT LPPSRDELTK NQVSLTCLVK GFYPSDIAVE WESNGQPENN YKTTPPVLDS 180
DGSFFLYSKL TVDKSRWQQG NVFSCSVMHE ALHNHYTQKS LSLSPGK            227

SEQ ID NO: 23          moltype = AA  length = 226
FEATURE                Location/Qualifiers
source                 1..226
                       mol_type = protein
                       organism = synthetic construct
SEQUENCE: 23
DKTHTCPPCP APEAAGAPSV FLFPPKPKDT LMISRTPEVT CVVVDVSHED PEVKFNWYVD 60
GVEVHNAKTK PREEQQNSTY RVVSVLTVLH QDWLNGKEYK CKVSNKALKA PIEKTISKAK 120
GQPREPQVYT LPPSRDELTK NQVSLTCLVK GFYPSDIAVE WESNGQPENN YKTTPPVLDS 180
DGSFFLYSKL TVDKSRWQQG NVFSCSVMHE ALHNHYTQKS LSLSPG            226

SEQ ID NO: 24          moltype = AA  length = 226
FEATURE                Location/Qualifiers
source                 1..226
                       mol_type = protein
                       organism = synthetic construct
SEQUENCE: 24
DKTHTCPPCP APEAAGAPSV FLFPPKPKDT LMISRTPEVT CVVVDVSHED PEVKFNWYVD 60
GVEVHNAKTK PREEQQNSTY RVVSVLTVLH QDWLNGKEYK CKVSNKALKA PIEKTISKAK 120
GQPREPQVYT LPPSRDELTK NQVSLWCLVK GFYPSDIAVE WESNGQPENN YKTTPPVLDS 180
DGSFFLYSKL TVDKSRWQQG NVFSCSVMHE ALHNHYTQKS LSLSPG            226

SEQ ID NO: 25          moltype = AA  length = 226
FEATURE                Location/Qualifiers
source                 1..226
                       mol_type = protein
                       organism = synthetic construct
SEQUENCE: 25
DKTHTCPPCP APEAAGAPSV FLFPPKPKDT LMISRTPEVT CVVVDVSHED PEVKFNWYVD 60
GVEVHNAKTK PREEQQNSTY RVVSVLTVLH QDWLNGKEYK CKVSNKALKA PIEKTISKAK 120
GQPREPQVYT LPPSRDELTK NQVSLSCAVK GFYPSDIAVE WESNGQPENN YKTTPPVLDS 180
DGSFFLVSKL TVDKSRWQQG NVFSCSVMHE ALHNHYTQKS LSLSPG            226

SEQ ID NO: 26          moltype = AA  length = 306
FEATURE                Location/Qualifiers
source                 1..306
                       mol_type = protein
                       organism = synthetic construct
SEQUENCE: 26
ANQEIRYSEV TPYHVTSVWT KGVTPPAQFT QGEDVFHAPY VANQGWYDIT KTFNGKDDLL 60
CGAATAGNML HWWFDQNKDQ IKRYLEEHPE KQKINFNGEQ MFDVKEAIDT KNHQLDSKLF 120
EYFKEKAFPY LSTKHLGVFP DHVIDMFING YRLSLTNHGP TPVKEGSKDP RGGIFDAVFT 180
RGDQSKLLTS RHDFKEKNLK EISDLIKKEL TEGKALGLSH TYANVRINHV INLWGADFDS 240
NGNLKAIYVT DSDSNASIGM KKYFVGVNSA GKVAISAKEI KEDNIGAQVL GLFTLSTGQD 300
```

```
SWNQTN                                                                        306

SEQ ID NO: 27           moltype = AA   length = 8
FEATURE                 Location/Qualifiers
source                  1..8
                        mol_type = protein
                        organism = synthetic construct
SEQUENCE: 27
HHHHHHHH                                                                        8

SEQ ID NO: 28           moltype = AA   length = 306
FEATURE                 Location/Qualifiers
source                  1..306
                        mol_type = protein
                        organism = synthetic construct
SEQUENCE: 28
ANQEIRYSEV TPYHVTSVWT KNVTPPAQFT QGEDVFHAPY VANQGWYDIT KTFNGKDDLL               60
CGAATAGNML HWWFDQNKDQ IKRYLEEHPE KQKINFNGSQ MFDVKEAIDT KNHQLDSKLF              120
EYFKEKAFPY LSTKHLGVFP DHVIDMFING YRLSLNNSGP TPVKNGSKDP RGGIFDAVFT              180
RGDQSKLLTS RHDFKNKSLK EISDLIKKEL TEGKALGLSH TYANVRINHV INLWGADFDS              240
NGTLKAIYVT DSDSNASIGM KKYFVGVNNA TKVAISAKEI KENNTGAQVL GLFTLSTGQD              300
SWNQTN                                                                        306

SEQ ID NO: 29           moltype = AA   length = 306
FEATURE                 Location/Qualifiers
source                  1..306
                        mol_type = protein
                        organism = synthetic construct
SEQUENCE: 29
ANQEIRYSEV TPYHVTSVWT KGVTPPAQFT QGEDVFHAPY VANQGWYDIT KTFNGKDDLL               60
CGAATAGNML HWWFDQNKDQ IKRYLEEHPE KQKINFNGEQ MFDVKEAIDT KNHQLDSKLF              120
EYFKEKAFPY LSTKHLGVFP DHVIDMFING YRLSLTNHGP TPVKEGSKDP RGGIFDAVFT              180
RGDQSKLLTS RHDFKEKNLK EISDLIKKEL TEGKALGLSH TYANVRINHV INLWGADFDS              240
NGNLKAIYVT DSDSNAQIGM KKYFVGVNSA GKVAISAKEI KEDNIGAQVL GLFTLSTGQD              300
SWNQTN                                                                        306

SEQ ID NO: 30           moltype = AA   length = 125
FEATURE                 Location/Qualifiers
source                  1..125
                        mol_type = protein
                        organism = synthetic construct
SEQUENCE: 30
QVQLQESGGG LVQAGGSLRL SCAASGYISD AYYMGWYRQA PGKEREFVAT ITHGTNTYYA               60
DSVKGRFTIS RDNAKNTVYL QMNSLKPEDT AVYYCAVLET RSYSFRYWGQ GTQVTVSSLE              120
GGGGS                                                                         125

SEQ ID NO: 31           moltype = AA   length = 311
FEATURE                 Location/Qualifiers
source                  1..311
                        mol_type = protein
                        organism = synthetic construct
SEQUENCE: 31
ANQEIRYSEV TPYHVTSVWT KGVTPPAQFT QGEDVFHAPY VANQGWYDIT KTFNGKDDLL               60
CGAATAGNML HWWFDQNKDQ IKRYLEEHPE KQKINFNGEQ MFDVKEAIDT KNHQLDSKLF              120
EYFKEKAFPY LSTKHLGVFP DHVIDMFING YRLSLTNHGP TPVKEGSKDP RGGIFDAVFT              180
RGDQSKLLTS RHDFKEKNLK EISDLIKKEL TEGKALGLSH TYANVRINHV INLWGADFDS              240
NGNLKAIYVT DSDSNAQIGM KKYFVGVNSA GKVAISAKEI KEDNIGAQVL GLFTLSTGQD              300
SWNQTNGGGG S                                                                  311

SEQ ID NO: 32           moltype = AA   length = 122
FEATURE                 Location/Qualifiers
source                  1..122
                        mol_type = protein
                        organism = synthetic construct
SEQUENCE: 32
QVQLQESGGG LVQAGGSLRL SCAASGYISD AYYMGWYRQA PGKEREFVAT ITHGTNTYYA               60
DSVKGRFTIS RDNAKNTVYL QMNSLKPEDT AVYYCAVLET RSYSFRYWGQ GTQVTVSSLE              120
GG                                                                            122

SEQ ID NO: 33           moltype = AA   length = 120
FEATURE                 Location/Qualifiers
source                  1..120
                        mol_type = protein
                        organism = synthetic construct
SEQUENCE: 33
QVQLQESGGG LVQAGGSLRL SCAASGYISD AYYMGWYRQA PGKEREFVAT ITHGTNTYYA               60
DSVKGRFTIS RDNAKNTVYL QMNSLKPEDT AVYYCAVLET RSYSFRYWGQ GTQVTVSSLE              120

SEQ ID NO: 34           moltype =      length =
```

```
SEQUENCE: 34
000

SEQ ID NO: 35              moltype = AA   length = 339
FEATURE                    Location/Qualifiers
source                     1..339
                           mol_type = protein
                           organism = synthetic construct
SEQUENCE: 35
MRKRCYSTSA AVLAAVTLFV LSVDRGVIAD SFSANQEIRY SEVTPYHVTS VWTKGVTPPA    60
NFTQGEDVFH APYVANQGWY DITKTFNGKD DLLCGAATAG NMLHWWFDQN KDQIKRYLEE   120
HPEKQKINFN GEQMFDVKEA IDTKNHQLDS KLFEYFKEKA FPYLSTKHLG VFPDHVIDMF   180
INGYRLSLTN HGPTPVKEGS KDPRGGIFDA VFTRGDQSKL LTSRHDFKEK NLKEISDLIK   240
KELTEGKALG LSHTYANVRI NHVINLWGAD FDSNGNLKAI YVTDSDSNAS IGMKKYFVGV   300
NSAGKVAISA KEIKEDNIGA QVLGLFTLST GQDSWNQTN                          339

SEQ ID NO: 36              moltype = AA   length = 306
FEATURE                    Location/Qualifiers
source                     1..306
                           mol_type = protein
                           organism = synthetic construct
SEQUENCE: 36
ANQEIRYSEV TPYHVTSVWT KGVTPPANFT QGEDVFHAPY VANQGWYDIT KTFNGKDDLL    60
CGAATAGNML HWWFDQNKDQ IKRYLEEHPE KQKINFNGEQ MFDVKEAIDT KNHQLDSKLF   120
EYFKEKAFPY LSTKHLGVFP DHVIDMFING YRLSLTNHGP TPVKEGSKDP RGGIFDAVFT   180
RGDQSKLLTS RHDFKEKNLK EISDLIKKEL TEGKALGLSH TYANVRINHV INLWGADFDS   240
NGNLKAIYVT DSDSNASIGM KKYFVGVNSA GKVAISAKEI KEDNIGAQVL GLFTLSTGQD   300
SWNQTN                                                              306

SEQ ID NO: 37              moltype = AA   length = 315
FEATURE                    Location/Qualifiers
source                     1..315
                           mol_type = protein
                           organism = synthetic construct
SEQUENCE: 37
DDYQRNATEA YAKEVPHQIT SVWTKGVTPL TPEQFRYNNE DVIHAPYLAH QGWYDITKAF    60
DGKDNLLCGA ATAGNMLHWW FDQNKTEIEA YLSKHPEKQK IIFNNQELFD LKAAIDTKDS   120
QTNSQLFNYF RDKAFPNLSA RQLGVMPDLV LDMFINGYYL NVFKTQSTDV NRPYQDKDKR   180
GGIFDAVFTR GDQTTLLLAR HDLKNKGLND ISTIIKQELT EGRALALSHT YANVSISHVI   240
NLWGADFNAE GNLEAIYVTD SDANASIGMK KYFVGINAHR HVAISAKKIE GENIGAQVLG   300
LFTLSSGKDI WQKLS                                                   315

SEQ ID NO: 38              moltype = AA   length = 315
FEATURE                    Location/Qualifiers
source                     1..315
                           mol_type = protein
                           organism = synthetic construct
SEQUENCE: 38
DDYQRNATEA YAKEVPHQIT SVWTKGVTPL TPEQFRYNNE DVIHAPYLAH QGWYDITKAF    60
DGKDNLLCGA ATAGNMLHWW FDQNKTEIEA YLSKHPEKQK IIFNNQELFD LKAAIDTKDS   120
QTNSQLFNYF RDKAFPNLSA RQLGVMPDLV LDMFINGYYL NVFKTQSTDV NRPYQDKDKR   180
GGIFDAVFTR GDQTTLLLAR HDLKNKGLND ISTIIKQELT EGRALALSHT YANVSISHVI   240
NLWGADFNAE GNLEAIYVTD SDANASIGMK KYFVGINAHG HVAISAKKIE GENIGAQVLG   300
LFTLSSGKDI WQKLS                                                   315

SEQ ID NO: 39              moltype = AA   length = 344
FEATURE                    Location/Qualifiers
source                     1..344
                           mol_type = protein
                           organism = synthetic construct
SEQUENCE: 39
EVVEVWPNGQ NPNGKIEILS QTEHSEHLQK LRDIEDFQAQ KQADHVRYTK WLDGVTVDEH    60
EFRKIKEYDT EYYVTPLLSG KGYYDINKDF NQDSDKCAAA VAANMFHYWW DRNRDSINRF   120
LSQSPGENGV IKLENEKTIE VSKFLETYRS DGDYLDKSPF FDLISNSFKG PVWANKLLDA   180
YINGYGYIHK FAKNTPHSKN NNSKFNFFKK VFDGNLLTDI HQIFDYNTFS DKLSEALYTG   240
KAIGLAYGPG DLRRSLGHII SVWGADLDDQ NRVVAIYVTD SDDKKLTIGN ERVGLKRYKV   300
SSDDQGRARL TTRDKDNTGG EIRSIETLDM GTQEWADYFN KTEK                    344

SEQ ID NO: 40              moltype = AA   length = 352
FEATURE                    Location/Qualifiers
source                     1..352
                           mol_type = protein
                           organism = synthetic construct
SEQUENCE: 40
EVVEVWPYGQ NPNGKTEILS QTEDSESLQR LRDIEDFQAE KKMQNVVYTK WLDGVDVKDH    60
DFRKIVDGNI AYYATPLLNG RGFYDINKDP NRDSDKCAAA VAANMFHYWL DINRDNVDRF   120
LRQNPEKHGI IELPDGQLKL SDFLNTYESD HGYRDKSKLF DFISNNFNGP VWTDKLLDNY   180
INGYAYNYKY GRTIEDPTKN TSKINFFKEV FNEKILTNNH SIRNQNEFSV LLSEALYTGK   240
AIGLSYGPAG LRHSLGHIIS VWGADLDADG NVVAIYVTDS DDKKLTIGDE RVGLKRYKIS   300
```

```
TDDENRLRLT AYEETHNTGG QIRGLWTLDT GKYAWADYFD KTEQTGTDQA EQ            352

SEQ ID NO: 41            moltype = AA  length = 306
FEATURE                  Location/Qualifiers
source                   1..306
                         mol_type = protein
                         organism = synthetic construct
SEQUENCE: 41
RNQITTYSEA TPSHITSIWT KGVTPPTNFI EGTDGSHAPY IANQGWYDIT KTFNGKDDLL    60
CAAATAGNML HWWFDQNKNQ IEGYLTEHPE KQAIIFNGEK MFDVKEAIST KDRQLDSKLF   120
EYFKEKAFPT LSARRRGVFP DHVIDMFING YRLSLDNYDK TPVKEGNKDL RGGIFDQVFT   180
RGDQSKLLTN RYNLRTKTIN EISQLIKQEL IAGKALAISH TYNNIGISHV INLWGADFNS   240
EGNLEAIYVT DSDSNASIGM KKYYVGVNSA GEVASSKKI DSEHLGAAAL GLYTLSAGQG    300
IWHQTN                                                              306

SEQ ID NO: 42            moltype = AA  length = 227
FEATURE                  Location/Qualifiers
source                   1..227
                         mol_type = protein
                         organism = synthetic construct
SEQUENCE: 42
DKTHTSPPCP APEAAGAPSV FLFPPKPKDT LMISRTPEVT CVVVDVSHED PEVKFNWYVD    60
GVEVHNAKTK PREEQQNSTY RVVSVLTVLH QDWLNGKEYK CKVSNKALKA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 43            moltype = AA  length = 227
FEATURE                  Location/Qualifiers
source                   1..227
                         mol_type = protein
                         organism = synthetic construct
SEQUENCE: 43
DKTHTSPPSP APEAAGAPSV FLFPPKPKDT LMISRTPEVT CVVVDVSHED PEVKFNWYVD    60
GVEVHNAKTK PREEQQNSTY RVVSVLTVLH QDWLNGKEYK CKVSNKALKA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 44            moltype = AA  length = 227
FEATURE                  Location/Qualifiers
source                   1..227
                         mol_type = protein
                         organism = synthetic construct
SEQUENCE: 44
DKTHTCPPCP APELLGDSGV FLFPPKPKDT LMISRTPEVT CVVVDVSHDE PEVKFNWYVD    60
GVEVHNAKTK PREEQYNSTY RVVSVLTVLH QDWLNGKEYK CKVSNKALPR PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 45            moltype = AA  length = 227
FEATURE                  Location/Qualifiers
source                   1..227
                         mol_type = protein
                         organism = synthetic construct
SEQUENCE: 45
DKTHTCPPCP APEFEGGPSV FLFPPKPKDT LMISRTPEVT CVVVDVSDED GEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKS LSLSPGK                 227

SEQ ID NO: 46            moltype = AA  length = 227
FEATURE                  Location/Qualifiers
source                   1..227
                         mol_type = protein
                         organism = synthetic construct
SEQUENCE: 46
DKTHTCPPCP APEFEGGPSV FLFPPKPKDT LMISRTPEVT CVVVDVSQED PEVQFNWYVD    60
GVEVHNAKTK PREEQFNSTY RVVSVLTVLH QDWLNGKEYK CKVSNKALPS SIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 47            moltype = AA  length = 227
FEATURE                  Location/Qualifiers
source                   1..227
                         mol_type = protein
                         organism = synthetic construct
SEQUENCE: 47
DKTHTCPPCP APEFEGGPSV FLFPPKPKDT LMISRTPEVT CVVVDVSDED GEVQFNWYVD    60
GVEVHNAKTK PREEQFNSTY RVVSVLTVLH QDWLNGKEYK CKVSNKALAS SIEKTISKAK   120
GQPREPQVYT LPPSRDELTK NQVSLSCAVK GFYPSDIAVE WESNGQPENN YKTTPPVLDS   180
```

```
DGSFFLVSKL TVDKSRWQQG NVFSCSVMHE ALHNHYTQKS LSLSPGK              227

SEQ ID NO: 48           moltype = AA  length = 227
FEATURE                 Location/Qualifiers
source                  1..227
                        mol_type = protein
                        organism = synthetic construct
SEQUENCE: 48
DKTHTSPPCP APEAAGAPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK 120
GQPREPQVYT LPPSRDELTK NQVSLTCLVK GFYPSDIAVE WESNGQPENN YKTTPPVLDS 180
DGSFFLYSKL TVDKSRWQQG NVFSCSVMHE ALHNHYTQKS LSLSPGK              227

SEQ ID NO: 49           moltype = AA  length = 227
FEATURE                 Location/Qualifiers
source                  1..227
                        mol_type = protein
                        organism = synthetic construct
SEQUENCE: 49
DKTHTSPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK 120
GQPREPQVYT LPPSRDELTK NQVSLTCLVK GFYPSDIAVE WESNGQPENN YKTTPPVLDS 180
DGSFFLYSKL TVDKSRWQQG NVFSCSVMHE ALHNHYTQKS LSLSPGK              227

SEQ ID NO: 50           moltype = AA  length = 306
FEATURE                 Location/Qualifiers
source                  1..306
                        mol_type = protein
                        organism = synthetic construct
SEQUENCE: 50
ANQEIRYSNV TPYHVTSVWT KGVTPPANFT QGEDVFHAPY VANQGWYDIT KTFNGKDDLL  60
CGAATAGNML HWWFDQNKDQ IKRYLEEHPE KQKINFNGEQ MFDVKEAIDT KNHQLDSKLF 120
EYFKEKAFPY LSTKHLGVFP DHVIDMFING YRLSLTNHGP TPVKEGSKDP RGGIFDAVFT 180
RGDQSKLLTS RHDFKEKNLK EISDLIKKEL TEGKALGLSH TYANVRINHV INLWGADFDS 240
NGNLKAIYVT DSDSNASIGM KKYFVGVNSA GKVAISAKEI KEDNIGAQVL GLFTLSTGQD 300
SWNQTN                                                           306

SEQ ID NO: 51           moltype = AA  length = 306
FEATURE                 Location/Qualifiers
source                  1..306
                        mol_type = protein
                        organism = synthetic construct
SEQUENCE: 51
ANQEIRYSEV TPYHNTSVWT KGVTPPANFT QGEDVFHAPY VANQGWYDIT KTFNGKDDLL  60
CGAATAGNML HWWFDQNKDQ IKRYLEEHPE KQKINFNGEQ MFDVKEAIDT KNHQLDSKLF 120
EYFKEKAFPY LSTKHLGVFP DHVIDMFING YRLSLTNHGP TPVKEGSKDP RGGIFDAVFT 180
RGDQSKLLTS RHDFKEKNLK EISDLIKKEL TEGKALGLSH TYANVRINHV INLWGADFDS 240
NGSLKAIYVT DSDSNASIGM KKYFVGVNSA GKVAISAKEI KEDNIGAQVL GLFTLSTGQD 300
SWNQTN                                                           306

SEQ ID NO: 52           moltype = AA  length = 311
FEATURE                 Location/Qualifiers
source                  1..311
                        mol_type = protein
                        organism = synthetic construct
SEQUENCE: 52
RNATEAYAKE VPHQITSVWT KGVTPLTPEQ FRYNNEDVIH APYLAHQGWY DITKAFDGKD  60
NLLCGAATAG NMLHWWFDQN KTEIEAYLSK HPEKQKIIFN NQELFDLKAA IDTKDSQTNS 120
QLFNYFRDKA FPNLSARQLG VMPDLVLDMF INGYYLNVFK TQSTDVNRPY QDKDKRGGIF 180
DAVFTRGDQT TLLTARHDLK NKGLNDISTI IKQELTEGRA LALSHTYANV SISHVINLWG 240
ADFNAEGNLE AIYVTDSDAN ASIGMKKYFV GINAHGHVAI SAKKIEGENI GAQVLGLFTL 300
SSGKDIWQKL S                                                     311

SEQ ID NO: 53           moltype = AA  length = 20
FEATURE                 Location/Qualifiers
source                  1..20
                        mol_type = protein
                        organism = synthetic construct
SEQUENCE: 53
METDTLLLWV LLLWVPGSTG                                             20

SEQ ID NO: 54           moltype = AA  length = 32
FEATURE                 Location/Qualifiers
source                  1..32
                        mol_type = protein
                        organism = synthetic construct
SEQUENCE: 54
MNIQERFSLR KSAVGLVSVS LLCAIYTSTV AA                               32
```

```
SEQ ID NO: 55              moltype = AA  length = 1109
FEATURE                    Location/Qualifiers
source                     1..1109
                           mol_type = protein
                           organism = synthetic construct
SEQUENCE: 55
DTVVTGVNEI IEESQVKDEV SIESEKNESL DGSNIEIVEE IADNIPSPVI AEGEVAVEMK   60
VDRGTENVVS RNDTEVTTSE QNQIEVTETK EILNQTSYQT ESGEQRQIIW AHGITPPAME  120
QSGGFVKEKY GDYLNYTAPF EAGKGYYDTN KSLNASFIDL NLCFAAVSSN MVHWWLEQNS  180
SYVERYLKEK KGTVNVEENY AITDLRRYIN SFQNQQNSRV FDMFKTYYGY RTNGFVSDAL  240
VDLFINGYKP KAQGGVNLED SQLVPDSRGG FFYDVFKEKK LTNRIFSGSY ERFGEDVRTV  300
LESKGLLGLT YRTLGYATHI VTVWGAEYDN QGKIKAVYIT DSDDQQEQIG LKRMGITRDA  360
SGNPRLNNHM KNNSAGALLD YVHTIRLGQD LWEEYFNPLA KAKETASQTL ADTKKALDLS  420
IQGQSELPES MRLIYLEKLN NLYNQGILSI QKAESSEMLS GALENGLNSL KSLDFPISEV  480
GNALAPDLPV GDRSTVSDVD SLSSQETSST NLEADTENAG IIADGTNQLH FPVEAQTTSS  540
VEAEGDNVFE QEADTLPIII ENKDEFGSEL SRNMQTSETD SLVVAVEEDV KNDEVAQVEE  600
LLESEKVENQ SSELLSDTLI VESANDKEED RVEAVVSEQP DSIPHQNVEI SLVEPTNVET  660
ETVVTPINDA ATPHGSPTYI DNSVTESVAT PLEKDSIQAG ETEIAEPTSS ESTNVETETV  720
VTPVNDVATP HGSPTYIDNS VTESVATPLE KDSIQAGETE IAEPTSSEST NVETETVVTP  780
VNDVATPHGS PTYIDNSVTE SVATPLEKDS IQAGETEIAE PTSSESTSVE AELVDNSEIH  840
AATSSVTPCG SSAYADGSTT ESVATPLEKD SIQTGNTEIA EPTSSKSTNV EAASVDNSEI  900
HADASLTAVS SVNLDNPVIE PVAISLIGSK RDTNAEVEVS KREVRKT NTDGLISVQS    960
KVIKKELLES SLAEAGSPLL EATIAQSSNS NSTEIGMSYQ NTVLLESNNT ERQVSKAEIV 1020
MEHKETELVE TVSSASEPVV LVENISQTSN NTIESGKNMG VQSQAGAKQI LGVEQSSKVS 1080
TPTSRQIMGV GLLTLVLGSA LGLLKKRRK                                  1109

SEQ ID NO: 56              moltype = AA  length = 227
FEATURE                    Location/Qualifiers
source                     1..227
                           mol_type = protein
                           organism = synthetic construct
SEQUENCE: 56
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK               227

SEQ ID NO: 57              moltype = AA  length = 5
FEATURE                    Location/Qualifiers
source                     1..5
                           mol_type = protein
                           organism = synthetic construct
SEQUENCE: 57
GGGGS                                                              5

SEQ ID NO: 58              moltype = AA  length = 10
FEATURE                    Location/Qualifiers
source                     1..10
                           mol_type = protein
                           organism = synthetic construct
SEQUENCE: 58
GGGGSGGGGS                                                        10

SEQ ID NO: 59              moltype = AA  length = 15
FEATURE                    Location/Qualifiers
source                     1..15
                           mol_type = protein
                           organism = synthetic construct
SEQUENCE: 59
GGGGSGGGGS GGGGS                                                  15

SEQ ID NO: 60              moltype = AA  length = 20
FEATURE                    Location/Qualifiers
source                     1..20
                           mol_type = protein
                           organism = synthetic construct
SEQUENCE: 60
GGGGSGGGGS GGGGSGGGGS                                             20

SEQ ID NO: 61              moltype = AA  length = 8
FEATURE                    Location/Qualifiers
source                     1..8
                           mol_type = protein
                           organism = synthetic construct
SEQUENCE: 61
GGGGGGGG                                                           8

SEQ ID NO: 62              moltype = AA  length = 6
FEATURE                    Location/Qualifiers
```

```
source                  1..6
                        mol_type = protein
                        organism = synthetic construct
SEQUENCE: 62
GGGGGG                                                                          6

SEQ ID NO: 63           moltype = AA  length = 15
FEATURE                 Location/Qualifiers
source                  1..15
                        mol_type = protein
                        organism = synthetic construct
SEQUENCE: 63
EAAAKEAAAK EAAAK                                                                15

SEQ ID NO: 64           moltype = AA  length = 4
FEATURE                 Location/Qualifiers
source                  1..4
                        mol_type = protein
                        organism = synthetic construct
SEQUENCE: 64
EAAK                                                                            4

SEQ ID NO: 65           moltype = AA  length = 8
FEATURE                 Location/Qualifiers
source                  1..8
                        mol_type = protein
                        organism = synthetic construct
SEQUENCE: 65
EAAKEAAK                                                                        8

SEQ ID NO: 66           moltype = AA  length = 12
FEATURE                 Location/Qualifiers
source                  1..12
                        mol_type = protein
                        organism = synthetic construct
SEQUENCE: 66
EAAKEAAKEA AK                                                                   12

SEQ ID NO: 67           moltype = AA  length = 46
FEATURE                 Location/Qualifiers
source                  1..46
                        mol_type = protein
                        organism = synthetic construct
SEQUENCE: 67
AEAAAKEAAA KEAAAKEAAA KALEAEAAAK EAAAKEAAAK EAAAKA                              46

SEQ ID NO: 68           moltype = AA  length = 12
FEATURE                 Location/Qualifiers
source                  1..12
                        mol_type = protein
                        organism = synthetic construct
SEQUENCE: 68
AEAAAKEAAA KA                                                                   12
```